(12) United States Patent
Motomura et al.

(10) Patent No.: US 9,774,771 B2
(45) Date of Patent: Sep. 26, 2017

(54) PREPARATION, TRANSPARENT PLATE, METHOD FOR PRODUCING PREPARATION, SLIDE GLASS, IMAGING APPARATUS, IMAGING METHOD, PREPARATION PRODUCING APPARATUS, AND PREPARATION COMPONENT SET

(71) Applicant: Panasonic Corporation, Osaka (JP)

(72) Inventors: Hideto Motomura, Kyoto (JP);
Hiroyuki Mori, Osaka (JP); Hiroshi Matsumoto, Kanagawa (JP); Katsuya Watanabe, Tokyo (JP); Kiminori Mizuuchi, Saitama (JP); Naoki Matsubara, Tokyo (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 15/227,668

(22) Filed: Aug. 3, 2016

(65) Prior Publication Data

US 2016/0344908 A1    Nov. 24, 2016

Related U.S. Application Data

(63) Continuation of application No. PCT/JP2015/000458, filed on Feb. 3, 2015.

(30) Foreign Application Priority Data

Mar. 7, 2014   (JP) .................. 2014-044902
Dec. 19, 2014  (JP) .................. 2014-256827

(51) Int. Cl.
*H04N 5/225* (2006.01)
*G01N 1/28* (2006.01)
(Continued)

(52) U.S. Cl.
CPC ............ *H04N 5/2253* (2013.01); *G01N 1/28* (2013.01); *G01N 1/312* (2013.01); *G01N 21/27* (2013.01);
(Continued)

(58) Field of Classification Search
CPC .. H04N 5/2253; H04N 5/2251; H04N 5/2254; H04N 5/32; G01N 1/28;
(Continued)

(56) References Cited

U.S. PATENT DOCUMENTS

| 5,307,161 A | 4/1994 | Miyamoto |
| 6,104,495 A | 8/2000 | Sieben et al. |

(Continued)

FOREIGN PATENT DOCUMENTS

| JP | 2-027111 U | 2/1990 |
| JP | 4-316478 | 11/1992 |

(Continued)

OTHER PUBLICATIONS

International Search Report of PCT application No. PCT/JP2015/000458 dated Apr. 28, 2015.

*Primary Examiner* — Tuan Ho
(74) *Attorney, Agent, or Firm* — Wenderoth, Lind & Ponack, L.L.P.

(57) ABSTRACT

A preparation includes an image sensor, a package, and a transparent plate. The image sensor has an imaging area on a front surface. The package is electrically connected to the image sensor. The transparent plate opposes the front surface of the image sensor with a mounting medium interposed therebetween. On the surface of the transparent plate, first and second grooves are formed. The image sensor is disposed between the first and second grooves.

15 Claims, 43 Drawing Sheets

(51) Int. Cl.

| | | |
|---|---|---|
| *G01N 21/27* | (2006.01) | |
| *G02B 21/36* | (2006.01) | |
| *H01L 31/0203* | (2014.01) | |
| *G01N 1/31* | (2006.01) | |
| *H04N 5/32* | (2006.01) | |
| *H01L 27/146* | (2006.01) | |
| *H04N 5/378* | (2011.01) | |
| *G02B 21/00* | (2006.01) | |
| *G02B 21/34* | (2006.01) | |

(52) U.S. Cl.
CPC ......... *G02B 21/0008* (2013.01); *G02B 21/36* (2013.01); *G02B 21/362* (2013.01); *H01L 27/14618* (2013.01); *H01L 27/14636* (2013.01); *H01L 27/14683* (2013.01); *H01L 31/0203* (2013.01); *H04N 5/2251* (2013.01); *H04N 5/2254* (2013.01); *H04N 5/32* (2013.01); *H04N 5/378* (2013.01); *G02B 21/34* (2013.01); *H01L 2224/48091* (2013.01); *H01L 2224/48227* (2013.01); *H01L 2224/49175* (2013.01); *H01L 2924/16152* (2013.01)

(58) Field of Classification Search
CPC .... G01N 1/312; G01N 21/27; G01N 21/0008; G01N 21/36; G01N 21/362; H01L 27/14618; H01L 27/14636; H01L 27/14683; H01L 31/0203; H01L 2224/4809; H01L 2224/48227; H01L 2924/16152; G02B 21/34
See application file for complete search history.

(56) References Cited

U.S. PATENT DOCUMENTS

| | | |
|---|---|---|
| 2002/0018199 A1 | 2/2002 | Blumenfeld et al. |
| 2006/0279638 A1* | 12/2006 | Matsuda .............. H04N 5/2171 348/208.7 |
| 2006/0283961 A1 | 12/2006 | Misawa et al. |
| 2011/0096157 A1 | 4/2011 | Fine et al. |
| 2012/0286384 A1 | 11/2012 | Ishikida |
| 2014/0091414 A1* | 4/2014 | Shimotsusa ....... H01L 21/76898 257/431 |
| 2014/0094030 A1* | 4/2014 | Shimotsusa ........... H01L 21/768 438/652 |

FOREIGN PATENT DOCUMENTS

| | | |
|---|---|---|
| JP | 11-064215 | 3/1999 |
| JP | 2002-350739 | 12/2002 |
| JP | 2003-515107 | 4/2003 |
| JP | 2006-351772 | 12/2006 |
| JP | 2010-122087 | 6/2010 |
| JP | 2012-238687 | 12/2012 |
| JP | 2013-509618 | 3/2013 |

* cited by examiner

FIG. 34A

| ILLUMINATING DIRECTION | S1 | S2 | S3 | S4 |
|---|---|---|---|---|
| DIRECTION 1 | 0 | 1 | 1 | 0 |
| DIRECTION 2 | 0 | 1/2 | 1 | 1/2 |
| DIRECTION 3 | 0 | 0 | 1/2 | 1 |
| DIRECTION 4 | 1/2 | 1 | 1/2 | 0 |

FIG. 34B

| ILLUMINATING DIRECTION | S1 | S2 | S3 | S4 | S5 | S6 | S7 | S8 |
|---|---|---|---|---|---|---|---|---|
| DIRECTION 1 | 1/2 | 1 | 1 | 1 | 1/2 | 0 | 0 | 0 |
| DIRECTION 2 | 0 | 1/2 | 1 | 1 | 1 | 1/2 | 0 | 0 |
| DIRECTION 3 | 0 | 0 | 1/2 | 1 | 1 | 1 | 1/2 | 0 |
| DIRECTION 4 | 0 | 0 | 0 | 1/2 | 1 | 1 | 1 | 1/2 |
| DIRECTION 5 | 0 | 0 | 0 | 0 | 1/2 | 1 | 1 | 1 |
| DIRECTION 6 | 1 | 1 | 1 | 1/2 | 0 | 0 | 0 | 0 |
| DIRECTION 7 | 1 | 1 | 1/2 | 0 | 0 | 0 | 0 | 0 |
| DIRECTION 8 | 1 | 1/2 | 0 | 0 | 0 | 0 | 0 | 0 |

FIG. 37

| SPECIMEN NUMBER | MAGNIFICATION | IMAGE FEATURE QUANTITY ||||| PATIENT INFORMATION |
|---|---|---|---|---|---|---|
| | | FEATURE 1 | FEATURE 2 | FEATURE 3 | ... | |
| 1 | 1 | 48 | 55 | 95 | ... | NAME A, DISEASE X, FINDINGS |
| 2 | 1 | 6 | 84 | 17 | ... | NAME B, DISEASE Y, FINDINGS |
| 3 | 1 | 19 | 27 | 79 | ... | NAME C, DISEASE Z, FINDINGS |
| 3 | 2 | 81 | 14 | 76 | ... | |
| 4 | 1 | 19 | 27 | 79 | ... | NAME D, DISEASE X, FINDINGS |
| 4 | 2 | 50 | 34 | 94 | ... | |
| ... | ... | | | | ... | ... |

FIG. 38

| SPECIMEN NUMBER | PATIENT ID | MAGNIFICATION | IMAGE FEATURE QUANTITY ||||| PATIENT INFORMATION |
| --- | --- | --- | --- | --- | --- | --- | --- |
| | | | FEATURE 1 | FEATURE 2 | FEATURE 3 | ... | |
| 1 | 1 | 1 | 48 | 55 | 95 | ... | NAME A, DISEASE X, FINDINGS |
| 2 | 2 | 1 | 6 | 84 | 17 | ... | NAME B, DISEASE Y, FINDINGS |
| 3 | 3 | 1 | 19 | 27 | 79 | ... | NAME C, DISEASE Z, FINDINGS |
| | | 2 | 81 | 14 | 76 | ... | |
| 4 | | 1 | 19 | 27 | 79 | ... | NAME D, DISEASE X, FINDINGS |
| | | 2 | 50 | 34 | 94 | ... | |
| ... | ... | ... | | | | | ... |

PREPARATION, TRANSPARENT PLATE, METHOD FOR PRODUCING PREPARATION, SLIDE GLASS, IMAGING APPARATUS, IMAGING METHOD, PREPARATION PRODUCING APPARATUS, AND PREPARATION COMPONENT SET

BACKGROUND

1. Technical Field

The present disclosure relates to a preparation, a transparent plate, a method for producing a preparation, slide glass, an imaging apparatus, an imaging method, a preparation producing apparatus, and a preparation component set.

2. Description of the Related Art

In pathological diagnosis, for the purpose of making a definitive diagnosis or the progression of a lesion, tissue is cut from an internal organ or a tumor and is then examined. In this case, the tissue is further cut into a thin section (slice) having a thickness of about a few or several micrometers (μm) so that it can be examined with a microscope, and is then sandwiched between glass slips. In this manner, a slide (specimen) used for pathological diagnosis is prepared. Pathological diagnosis is essential to determine, for example, whether a cancer is benign or malignant. Therefore, in one hospital, hundreds of specimens are prepared for pathological diagnosis per day. Unlike radiographic images, pathology specimens are difficult to store in the form of digital data. Because of this reason, generally, prepared specimens per se are stored semipermanently so that they can be examined later.

Hitherto, microscopes are used for examining the microstructure of living tissue, for example. The microscope magnifies, by using a lens, an image of an object formed by light passing through or being reflected by the object. An operator directly views the magnified image formed by light passing through or being reflected by the object. If a digital microscope which captures a magnified image of an object by using a camera and displays the captured image on a display is used, more than one operator can examine the same image at the same time, and also, the image can be examined at a remote place. The camera is placed at an imaging point and captures an image magnified by the lens of the microscope.

Japanese Unexamined Patent Application Publication No. 4-316478 discloses a technology for examining the microstructure by using a contact image sensing (CIS) method. In the CIS method, an object is directly placed on the surface of an image sensor, and then, the object is imaged. In the CIS method, a lens for magnifying an image is not used. Accordingly, the resolution is determined by the pixel size of the image sensor. That is, as the pixel size is smaller, a more precise image of the microstructure can be captured.

SUMMARY

One non-limiting and exemplary embodiment implements the application of imaging performed by using the CIS method to practical use.

In one general aspect, the techniques disclosed here feature a preparation including an image sensor, a package, and a transparent plate. The image sensor has a front surface and a back surface opposite the front surface. The front surface includes an imaging area. The package has a front surface and a rear surface and includes a plurality of terminals which are electrically connected to the image sensor via a plurality of electrodes. The front surface of the package contacts or opposes the back surface of the image sensor. The transparent plate is disposed so as to oppose the front surface of the image sensor with a mounting medium interposed therebetween. The mounting medium is used for covering at least part of an object. The transparent plate has first and second grooves on a surface which opposes the front surface of the image sensor. At least part of the image sensor is disposed between the first and second grooves. At least part of each of the plurality of electrodes is positioned within the first groove or the second groove.

According to an embodiment of the present disclosure, it is possible to implement the application of imaging performed by using the CIS method into practical use.

It should be noted that general or specific embodiments may be implemented as a transparent plate, slide glass, a preparation component set, apparatuses, such as an imaging apparatus and a preparation producing apparatus, or methods, such as a preparation producing method and an imaging method, or any selective combination thereof. It should be noted that general or specific embodiments may be implemented as a system, an integrated circuit, a computer program, or a computer-readable recording medium, such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 34A is a view illustrating an example of a matrix representing the relationship between the illuminating directions and the amounts of light to be incident on the image sensor according to the seventh embodiment of the present disclosure;

FIG. 34B is a view illustrating another example of a matrix representing the relationship between the illuminating directions and the amounts of light to be incident on the image sensor according to the seventh embodiment of the present disclosure;

FIG. 37 is a table illustrating an example of a database according to the seventh embodiment of the present disclosure;

FIG. 38 is a table illustrating an example of a database in which plural items of information concerning specimens of different stains of the same patient are associated with each other by using a patient ID according to the seventh embodiment of the present disclosure;

DETAILED DESCRIPTION

In a medical field, a microscope is used for examining cells. Examining the shapes of cells of a subject makes it possible to determine whether or not the subject suffers from a disease, and if it is such a case, to determine whether the disease is benign or malignant and also the benign or malignant stage. In pathological diagnosis, a specimen obtained from a patient is cut into a thin section (slice) having a thickness of about 4 µm so that cells can be examined. Since cells are transparent and the contrast of images captured by a microscope is usually low, cells are stained for making it possible to easily examine the structures of the cells.

Figure 1:
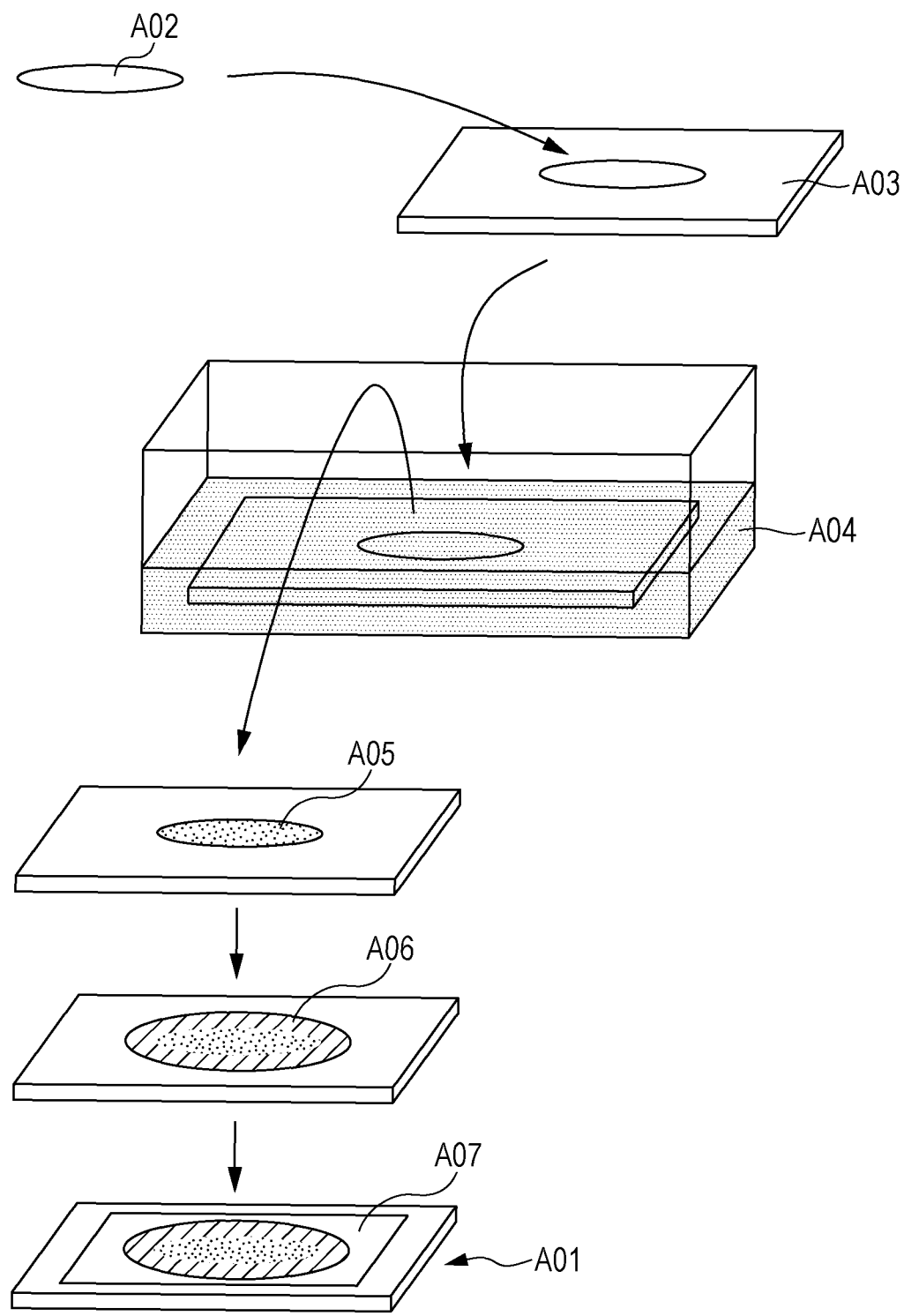
FIG. 1 is a view illustrating an example of a method for producing a preparation used for pathological diagnosis performed by using an optical microscope.

Referring to FIG. 1, an example of a method for producing a preparation A01 used for pathological diagnosis performed by using an optical microscope will be described below.

As shown in FIG. 1, a section (slice) A02 is placed on a transparent plate A03. Generally, slide glass is used as the transparent plate A03. Typical slide glass used for examining objects with an optical microscope has a length of 76 mm, a width of 26 mm, and a thickness of 1 mm. The section A02 is soaked together with the transparent plate A03 in a stain solution A04 and is stained as a result. The section A02 with which the stain solution A04 is attached is called a specimen section (hereinafter may also be called a "stained section A05"). A mounting medium A06 is applied onto the transparent plate A03 so as to protect and fix the stained section A05. Then, cover glass A07 is placed on the transparent plate A03. As a result, the preparation A01 is formed.

Figure 2:
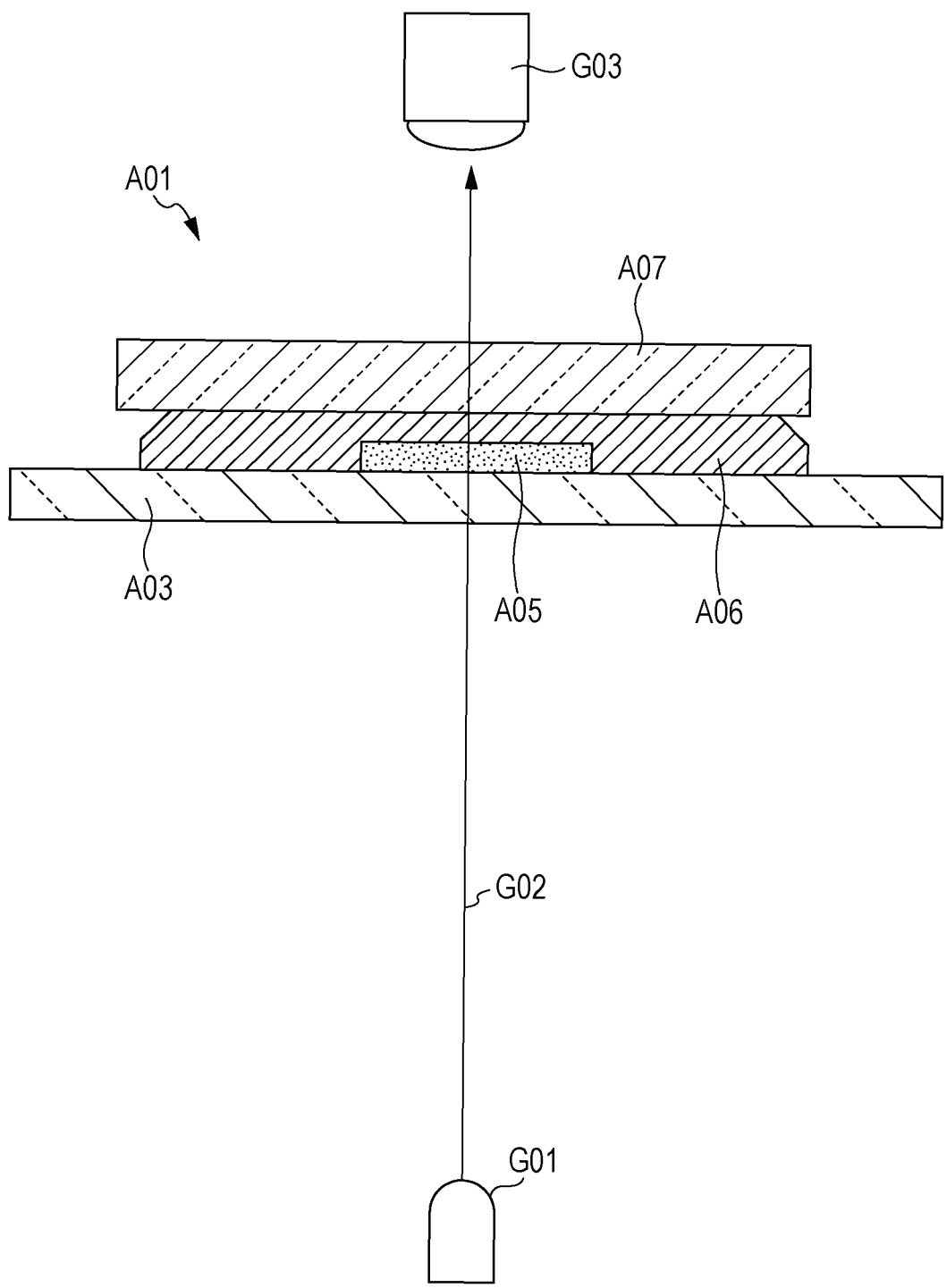
FIG. 2 is a schematic sectional view illustrating a preparation in a state in which it is examined with a microscope.

FIG. 2 is a schematic sectional view illustrating the preparation A01 in a state in which it is examined with a microscope.

As shown in FIG. 2, the stained section A05 is placed on the transparent plate A03. The cover glass A07 is fixed on the transparent plate A03 with the mounting medium A06 interposed therebetween. The stained section A05 is positioned between the cover glass A07 and the transparent plate A03 in a state in which it is surrounded by the mounting medium A06.

The preparation A01 is set under an optical microscope, and then, illumination light G02 is emitted from a light source G01 and is applied to the preparation A01 from the bottom side. The illumination light G02 passes through the transparent plate A03, the stained section A05, the mounting medium A06, and the cover glass A07 and is incident on an objective lens G03 of the optical microscope.

The principle of a CIS examining method will be described below with reference to FIG. 3.

Figure 3:
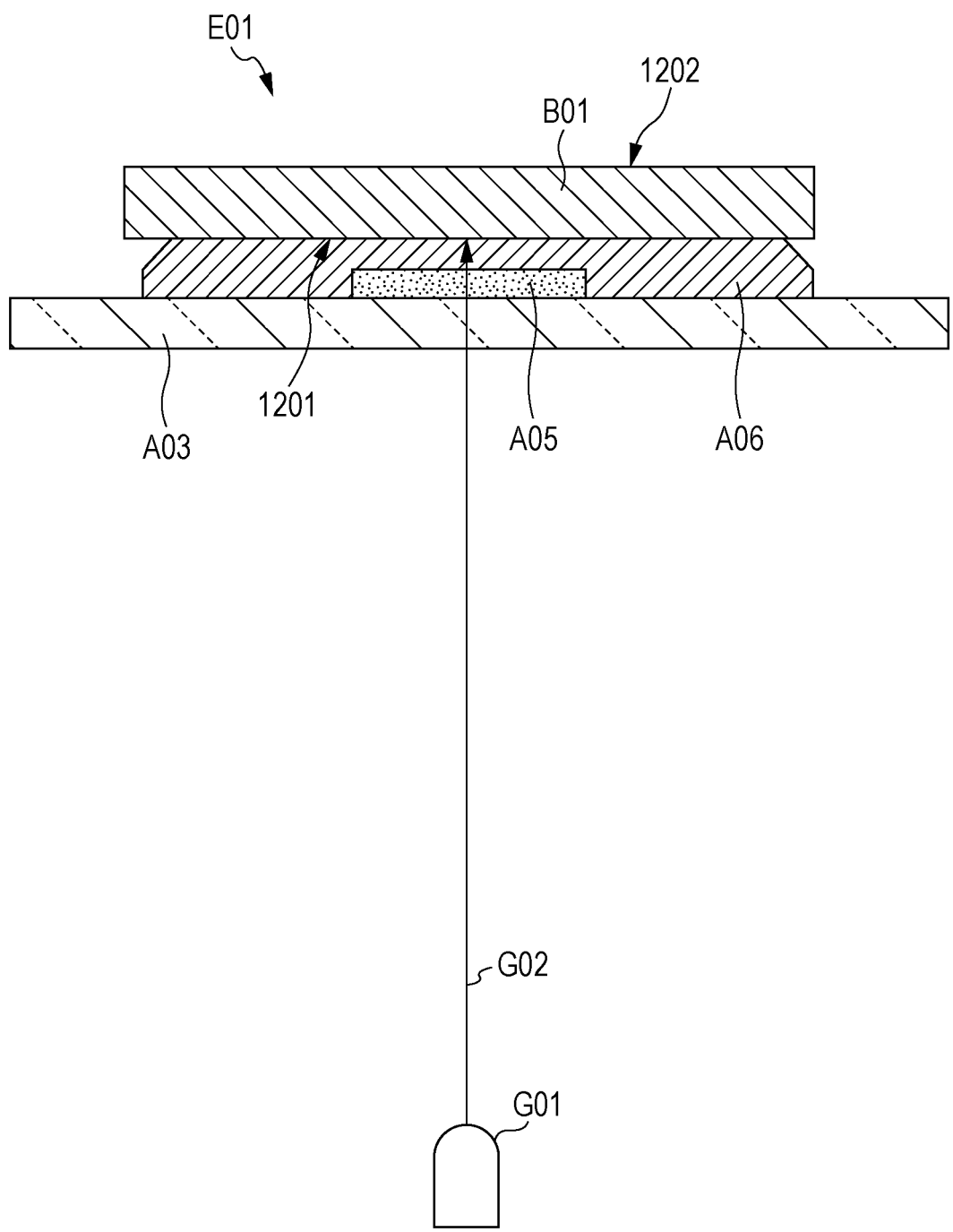
FIG. 3 is a view for explaining the principle of a CIS examining method.

In the example shown in FIG. 3, a preparation E01 includes an image sensor B01 instead of the cover glass A07. The preparation E01 includes the transparent plate (for example, slide glass) A03, the image sensor B01 fixed onto the transparent plate A03 with the mounting medium A06 interposed therebetween, and the stained section (object) A05 surrounded by the mounting medium A06. As the image sensor B01, a solid-state imaging device including many photoelectric converters arranged in a matrix form within an imaging area may be used. Typically, the photoelectric converters are photodiodes formed on a semiconductor layer or a semiconductor substrate. The photoelectric converters receive incident light and generate electric charge. The image sensor B01 has a front surface 1201 and a back surface 1202, which is a surface opposite the front surface 1201. The front surface 1201, which opposes the transparent plate A03, has the imaging area within which the photoelectric converters are arranged.

The resolution of a two-dimensional image sensor is determined by the pitch or the density of photoelectric converters arranged within the imaging area. Nowadays, the pitch of photoelectric converters is almost as short as the wavelength of visible light. Typical examples of the image sensor B01 are a charge coupled device (CCD) image sensor and a metal oxide semiconductor (MOS) image sensor.

In performing an imaging operation, the illumination light G02 passes through the transparent plate A03, the stained section A05, and the mounting medium A06, and reaches the image sensor B01 included in the preparation E01. The image sensor B01 is electrically connected to a circuit, which is not shown in FIG. 3, and performs an imaging operation. The image sensor B01 captures an image of the stained section A05, and then, outputs an image signal reflecting the light transmittance distribution (density distribution) of the stained section A05. As a result, an image of the stained section A05 is obtained.

In the above-described CIS examining method, there is no optical system, such as a lens, interposed between the imaging elements and the stained section A05 (object). However, in the imaging area of the image sensor B01, minute optical detectors (typically, photodiodes) are disposed with high density. Because of this structure, it is possible to obtain an image showing the microstructure of the stained section A05.

In performing an imaging operation by using an image sensor, a drive circuit for driving the image sensor and a processing circuit for processing a signal output from the image sensor are required. Generally, the image sensor is fixed (for example, soldered) to a circuit board including the drive circuit and the processing circuit. When imaging different stained sections, it may be useful if the image sensor is replaced by a new one every time a stained section is imaged, in order to reduce the influence of, for example, stains of a stain solution, adhering on the image sensor. On the other hand, it is not necessary to replace the drive circuit and the processing circuit by new ones every time a stained section is imaged. Thus, in the CIS imaging operation, (1) the same drive circuit and the same processing circuit can be used for different stained sections, and (2) it may be useful if the image sensor is replaced by a new one every time a stained section is imaged.

The summary of various aspects of the present disclosure will be described below.

According to an aspect of the present disclosure, there is provided a preparation including an image sensor, a package, and a transparent plate. The image sensor has a front surface and a back surface opposite the front surface. The front surface includes an imaging area. The package has a front surface and a rear surface and includes a plurality of terminals which are electrically connected to the image sensor via a plurality of electrodes. The front surface of the package contacts or opposes the back surface of the image sensor. The transparent plate is disposed so as to oppose the front surface of the image sensor with a mounting medium interposed therebetween. The mounting medium is used for covering at least part of an object. The transparent plate has first and second grooves on a surface which opposes the front surface of the image sensor. At least part of the image sensor is disposed between the first and second grooves. At least part of each of the plurality of electrodes is positioned within the first groove or the second groove.

The first and second grooves may be parallel with each other. In a state in which the surface of the transparent plate on which the first and second grooves are formed opposes the front surface of the image sensor, a direction in which the first and second grooves extend and a direction in which the plurality of electrodes are arranged may be parallel with each other.

The first and second grooves may extend from one end to the other end of the transparent plate.

The transparent plate may also have third and fourth grooves on the surface on which the first and second grooves are formed. The third and fourth grooves may be provided in parallel with each other while being perpendicular to the first and second grooves.

According to an aspect of the present disclosure, there is provided a transparent plate on which an image sensor and a package are mountable in order of the image sensor and the package. The image sensor has a front surface and a back surface opposite the front surface. The front surface includes an imaging area. The package has a front surface and a rear surface and includes a plurality of terminals which are electrically connected to the image sensor via a plurality of electrodes. The front surface of the package contacts or opposes the back surface of the image sensor. The transparent plate has first and second grooves on a surface of the transparent plate. In a state in which the front surface of the image sensor opposes the surface of the transparent plate on which the first and second grooves are formed, at least part of the image sensor is disposed between the first and second grooves with a mounting medium interposed therebetween, the mounting medium being used for covering at least part of an object, and at least part of each of the plurality of electrodes is positioned within the first groove or the second groove.

The first and second grooves may be parallel with each other, and in a state in which the image sensor is disposed between the first and second grooves, the first and second grooves may extend in parallel with a direction in which the plurality of electrodes are arranged.

The first and second grooves may extend from one end to the other end of the transparent plate.

The transparent plate may also have third and fourth grooves on the surface on which the first and second grooves are formed. The third and fourth grooves may be provided in parallel with each other while being perpendicular to the first and second grooves.

According to an aspect of the present disclosure, there is provided a method for producing a preparation. The method includes: preparing an image sensor unit including an image sensor and a package, the package including a plurality of terminals which are electrically connected to the image sensor via a plurality of electrodes; disposing an object on a surface of a transparent plate on which first and second grooves are formed or on an imaging area of the image sensor; applying a mounting medium to the object; disposing, before the mounting medium dries, at least part of the image sensor unit between the first and second grooves in a state in which the surface of the transparent plate opposes the imaging area of the image sensor with the mounting medium interposed therebetween, so as to position at least part of each of the plurality of electrodes within the first groove or the second groove; and fixing the image sensor unit and the transparent plate by drying the mounting medium.

According to an aspect of the present disclosure, there is provided an imaging apparatus including a socket, a light source unit, and a control device. On the socket, the above-described preparation is mountable. The socket is electrically connected to the image sensor via the plurality of terminals of the package of the preparation. The light source unit emits light to be incident on the image sensor via the transparent plate of the preparation mounted on the socket. The control device controls the light source unit and the image sensor of the preparation mounted on the socket so as to cause the image sensor to image the object in the preparation.

The light source unit may include a plurality of light sources or a light source which is movable. The control device may perform control so that light will be applied to the object a plurality of times at different angles so as to image the object at each of the different angles.

According to an aspect of the present disclosure, there is provided an imaging method including: mounting the preparation according to claim 1 on a socket of an imaging apparatus so as to electrically connect the socket to the image sensor via the plurality of terminals of the package of the preparation; emitting light from a light source unit to be incident on the image sensor via the transparent plate of the preparation; and causing the image sensor to image the object in the preparation mounted on the socket by controlling the light source unit and the image sensor of the preparation.

The light source unit may include a plurality of light sources or a light source which is movable. In the causing of the image sensor to image the object, light may be applied to the object a plurality of times at different angles so as to image the object at each of the different angles.

According to an aspect of the present disclosure, there is provided a preparation producing apparatus including a table and a movable unit. The table supports slide glass on which a specimen section is placed. The movable unit fixes an image sensor unit to the slide glass by bringing the image sensor unit close to the slide glass. The image sensor unit includes an image sensor and a package. The image sensor has a front surface and a back surface. The package has a front surface and a rear surface. The package supports the image sensor so that the front surface of the package contacts or opposes the back surface of the image sensor. The package includes a plurality of terminals which are electrically connected to the image sensor via a plurality of electrodes. The slide glass is disposed so as to oppose the front surface of the image sensor. The slide glass has first and second grooves on a surface which opposes the front surface of the image sensor. At least part of the image sensor is disposed between the first and second grooves. At least part of each of the plurality of electrodes is positioned within the first groove or the second groove.

According to an aspect of the present disclosure, there is provided a preparation component set including an image sensor unit and a transparent plate. The image sensor unit includes an image sensor and a package. The image sensor has a front surface and a back surface. The package has a front surface and a rear surface and includes a plurality of terminals which are electrically connected to the image sensor via a plurality of electrodes. The front surface of the package contacts or opposes the back surface of the image sensor. The transparent plate is disposed so as to oppose the front surface of the image sensor with an object interposed therebetween. At least part of the object is covered with a mounting medium. The transparent plate has first and second grooves on a surface which opposes the front surface of the image sensor. At least part of the image sensor is positionable between the first and second grooves, and at least part of each of the plurality of electrodes is positionable within the first groove or the second groove.

Embodiments of the present disclosure will be described below in detail with reference to the accompanying drawings.

All of the embodiments described below illustrate general or specific examples. Numeric values, configurations, materials, components, arrangement thereof, positions and connection states thereof, steps, and order of steps illustrated in the following embodiments are only examples, and are not described for limiting the present disclosure. Among the components illustrated in the following embodiments, components that are not recited in the independent claims which embody the broadest concept of the present disclosure will be described as optional components. In the following description, components having substantially the same function are designated by like reference numerals, and an explanation thereof may be given only once.

First Embodiment

An example of a method for producing a preparation according to a first embodiment of the present disclosure will be described below with reference to FIG. 4.

Figure 4:
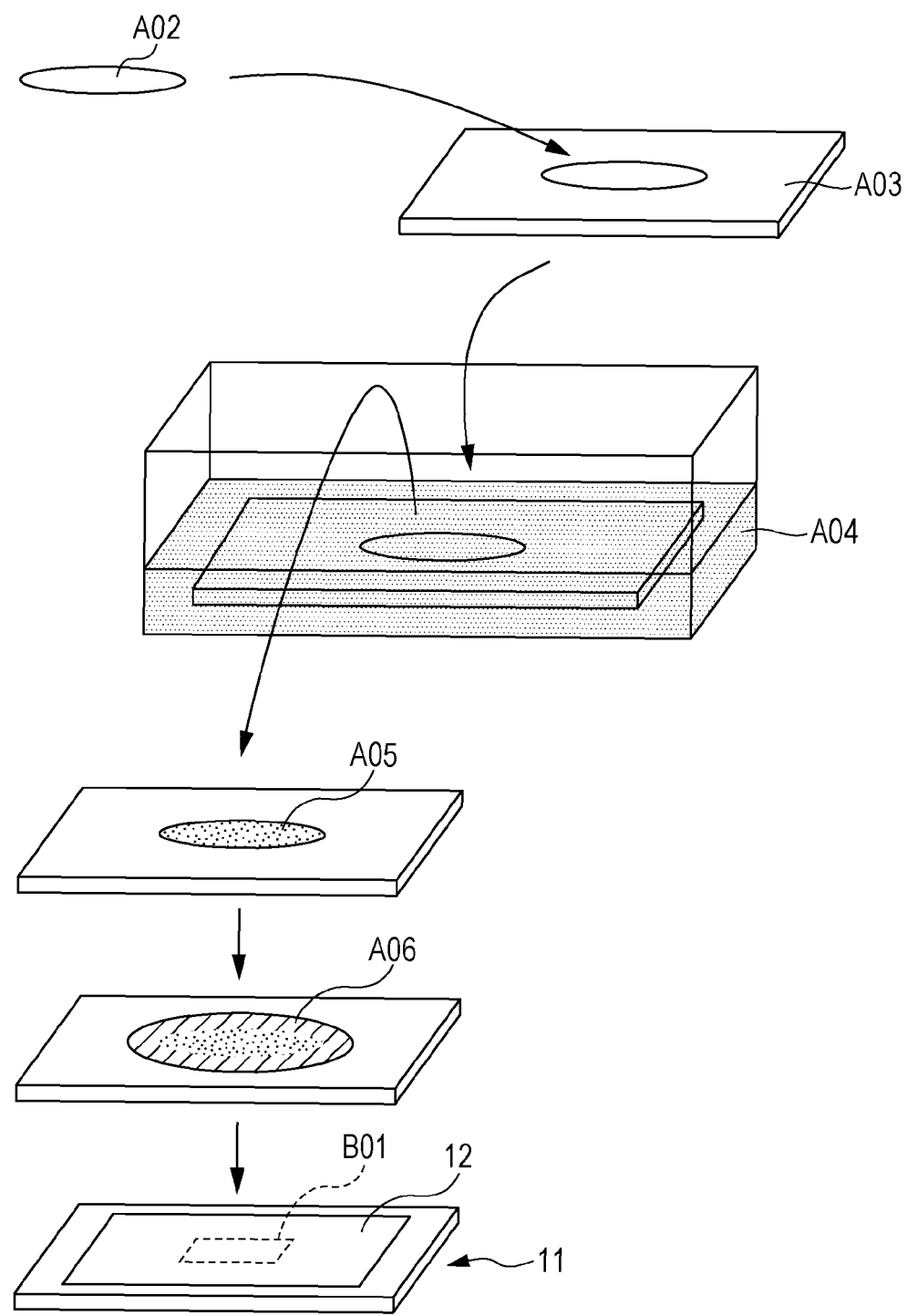
FIG. 4 is a view illustrating an example of a method for producing a preparation according to a first embodiment of the present disclosure.

As shown in FIG. 4, a section (slice) A02 is placed on a transparent plate A03. As the transparent plate A03, general slide glass, for example, may be used. Slide glass used as a transparent plate may have a recessed portion or a groove, which will be described later. The section A02 is soaked together with the transparent plate A03 in a stain solution A04 and is stained as a result. The section A02 with which the stain solution A04 is attached is called a stained section A05. A mounting medium A06 is applied onto the transparent plate A03 so as to protect and fix the stained section A05. Then, instead of the cover glass A07 shown in FIG. 1, the image sensor B01 is placed on the transparent plate A03. In the example shown in FIG. 4, a package 12 is fixed to the image sensor B01 from the bottom side of the image sensor B01. As a result, a preparation 11 is formed.

Figure 5:
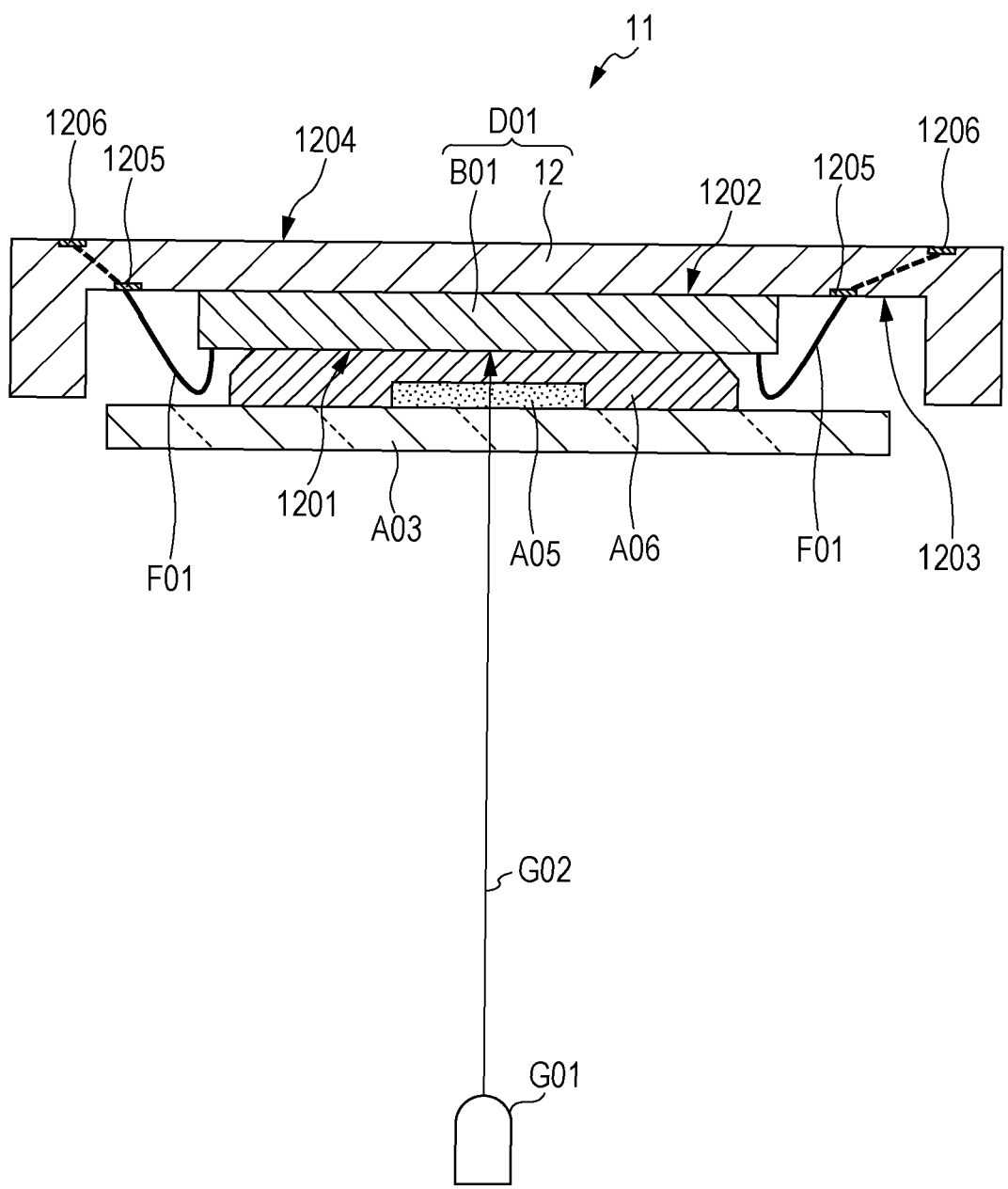
FIG. 5 is a schematic sectional view illustrating an example of the configuration of a preparation including an image sensor and a package in the first embodiment.

FIG. 5 is a schematic sectional view illustrating an example of the configuration of the preparation 11 including the image sensor B01 and the package 12. In the example shown in FIG. 5, the image sensor B01 is housed within the package 12. In the configuration shown in FIG. 5, the image sensor B01 and the package 12 are electrically connected to each other by using wire electrodes (bonding wires) F01. In the example shown in FIG. 5, the transparent plate A03 is disposed so as to oppose the front surface 1201 of the image sensor B01 with the mounting medium A06, which covers the stained section (object) A05, interposed therebetween.

The package 12 has a front surface 1203 and a rear surface 1204, which is a surface opposite the front surface 1203. In FIG. 5, the package 12 has a bottom surface (front surface) 1203 and wall surfaces (side walls) which form a space for housing the image sensor B01 therein. As shown in FIG. 5, the front surface 1203 may have plural first terminals 1205. The rear surface 1204 may have plural second terminals 1206. As in the image sensor B01 discussed with reference to FIG. 3, the image sensor B01 shown in FIG. 5 has the front surface 1201 having the imaging area and a back surface 1202, which is a surface opposite the front surface 1201. In the configuration shown in FIG. 5, the front surface 1203 of the package 12 opposes the back surface 1202 of the image sensor B01. The front surface 1203 of the package 12 and the back surface 1202 of the image sensor B01 may be in contact with each other. The package 12 of the preparation 11 supports the image sensor B01 so that the front surface 1203 of the package 12 may oppose or contact the back surface 1202 of the image sensor B01.

As illustrated in FIG. 5, the plural first terminals 1205 and the image sensor B01 may be electrically connected to each other by using the plural electrodes F01. In the configuration illustrated in FIG. 5, an electric signal from each of the plural first terminals 1205 is transmitted to a corresponding one of the plural second terminals 1206 via a corresponding wiring provided in the package 12. In FIG. 5, the wirings which connect the plural first terminals 1205 and the corresponding plural second terminals 1206 are schematically indicated by the dotted lines. Hereinafter, a set of an image sensor and a package supporting the image sensor may be referred to as an "image sensor unit". As shown in FIG. 5, in an image sensor unit D01, the package 12 supports the image sensor B01 so that the front surface 1203 of the package 12 may oppose or contact the back surface 1202 of the image sensor B01. In the image sensor unit D01, the image sensor B01 and the package 12 are electrically connected to each other. Electrical connection between the image sensor B01 and the package 12 may be implemented by using, for example, the plural electrodes F01.

Figure 6:
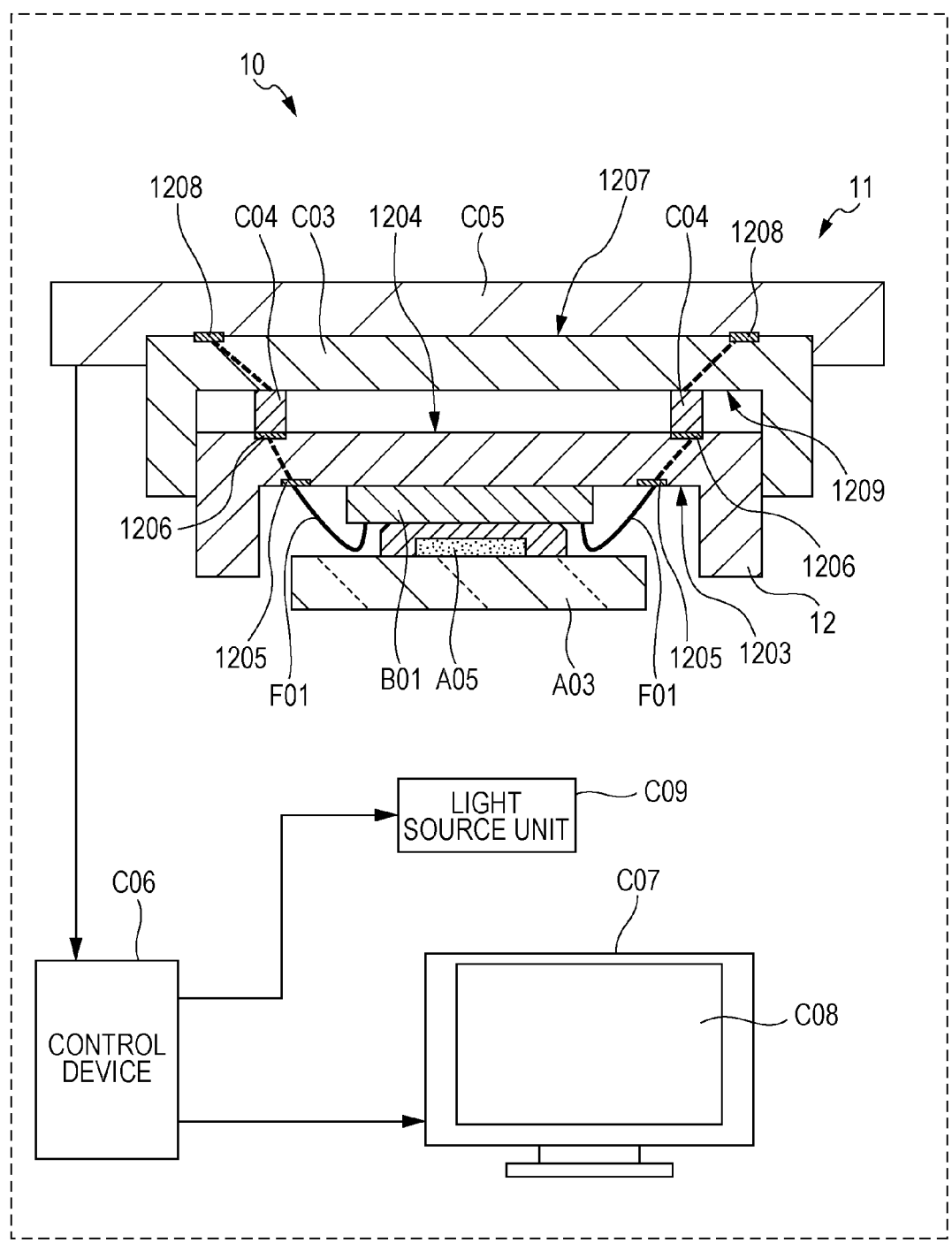
FIG. 6 is a schematic view illustrating an example of the configuration of an imaging apparatus which may be usable for imaging a stained section included in the preparation.

FIG. 6 schematically illustrates an example of the configuration of an imaging apparatus 10 which may be used for imaging the stained section A05 included in the preparation 11.

The imaging apparatus 10 shown in FIG. 6 includes a socket C03 which is configured to mount the preparation 11 thereon. The socket C03 has a rear surface 1207 and a front surface 1209, which is a surface opposite the rear surface 1207. The socket C03 may have recessed portions which receive the package 12 of the preparation 11 therein. As shown in FIG. 6, the rear surface 1207 may have plural terminals 1208, and the front surface 1209 may have plural terminals C04. An electric signal from each of the plural terminals C04 is transmitted to a corresponding one of the plural terminals 1208 via a corresponding wiring provided in the socket C03. In FIG. 6, the wirings which connect the plural terminals C04 and the corresponding plural terminals 1208 are schematically indicated by the dotted lines.

The socket C03 is electrically connected to a circuit board C05. Electrical connection between the socket C03 and the circuit board C05 may be implemented by bringing the plural terminals 1208 provided on the rear surface 1207 of the socket C03 into contact with wirings or electrode pads provided on the circuit board C05. In the configuration illustrated in FIG. 6, the socket C03 is electrically connected to the image sensor B01 via the plural terminals C04 of the socket C03, the plural second terminals 1206 disposed on the rear surface 1204 of the package 12, the plural first terminals 1205 disposed on the front surface 1203 of the package 12, and the plural electrodes F01.

As the circuit board C05, a known circuit board may be used. By using one of various known methods for mounting an electronic component on a circuit board, the socket C03 may be mounted on the circuit board C05. The socket C03 may be removably attached to the circuit board C05, or may be fixed onto the circuit board C05 by means of, for example, soldering. If the socket C03 is fixed on the circuit board C05, it can be said that the circuit board C05 includes the socket C03.

In the first embodiment of the present disclosure, the preparation 11 is attachable to and detachable from the socket C03. In the configuration illustrated in FIG. 6, when the preparation 11 is mounted on the socket C03 on the circuit board C05, the plural second terminals 1206 of the package 12, which are electrically connected to the image sensor B01, and the plural terminals C04 of the socket C03 are brought into contact with each other. With this contact operation, the package 12 and the socket C03 are electrically connected to each other, and then, the image sensor B01 and the socket C03 are electrically connected to each other via the plural first terminals 1205 and the plural second terminals 1206 of the package 12. Further, via the socket C03, the plural first terminals 1205 (may be the plural second terminals 1206) of the package 12 and the circuit board C05 are electrically connected to each other. That is, in this example, by mounting the preparation 11 on the socket C03, electrical connection between the image sensor B01 and the circuit board C05 is established. By this electrical connection, the circuit board C05 is able to receive output from the image sensor B01. In the first embodiment, the preparation 11 is temporarily fixed to the socket C03 by using the socket C03 or another mechanism. Upon completion of imaging of the preparation 11, which is a current object, the preparation 11 is removed from the socket C03, and another preparation 11, which is a subsequent object, is mounted on the socket C03.

The imaging apparatus 10 includes a light source unit C09 which emits light to be incident on the image sensor B01 via the transparent plate A03 of the preparation 11 mounted on the socket C03. The light source unit C09 includes one or more light sources. In the example shown in FIG. 6, the light source unit C09 is located below the preparation 11. However, the embodiments of the present disclosure are not restricted to this example.

The imaging apparatus 10 includes a control device (control personal computer (PC)) C06. The control device C06 controls the light source unit C09 and the image sensor B01 of the preparation 11 mounted on the socket C03 so as to cause the image sensor B01 to image the stained section A05 (object) of the preparation 11.

As described above, in this example, the package 12 is electrically connected to the socket C03 via the plural terminals C04 of the socket C03. The socket C03 includes terminals or electrodes (the plural terminals 1208 in this example), which allow the socket C03 to be electrically connected to the circuit board C05, on the rear surface 1207 or a side surface. The circuit board C05 is connected to the control PC C06. An image C08 of the stained section A05 captured by the image sensor B01 is displayed on, for example, a display C07. The image C08 may be stored in a memory or a database, neither of which is shown.

Figure 7A:
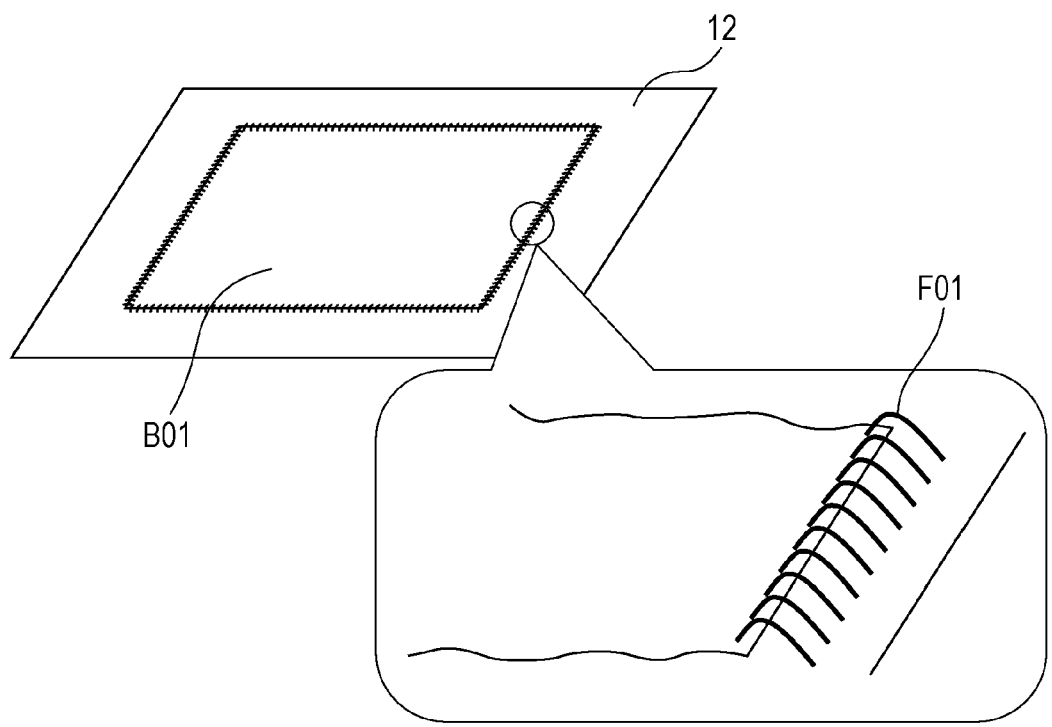
FIG. 7A is a perspective view illustrating an example of the arrangement of electrodes.

In the example shown in FIG. 6, electrical connection between the image sensor B01 and the package 12 is implemented by using plural bonding wires, that is, the plural wire electrodes F01. As shown in FIG. 7A, the electrodes F01 may be formed of thin metal wires and be densely arranged around the image sensor B01. The configuration of the image sensor B01 and that of the package 12 may be similar to those of a known image sensor and a known package. The shape of the electrode F01 is not restricted to the shape of a wire, such as that shown in FIG. 7A.

Figure 7B:
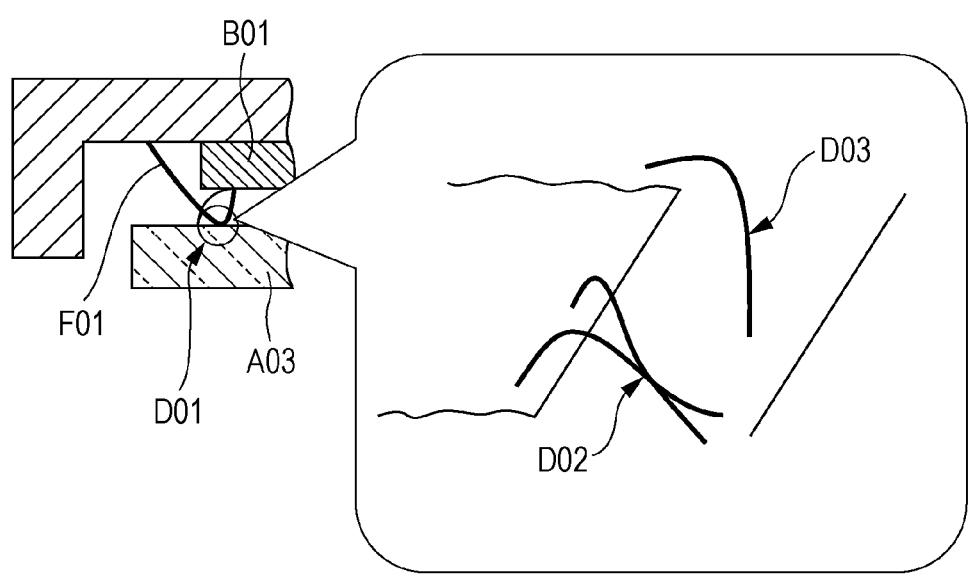
FIG. 7B is a view schematically illustrating a state in which a transparent plate contacts an electrode.

It is assumed that the electrodes F01 are formed in the shape of a wire, such as that shown in FIG. 7A. In this case, if the transparent plate A03 contacts the electrode F01 (the portion indicated by the arrow D01 in FIG. 7B), as shown in FIG. 7B, the electrode F01 may be deformed or adjacent electrodes F01 may be brought into contact with each other. This may cause short-circuiting between the electrodes F01 (the portion indicated by the arrow D02 in FIG. 7B) or cause damage or breakage (the portion indicated by the arrow D3 in FIG. 7B) of the electrode F01. Because of this reason, it may be useful if the size and the configuration of the electrode F01 are determined so that the electrode F01 may not strike the transparent plate A03.

Second Embodiment

Figure 8:
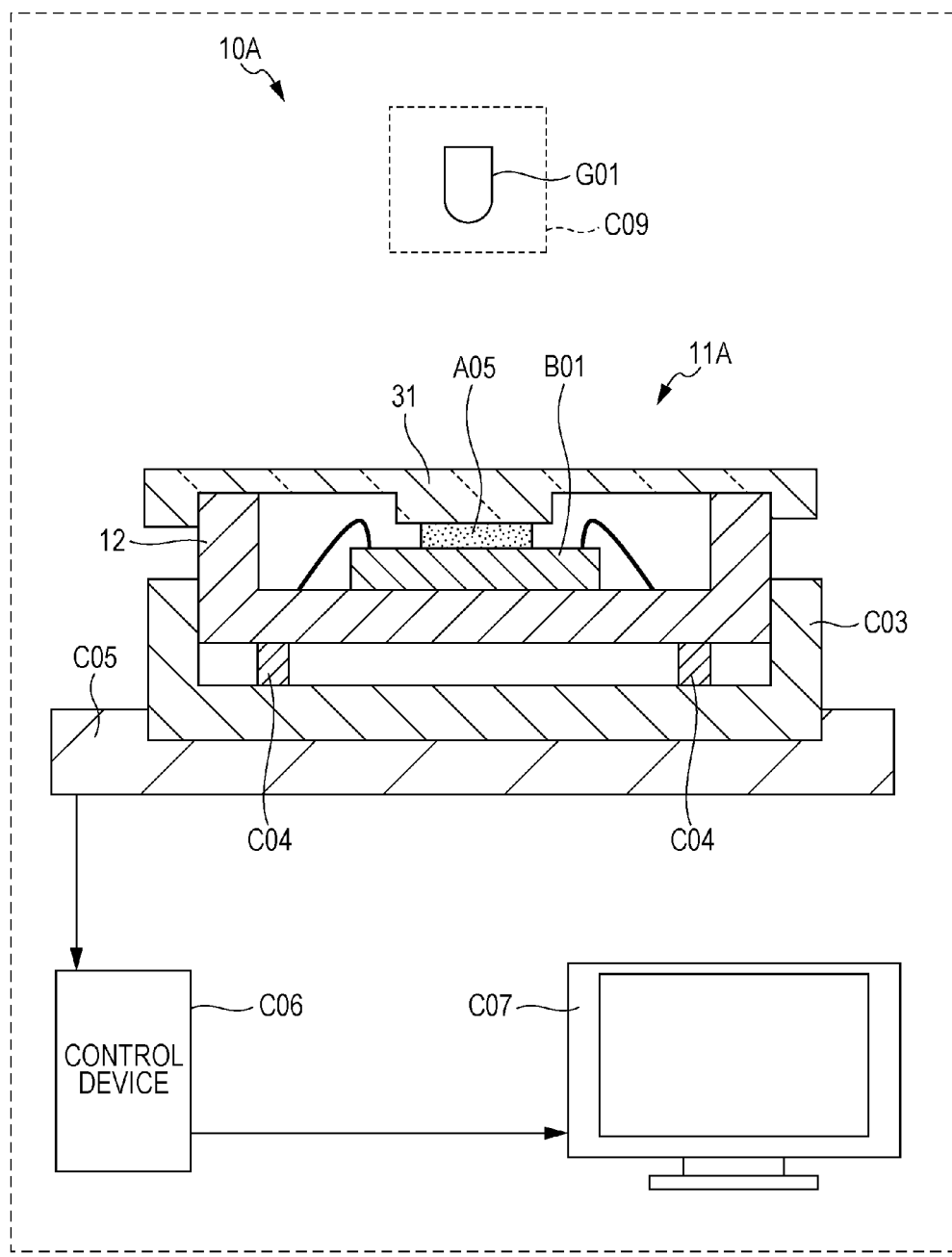
FIG. 8 is a schematic view illustrating the configuration of an imaging apparatus according to a second embodiment of the present disclosure and also illustrating the cross-sectional structure of a preparation mounted on the imaging apparatus.

FIG. 8 is a schematic view illustrating the configuration of an imaging apparatus 10A according to a second embodiment of the present disclosure. FIG. 8 also schematically illustrates the cross-sectional structure of a preparation 11A mounted on the imaging apparatus 10A. For a simple representation, the mounting medium A06 is not always shown.

As shown in FIG. 8, the imaging apparatus 10A includes a socket C03 and a light source unit C09. The socket C03 is mounted on a circuit board C05. In the example shown in FIG. 8, the preparation 11A including a transparent plate 31 is mounted on the socket C03. The structure of the transparent plate 31 will be described later. The socket C03 may be configured to mount the preparation 11 shown in FIG. 5 or to mount the preparation 11A. The socket C3 may be configured to mount one or more preparations (for example, the preparations 11 and 11A). In the example shown in FIG. 8, light emitted from a light source G01 is incident on the image sensor B01 via the transparent plate 31 of the preparation 11A mounted on the socket C03. In the configuration illustrated in FIG. 8, the imaging apparatus 10A also includes a control PC C06 and a display C07. The control PC C06 controls the light source unit C09 and the image sensor B01 so as to cause the image sensor B01 to image an object (stained section). The display C07 displays an image obtained by imaging the object.

The socket C3 is electrically connected to the image sensor B01 via terminals (not shown in FIG. 8) of the package 12 of the preparation 11A.

Figure 9:
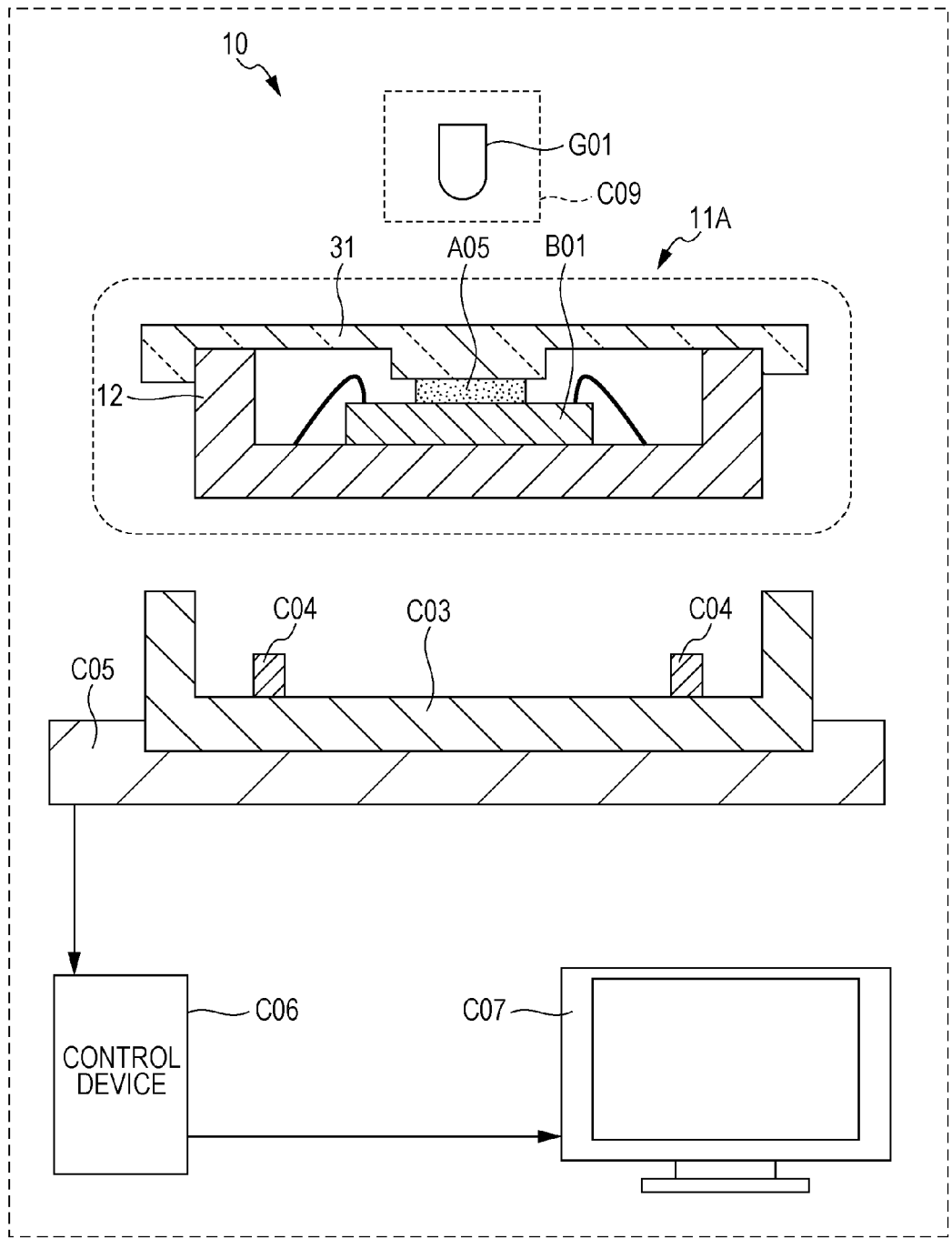
FIG. 9 is a schematic sectional view illustrating a preparation and a socket immediately before the preparation is mounted on the socket.

Connection between the preparation 11A and the socket C03 will be discussed below with reference to FIG. 9. FIG. 9 schematically illustrates the cross-sectional structure of the preparation 11A and that of the socket C03 immediately before the preparation 11A is mounted on the socket C03.

The socket C03 includes plural terminals C04. The plural terminals C04 are located so that they may be associated with plural terminals (for example, the plural second terminals 1206 shown in FIG. 6), which are not shown in FIG. 9, of the package 12 of the preparation 11A. When the preparation 11A is mounted on the socket C03, the plural terminals of the package 12 of the preparation 11A contact the associated plural terminals C04 of the socket C03. As a result, electrical connection between the preparation 11A and the socket C03 is established. In the second embodiment, as well as in the first embodiment, the preparation 11A is attachable to and detachable from the socket C03, and is temporarily fixed to the socket C03 by using the socket C03 or another mechanism. Upon completion of imaging of the preparation 11A, the preparation 11A is removed from the socket C03, and another preparation 11A is mounted on the socket C03. In the other embodiments, the preparation is treated in a similar manner.

In the second embodiment, the transparent plate 31 of the preparation 11A has recessed portions on the surface which opposes the front surface of the image sensor B01 (the surface of the image sensor B01 on which the imaging area is formed and on which light is incident when imaging is performed). This will be described in detail below.

Figure 10:
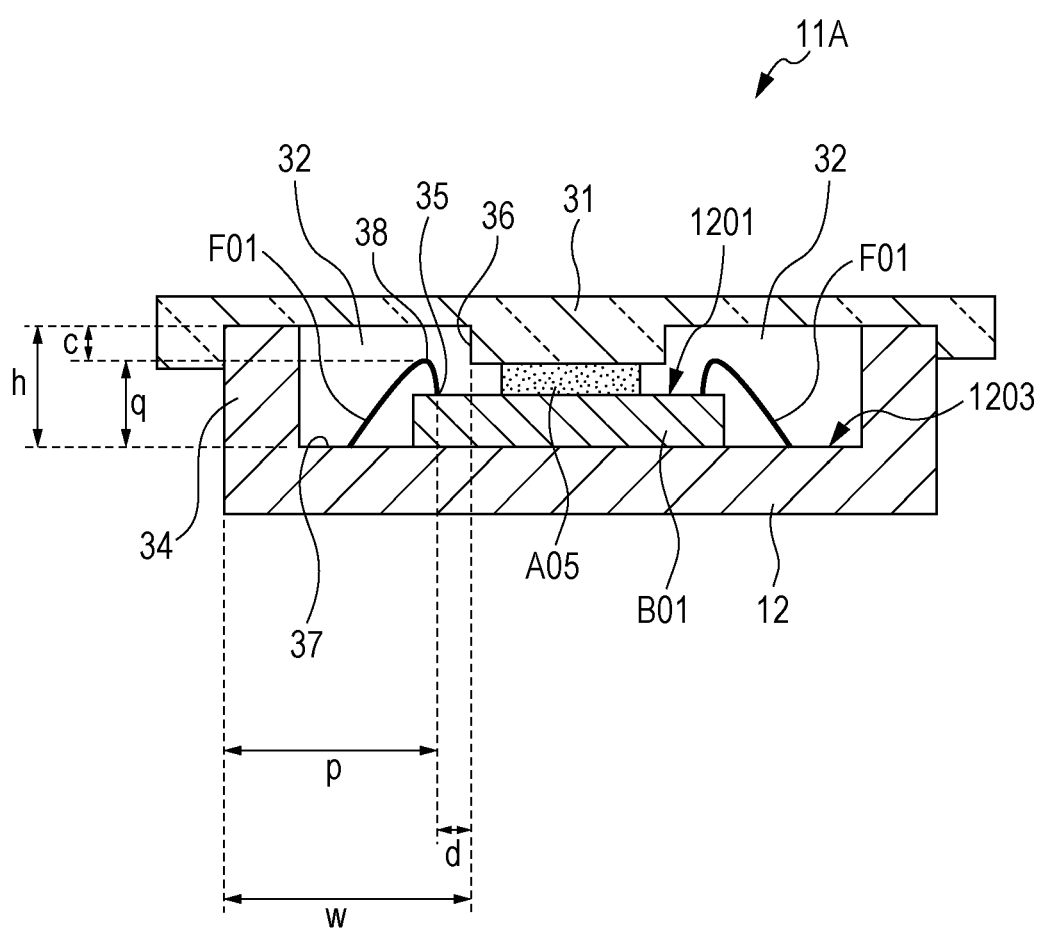
FIG. 10 is a schematic sectional view illustrating the preparation according to the second embodiment.

FIG. 10 schematically illustrates the cross-sectional structure of the preparation 11A of the second embodiment. As shown in FIG. 10, the transparent plate 31 of the preparation 11A has a recessed portion 32 in which at least part of each of plural electrodes F01 connected to the image sensor B01 can be stored. The recessed portion 32 of the transparent plate 31 may be a groove extending along the outer edge of the front surface 1201 of the image sensor B01. The groove may be constituted by a portion extending along the outer edge of the front surface 1201 of the image sensor B01 and a portion extending from the outer edge of the image sensor B01 toward the edge of the transparent plate 31. That is, the groove may be constituted by a portion extending along the outer edge of the front surface of the image sensor B01 and a portion protruding from this outer edge outward.

In FIG. 10, signs (c, d, h, p, q, and w) representing the sizes of the portions are indicated. The sizes of the portions shown in FIG. 10 are exaggerated for the purpose of easy understanding, and do not necessarily represent the actual sizes. The other figures are drawn in a similar manner.

In the preparation 11A shown in FIG. 10, the package 12 having the image sensor B01 mounted thereon has a side wall 34 protruding from the front surface 1203 at the edge of the package 12, and the forward end of this side wall 34 is located within the recessed portion 32 of the transparent plate 31. That is, the recessed portion 32 may be formed in such a shape as to receive the forward end of the side wall 34. The stained section A05 is located between the front surface 1201 of the image sensor B01 and the flat portion of the transparent plate 31. The flat portion of the transparent plate 31 on which the stained section A05 is placed is typically a central area of the transparent plate 31 and at least part of an area where the recessed portion 32 is not formed on the front surface of the transparent plate 31. The distance between the front surface 1201 of the image sensor B01 and the flat portion of the transparent plate 31 is determined by structure parameters, such as the height of the side wall 34 of the package 12 and the depth of the recessed portion 32.

The image sensor B01 and the package 12 are electrically connected to each other by using plural wire electrodes F01. As viewed in a direction normal to the front surface 1201 of the image sensor B01, the plural electrodes F01 are positioned within the recessed portion 32 of the transparent plate 31. By providing the recessed portion 32 in the transparent plate 31, it is possible to prevent the contact or the interference between the electrodes F01 and the transparent plate 31.

In the second embodiment, the width w of the recessed portion 32, that is, the size of the recessed portion 32 in the horizontal direction in the plane of the drawing in FIG. 10, may be expressed by equation (1).

$$w = p + d \quad (1)$$

In equation (1), p is the distance from the outer edge of the package 12 (the edge in the horizontal direction in the plane of the drawing) to a contact 35 between the electrode F01 and the image sensor B01, and d is the distance from the contact 35 to a wall 36 formed at a position inward of the recessed portion 32. The condition that the transparent plate 31 does not contact the electrode F01 is d>0. Accordingly, equation (2) holds true.

$$w > p \quad (2)$$

It is assumed that the front surface 1203 (in this case, the surface of a bottom portion 37) of the package 12 is a reference surface. In this case, the height h from the front surface 1203 to the surface of the recessed portion 32 may be expressed by equation (3).

$$h = q + c \quad (3)$$

In equation (3), q is the distance from the front surface 1203 of the package 12 to an apex 38 of the electrode F01, and c is the distance from the apex 38 of the electrode F01 to the surface of the recessed portion 32. The condition that the transparent plate 31 does not contact the electrode F01 is c>0. Accordingly, equation (4) holds true.

$$h > p \quad (4)$$

In the example shown in FIG. 10, equations (1) through (4) have been explained by focusing on the recessed portion 32 on the left side of the package 12. The same conditions are established for the recessed portion 32 on the right side of the package 12 shown in FIG. 10.

An example of the method for producing the preparation 11A according to the second embodiment will now be described below with reference to FIG. 11.

As an example of the transparent plate 31, slide glass having a recessed portion formed on the surface will be used. In this example, as the recessed portion 32, a substantially square groove is formed on the surface of the slide glass. In this specification, "slide glass" is not restricted to simple glass plates, but widely includes transparent members having a recessed portion or a groove formed on the surface.

First, a section (slice) A02 is placed on a flat region surrounded by the recessed portion 32 of the transparent plate 31 (in this case, slide glass having a recessed portion). The section A02 is soaked together with the transparent plate 31 in a stain solution A04 and is stained as a result. The section A02 with which the stain solution A04 is attached is called a stained section A05. A mounting medium is applied onto the transparent plate 31 so as to protect and fix the stained section A05. Then, the package 12 having the image sensor B01 mounted thereon is placed on the transparent plate 31 so that the front surface of the image sensor B01 and the front surface of the transparent plate 31 having the recessed portion 32 formed thereon may oppose each other with the object (in this case, the stained section A05) interposed therebetween. In this state, in the second embodiment, the recessed portion 32 stores at least part of each of the plural electrodes F01 connected to the image sensor B01 therein. The package 12 is positioned so that the forward ends of the side walls 34 of the package 12 may be located within the recessed portion 32 of the transparent plate 31. In other words, a step of fixing the transparent plate 31 and the image sensor B01 may include a step of inserting the forward ends of the side walls 34 of the package 12 into the recessed portion 32 of the transparent plate 31. In FIG. 11, the rear surface 1204 of the package 12 is shown. Although the package 12 is drawn as a thin element in FIG. 11 for a simple representation, it has a certain thickness in actuality.

Figure 12:
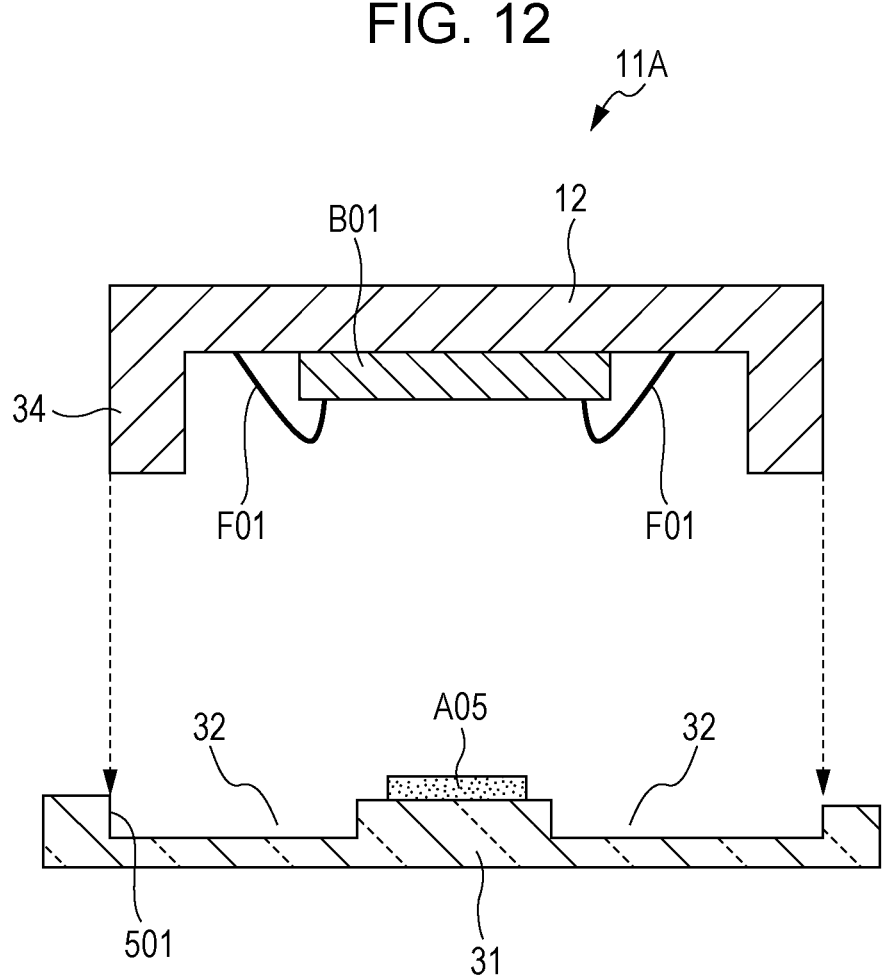
FIG. 12 is a view illustrating an example of the positional relationship between a side wall of a package and an inner wall of the outer edge of a recessed portion of a transparent plate.

FIG. 12 illustrates an example of the positional relationship between the side wall 34 of the package 12 and an inner wall 501 of the outer edge of the recessed portion 32 of the transparent plate 31. In this example, the position of the outer edge of the side wall 34 of the package 12 is aligned with the position of the inner wall 501 of the recessed portion 32 of the transparent plate 31. However, this is not always necessary. When the side wall 34 of the package 12 is inserted into the recessed portion 32 of the transparent plate 31, a gap may be formed between the side wall 34 of the package 12 and the inner wall 501 of the recessed portion 32 of the transparent plate 31.

Figure 13A:
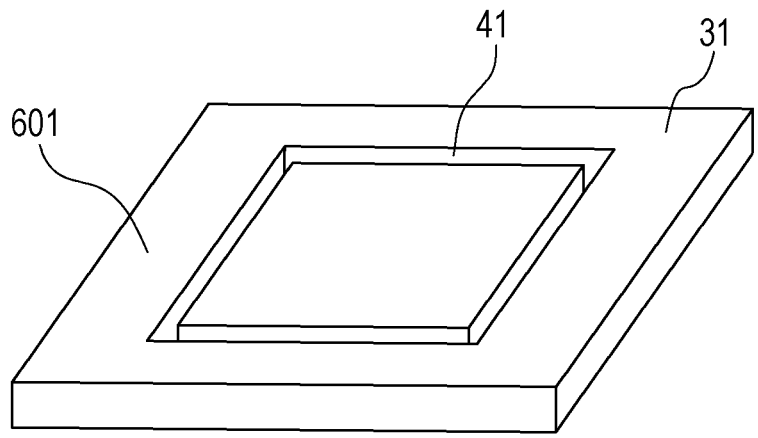
FIG. 13A is a perspective view illustrating an example of a transparent plate having a groove extending along the four sides of a substantially square.
Figure 13B:
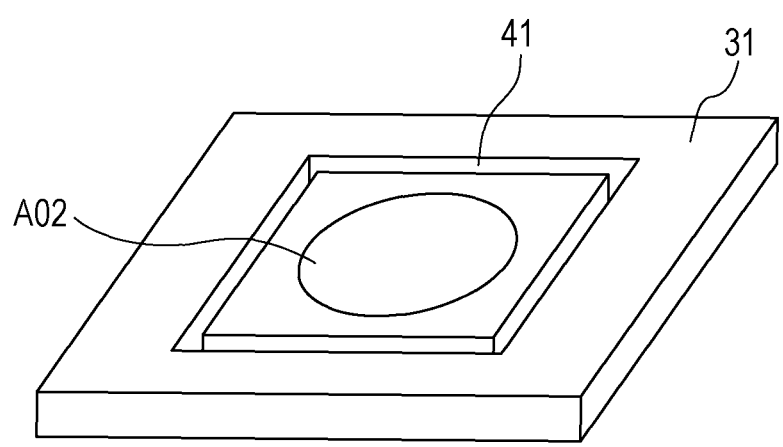
FIG. 13B is a perspective view illustrating a state in which a specimen section is placed within a flat region surrounded by the groove.

In the second embodiment, as shown in FIG. 7A, many electrodes F01 are disposed on the four sides of the image sensor B01. As shown in FIG. 13A, the recessed portion 32 of the transparent plate 31 may be constituted by a groove 41 extending along the four sides of a substantially square. With this configuration, the contact between the electrode F01 and the transparent plate 31 can be prevented. The section A02, which is an object, is disposed typically within the flat region surrounded by the groove 41, as shown in FIG. 13B.

The groove 41 of the transparent plate 31 may be used as a marker (or an alignment mark) indicating a location where the section A02 is placed. In this example, the groove 41 is formed at a position aligned with a position of the electrode F01, which is used for electrically connecting the image sensor B01 and the package 12 with each other. Accordingly, the section A02 is placed in the flat region formed at a position inward of the groove 41, and then, the transparent plate 31 and the image sensor unit are connected to each other so that the electrode F01 may be located within the groove 41. Then, the flat region formed at a position inward of the groove 41 opposes the front surface (imaging area) of the image sensor B01. That is, the section A02 placed in the flat region inward of the groove 41 can be located at a position at which it precisely opposes the front surface (imaging area) of the image sensor B01. In other words, it is possible to automatically position the section A02 on the front surface of the image sensor B01 without having to directly check the position of the imaging area of the image sensor B01. This makes it possible to facilitate the application of the CIS method.

The difference in the luminance (contrast) is generated in and near the groove 41. Accordingly, by detecting the contrast, the groove 41 can be detected with the human eye or a sensor.

The refractive index is different between air and glass. Accordingly, illumination light is refracted through the interface between air and glass. On the surface of the transparent plate 31, the structure of a flat portion 601 (see FIG. 13A) positioned outward of the groove 41 is uniform since the interface between air and glass is flat. Accordingly, in the flat portion 601, light is refracted uniformly through the interface between the transparent plate 31 and air. In contrast, the groove 41 has a wall extending in a direction perpendicular to the surface of the transparent plate 31. Accordingly, on the surface of the transparent plate 31, the traveling direction of light in a portion where the groove 41 is formed is different from that in the flat portion 601. That is, the luminance of the groove 41 may be different from that of the flat portion 601. Since the traveling of light in the groove 41 is more complicated than that in the flat portion 601, the groove 41 generally becomes darker than the flat portion 601. If the contrast of the groove 41 appears to be low, a color may be added to the groove 41.

Figure 11:
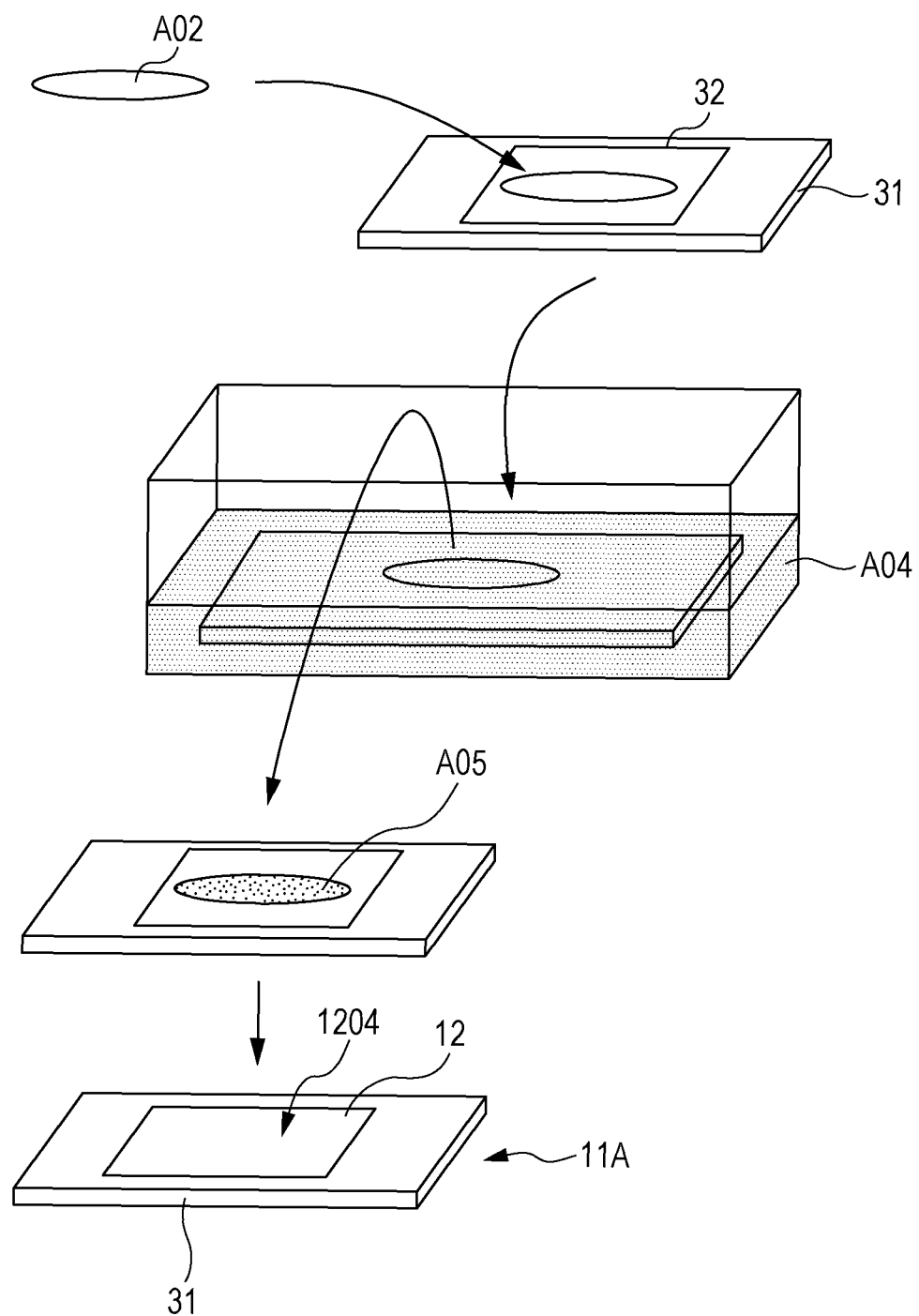
FIG. 11 is a view illustrating an example of a method for producing the preparation according to the second embodiment.

In order to stain the section A02, the transparent plate 31 is soaked in the stain solution A04, as shown in FIG. 11. If the soaking and/or removing of the transparent plate 31 in and from the stain solution A04 is automatically performed by a machine, it may be useful if the sizes of the transparent plates 31 are the same. The transparent plates (for example, slide glass) used in the embodiments of the present disclosure may be of a size similar to that of commercially available slide glass used for microscope examination. The transparent plate 31 shown in FIG. 14 may be of a size of regular slide glass (generally, 76 mm×26 mm).

Figure 14:
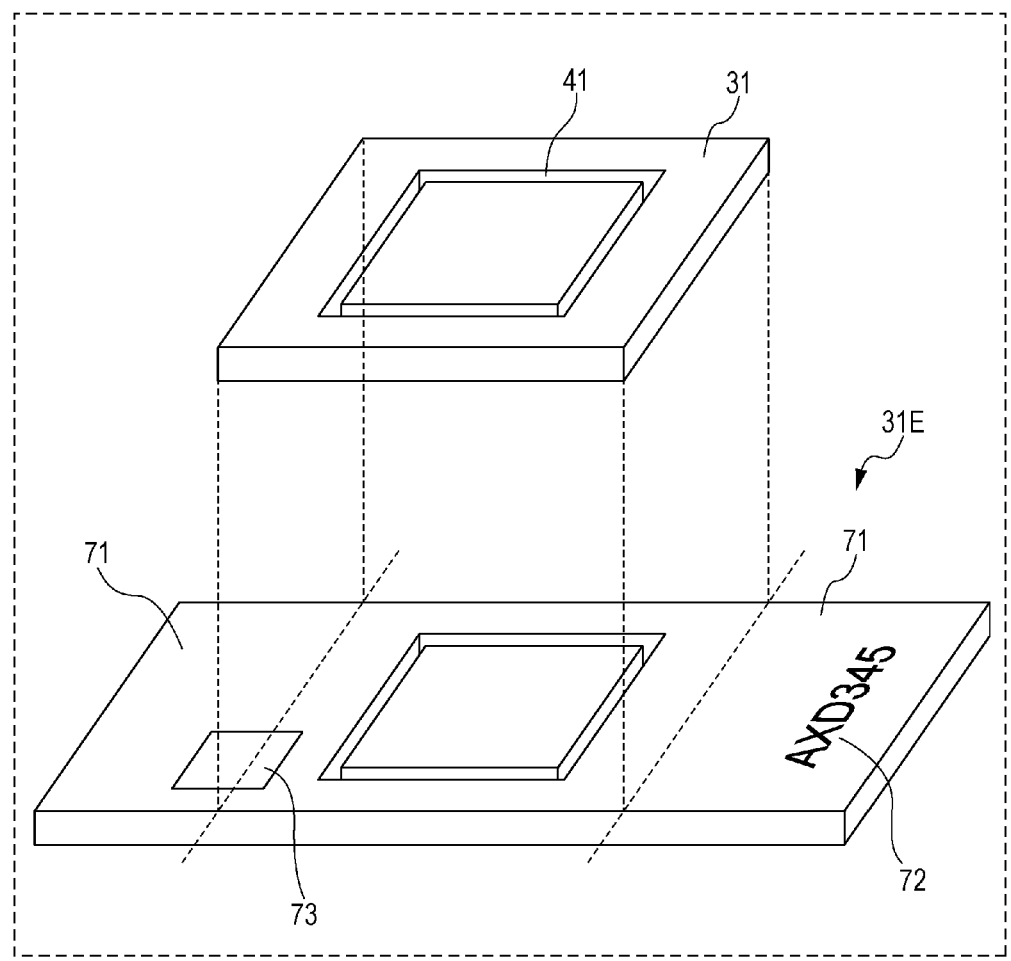
FIG. 14 is a perspective view illustrating a transparent plate having margins.

A transparent plate 31E shown in FIG. 14 has margins 71. Additional information such as a control number 72 ("AXD345" in the example shown in FIG. 14) may be written into the margins 71. The provision of the margins 71 is effective for enhancing user convenience. Additionally, as illustrated in FIG. 14, a memory 73 may be attached to the transparent plate (for example, slide glass). In the memory 73, information concerning a patient may be recorded digitally. In addition to the control number 72, all sorts of information concerning a patient may be recorded in a transparent plate in cooperation with electronic medical records of this patient. In this manner, a preparation (for example, the preparation 11A) may serve as a medium integrating total medical information concerning a patient corresponding to the stained section A05. The transparent plate 31E may be of a size of regular slide glass (generally, 76 mm×26 mm).

Specific examples of a method for integrating the package 12 having the image sensor B01 mounted thereon and the transparent plate 31 (slide glass in these examples) will be described below.

A method for fixing the transparent plate 31 to an image sensor unit including an image sensor and a package may include the following steps.

Figure 15:
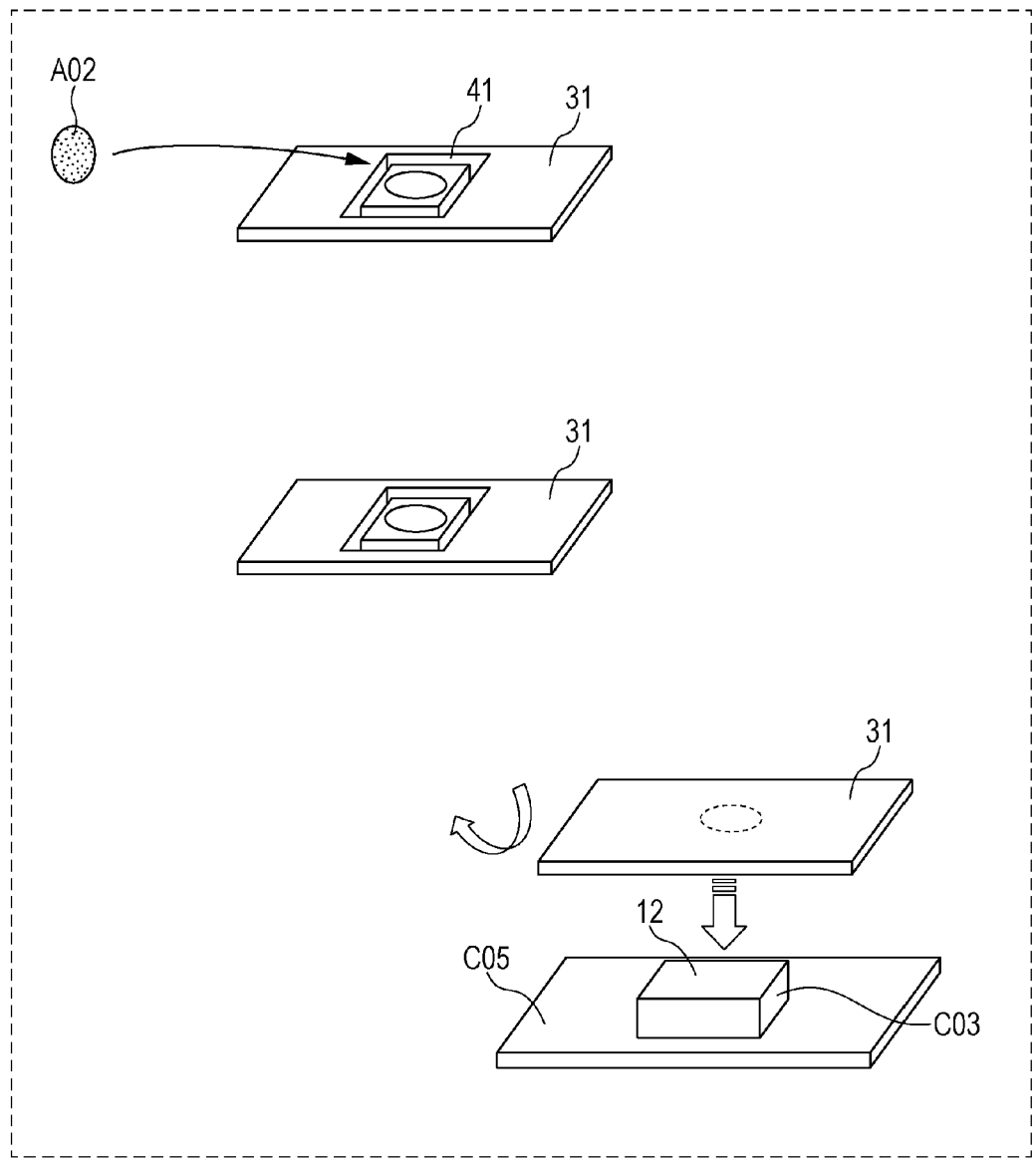
FIG. 15 is a perspective view illustrating an example of a method for fixing a transparent plate onto an image sensor unit including an image sensor and a package.

As shown in FIG. 15, the section A02 is first placed on the transparent plate 31, and is then extended and dried. Then, the transparent plate 31 is vertically inverted and is moved to a position at which it opposes the package 12 mounted on the socket C03 on the circuit board C05. Then, the transparent plate 31 is lowered, or the package 12 mounted on the socket C03 is lifted, thereby integrating the transparent plate 31 with the package 12.

Figure 16:
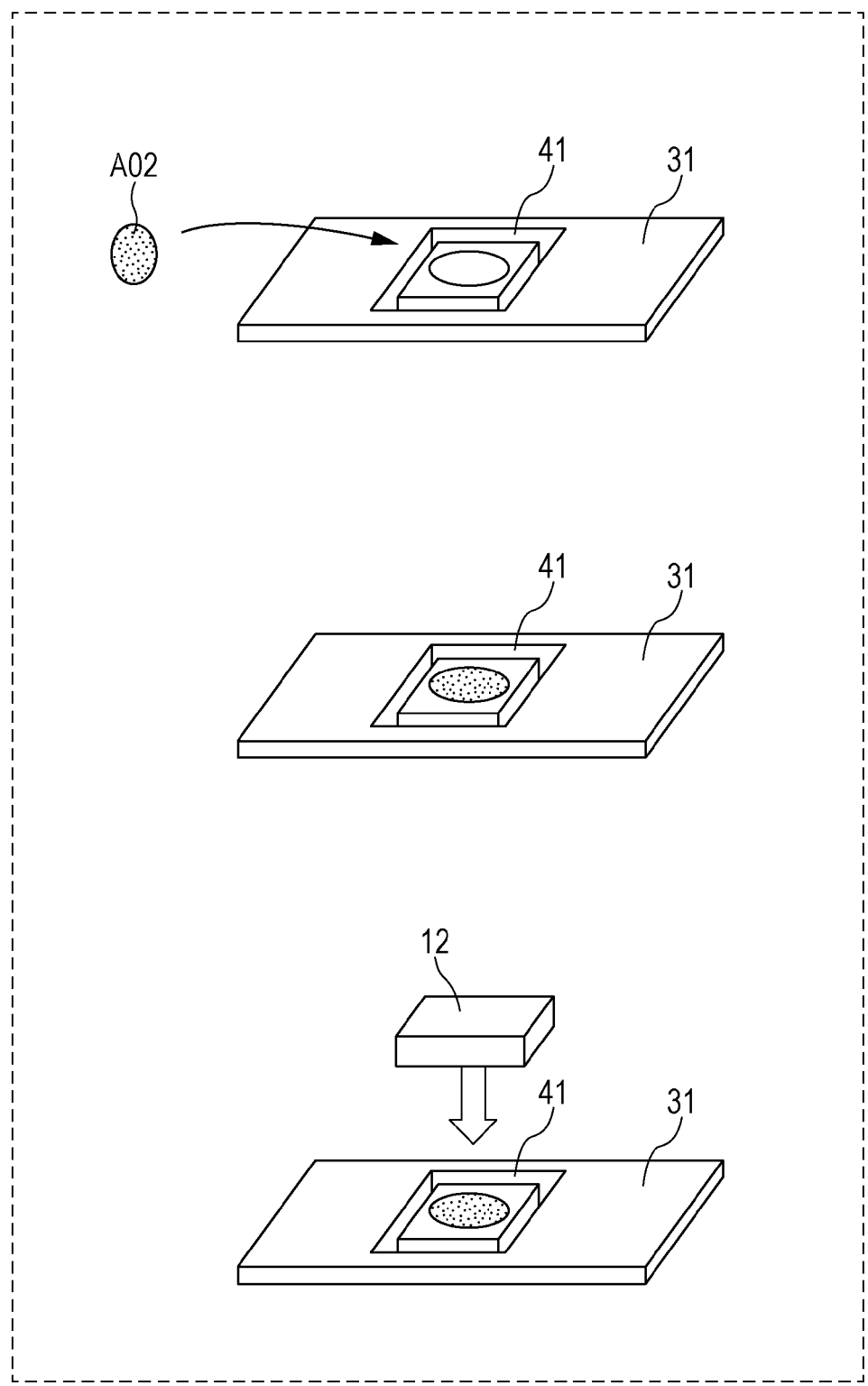
FIG. 16 is a perspective view illustrating another example of a method for fixing a transparent plate onto an image sensor unit including an image sensor and a package.

Alternatively, as shown in FIG. 16, the section A02 is first placed on the transparent plate 31, and is then extended and dried. Thereafter, the package 12 is moved to a position at which it opposes the section A02 on the transparent plate 31. Then, the package 12 is lowered, or the transparent plate 31 is lifted, thereby integrating the transparent plate 31 with the package 12.

Figure 17:
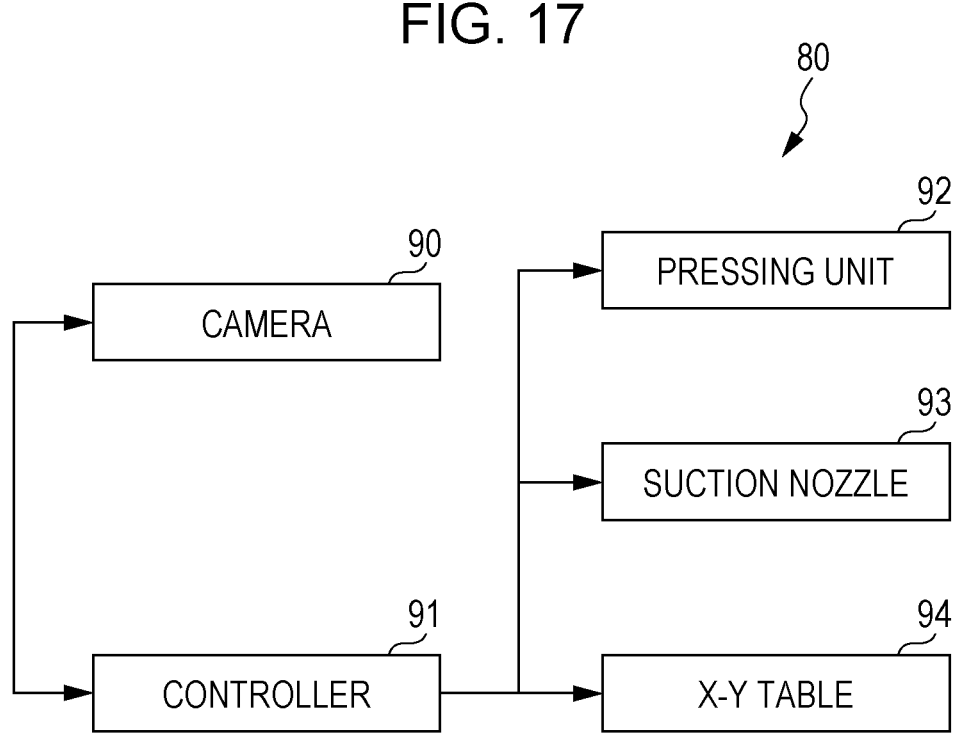
FIG. 17 is a block diagram schematically illustrating an example of the configuration of a preparation producing apparatus according to the second embodiment of the present disclosure.

FIG. 17 schematically illustrates an example of the configuration of a preparation producing apparatus 80 according to the second embodiment of the present disclosure.

As shown in FIG. 17, the preparation producing apparatus 80 includes a camera 90, a controller 91, a pressing unit 92, a suction nozzle 93, and an X-Y table 94.

The camera 90 acquires image information to be used for performing positioning between the package 12 and the transparent plate 31 by means of image recognition. The controller 91 controls the operations of the camera 90, the pressing unit 92, the suction nozzle 93, and the X-Y table 94 so that the transparent plate 31 can be appropriately fixed to the package 12.

The pressing unit 92 performs chucking of the back surface of the transparent plate 31 by using the suction nozzle 93. The pressing unit 92 holds the transparent plate 31 and, in this state, vertically moves the transparent plate 31. The pressing unit 92 may be a robot arm which is flexibly movable by using its plural joints. The X-Y table 94 is a table on which the circuit board C05 having the socket C03 mounted thereon is placed. For providing positioning, the X-Y table 94 is configured to movable in the X and Y directions in the horizontal plane at very small pitches.

Figure 18:
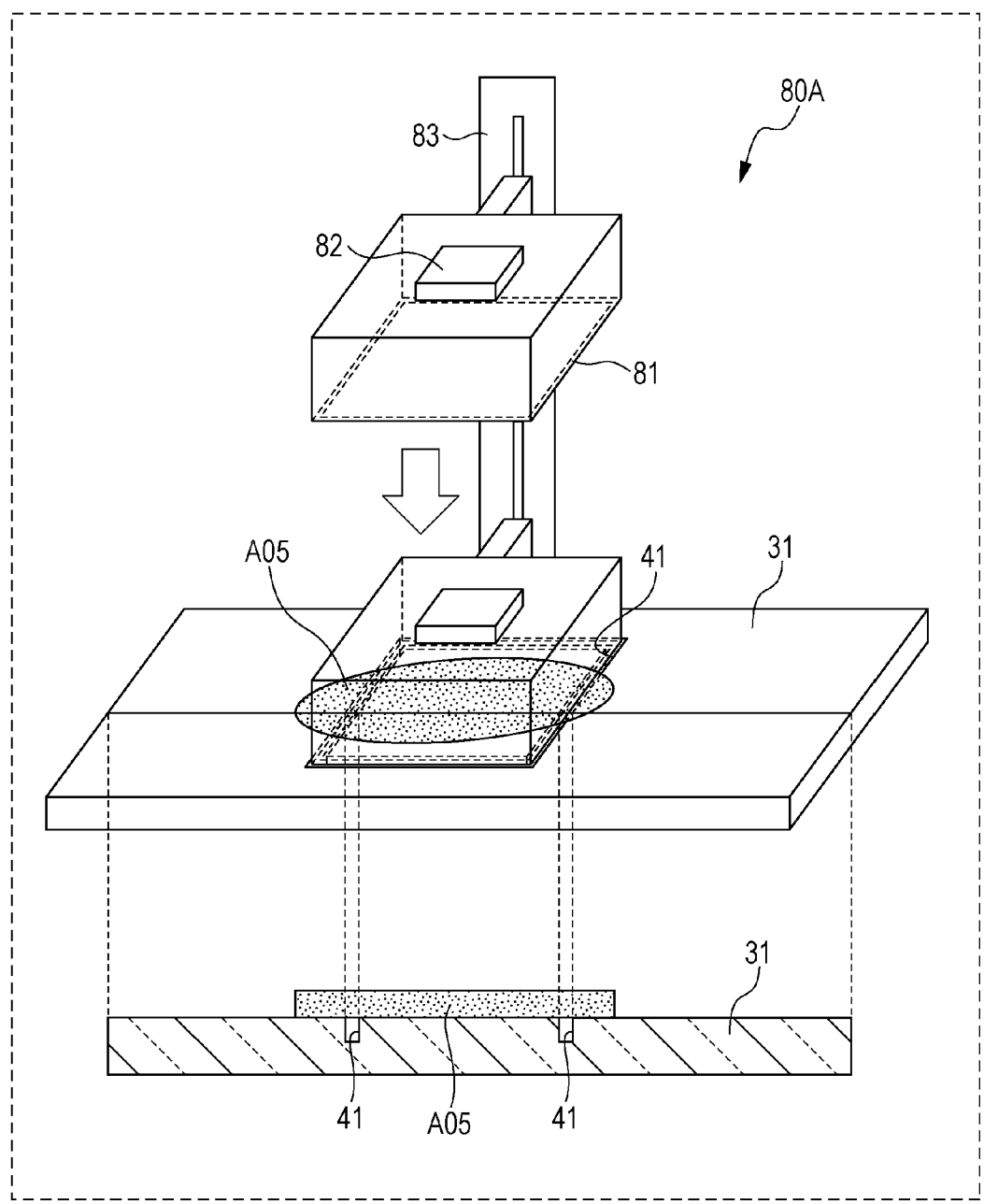
FIG. 18 is a schematic perspective view illustrating the major part of an example of a preparation producing apparatus.

FIG. 18 schematically illustrates the major part of an example of a preparation producing apparatus 80A having the above-described configuration. FIG. 18 also shows a schematic cross section of the transparent plate 31 disposed on the X-Y table 94 (not shown) included in the preparation producing apparatus 80A.

As described above, producing of a preparation may include a step of placing the section A02 on the transparent plate 31 and extending and drying the section A02. In this step, extending and drying of the section A02 may be performed in the state in which the section A02 is located in the flat region surrounded by the recessed portion 32 (in this case, the groove 41) of the transparent plate 31. That is, when placing the stained section A05 in the flat region surrounded by the groove 41, part of the stained section A05 may extend from the flat region to the outside of the groove 41. In such a situation, if the package 12 is fixed to the transparent plate 31, there may be a possibility that the stained section A05 contact the electrode F01 connected to the package 12. This may further cause short-circuiting or damage to the electrode F01.

In the preparation producing apparatus 80A according to an aspect of the second embodiment, if part of the stained section A05 extends from the flat region to the outside of the groove 41, the extending portion of the stained section A05 is cut off, thereby preventing the contact between the stained section A05 and the electrode F01.

The preparation producing apparatus 80A shown in FIG. 18 includes a cutter 81, a rail 83, and a camera 82. The rail 83 supports the cutter 81 so that the cutter 81 may be vertically movable. The layout of the cutter 81 matches that of the groove 41 in the transparent plate 31. More specifically, as in the example shown in FIG. 18, the groove 41 extends along the four sides of the substantially square flat region of the transparent plate 31, and the edge of the cutter 81 matches the shape of the groove 41 when the cutter 81 contacts the transparent plate 31.

The transparent plate 31 is placed on the X-Y table 94 (not shown in FIG. 18) of the preparation producing apparatus 80A. As a result of the X-Y table 94 inching at very small pitches in the horizontal plane, the transparent plate 31 is shifted to a position almost right under the cutter 81. Then, the cutter 81 is shifted downward in the vertical direction along the rail 83 toward the stained section A05. At this time, the position of the transparent plate 31 on the X-Y table 94 is detected by the camera 82. If necessary, the X-Y table 94 shifts to make fine adjustments to the position of the groove 41 of the transparent plate 31 with respect to the position of the cutter 81. The above-described camera 90 (see FIG. 17) may also serve as the camera 82 of the preparation producing apparatus 80A. That is, the preparation producing apparatus 80A may not necessarily include two or more cameras.

When the cutter 81 shifting downward along the rail 83 reaches the groove 41 of the transparent plate 31, it contacts the stained section A05. Then, part of the stained section A05 extending to the outside of the groove 41 is cut off by using the cutter 81. This step is performed prior to a step of fixing the transparent plate 31 to the image sensor B01 and the package 12.

In the second embodiment, it is possible to prevent the stained section A05 from contacting the electrode F01 connected to the package 12.

Third Embodiment

Figure 19:
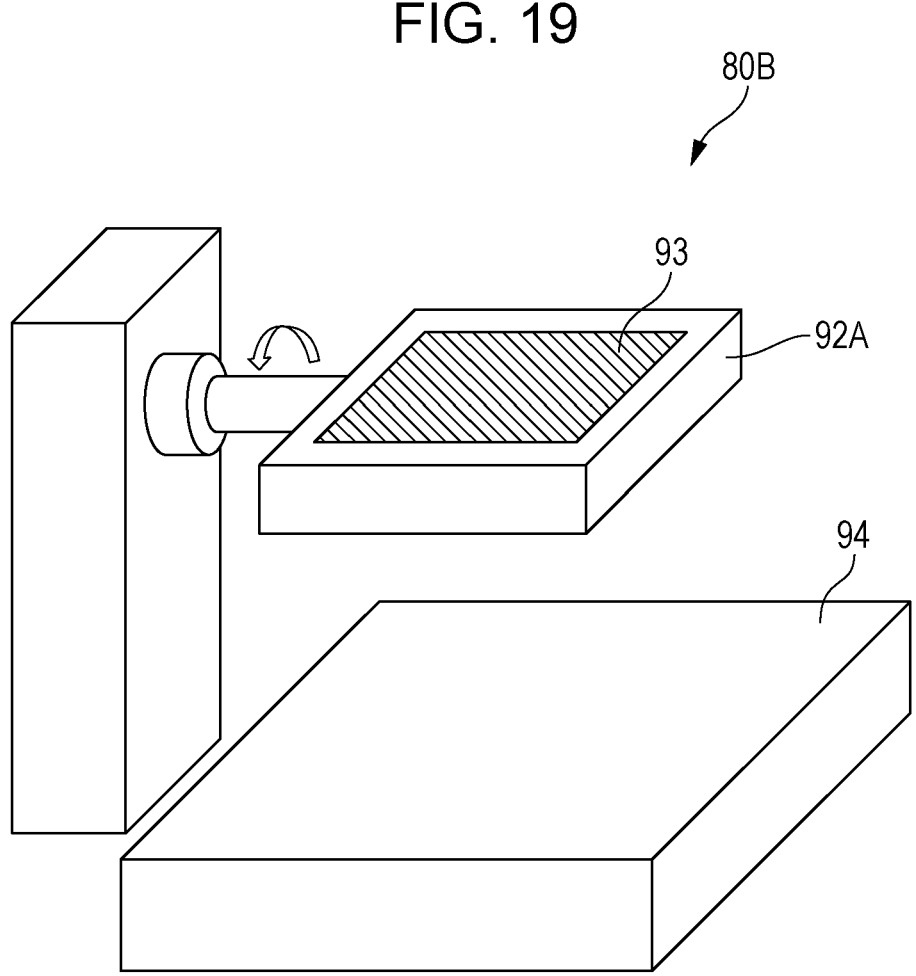
FIG. 19 is a schematic perspective view illustrating the major part of an example of a preparation producing apparatus according to a third embodiment of the present disclosure.

FIG. 19 schematically illustrates the major part of a preparation producing apparatus 80B according to a third embodiment of the present disclosure. In the preparation producing apparatus 80B shown in FIG. 19, a pressing unit 92A includes a mechanism which is rotatable around a shaft extending in the horizontal direction. The provision of this mechanism makes it possible to vertically invert the transparent plate 31 (not shown in FIG. 19) chucked by the suction nozzle 93. By using the preparation producing apparatus 80B shown in FIG. 19, the method discussed with reference to FIG. 15 can be realized.

The use of the preparation producing apparatus 80B also makes it possible to realize the method discussed with reference to FIG. 16. In this case, the transparent plate 31 (not shown in FIG. 19) is placed on the X-Y table 94, and the package 12 having the image sensor B01 connected thereto is held to the pressing unit 92A by the suction nozzle 93. The configuration illustrated in FIG. 19 may be combined with that illustrated in FIG. 18.

Fourth Embodiment

As discussed with reference to FIG. 12, in the above-described preparation 11A, the position of the outer edge of the side wall 34 of the package 12 is aligned with the position of the inner wall 501 of the recessed portion 32 of the transparent plate 31. As described above, however, it is not always necessary that the position of the outer edge of the side wall 34 of the package 12 exactly match the position of the inner wall 501 of the recessed portion 32 of the transparent plate 31, and there may be a gap therebetween. Even if there is a gap, the range of the horizontal motion of the package 12 may be restricted by the inner wall 501 of the transparent plate 31.

Figure 20:
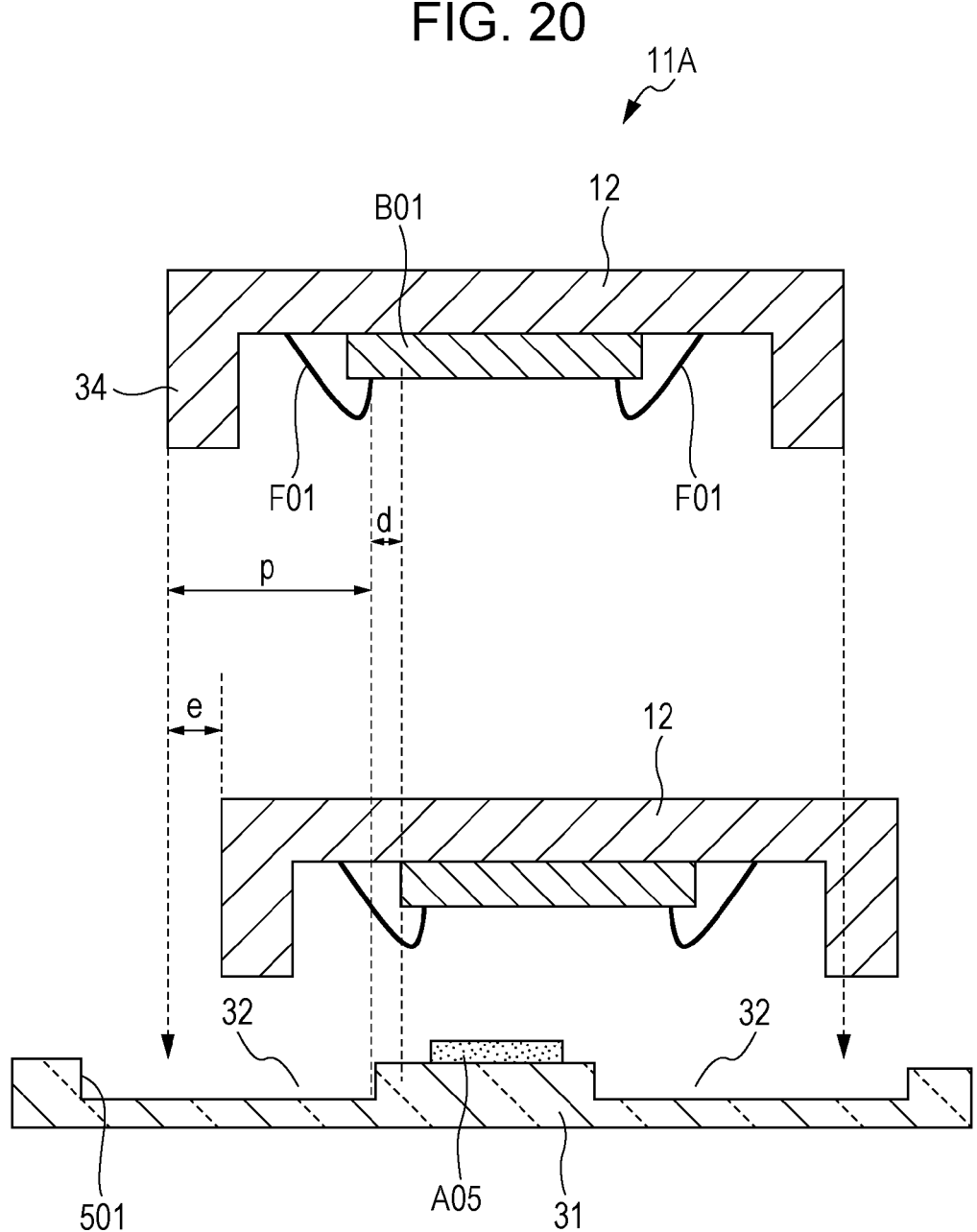
FIG. 20 is a schematic sectional view illustrating an example of the preparation in which a gap between the outer edge of the side wall of the package and the inner wall of the recessed portion of the transparent plate is too large.

FIG. 20 illustrates an example of the preparation 11A in which the above-described gap is too large. In the example shown in FIG. 20, since the range of the horizontal motion of the package 12 is too large, there may be a possibility that the position of the electrode F01 be displaced from the recessed portion 32 of the transparent plate 31. In the example shown in FIG. 20, the package 12 (shown in the lower side of FIG. 20) is shifted from the package 12 (shown in the upper side of FIG. 20) located at a horizontally suitable position to the right side of FIG. 20 by a distance e. In this case, if this package 12 is lowered without changing its position, the electrode F01 may strike the transparent plate 31.

Figure 21:
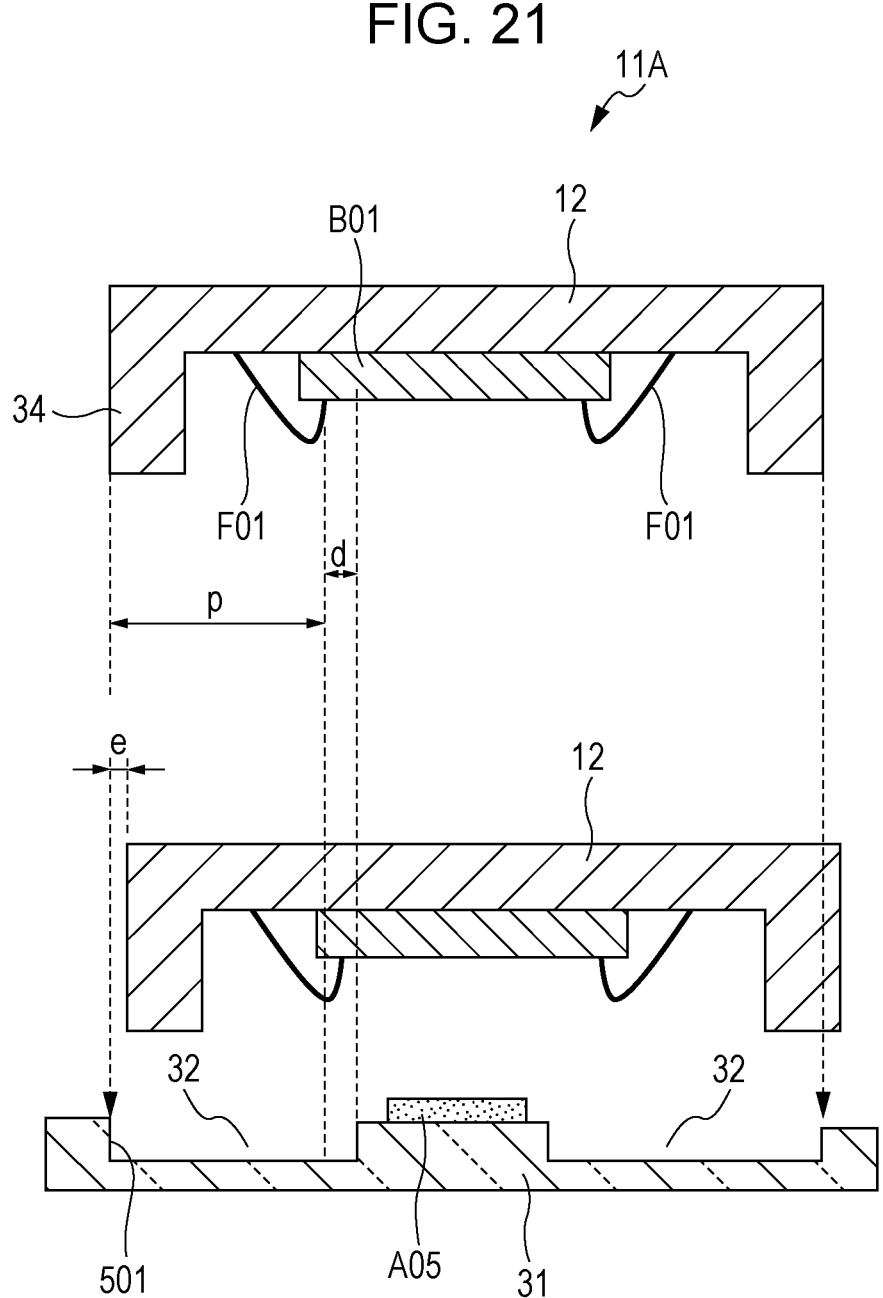
FIG. 21 is a schematic sectional view illustrating an example of the preparation in which a gap between the outer edge of the side wall of the package and the inner wall of the recessed portion of the transparent plate is too small.

In contrast, FIG. 21 illustrates an example of the preparation 11A in which the above-described gap is too small. In the example shown in FIG. 21, since the range of the horizontal motion of the package 12 is too small, the position of the outer edge of the side wall 34 of the package 12 may be displaced from the recessed portion 32 of the transparent plate 31. In the example shown in FIG. 21, the package 12 (shown in the lower side of FIG. 21) is shifted from the package 12 (shown in the upper side of FIG. 21) located at a horizontally suitable position to the right side of FIG. 21 by a distance e. In this case, if this package 12 is lowered without changing its position, the side wall 34 may strike the transparent plate 31.

Considering the above-described situations, the position and the width of the recessed portion 32 is suitably determined by allowing a necessary margin, so that the transparent plate 31 may not strike the side wall 34 or the electrode F01 connected to the package 12 even if the package 12 is shifted by a distance e.

Fifth Embodiment

In a fifth embodiment, a transparent plate is configured to squeeze out air bubbles within a mounting medium when it is integrated with a package. In the fifth embodiment, it is also possible to let out air from a space formed between the transparent plate and the package, which will be discussed below.

Figure 22:
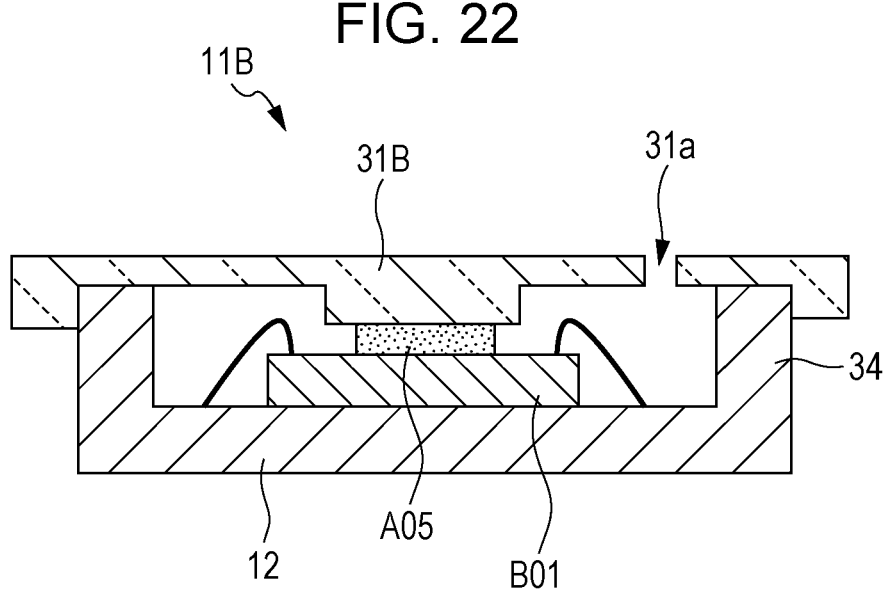
FIG. 22 is a schematic sectional view illustrating a transparent plate according to a fifth embodiment of the present disclosure.

Reference will first be given to FIG. 22. As illustrated in FIG. 22, a transparent plate 31B of a preparation 11B has an opening 31a used for communicating a space formed between the transparent plate 31B and the package 12 with the outside. The opening 31a serves as an air releasing hole. The opening 31a may be provided in the package 12.

Figure 23:
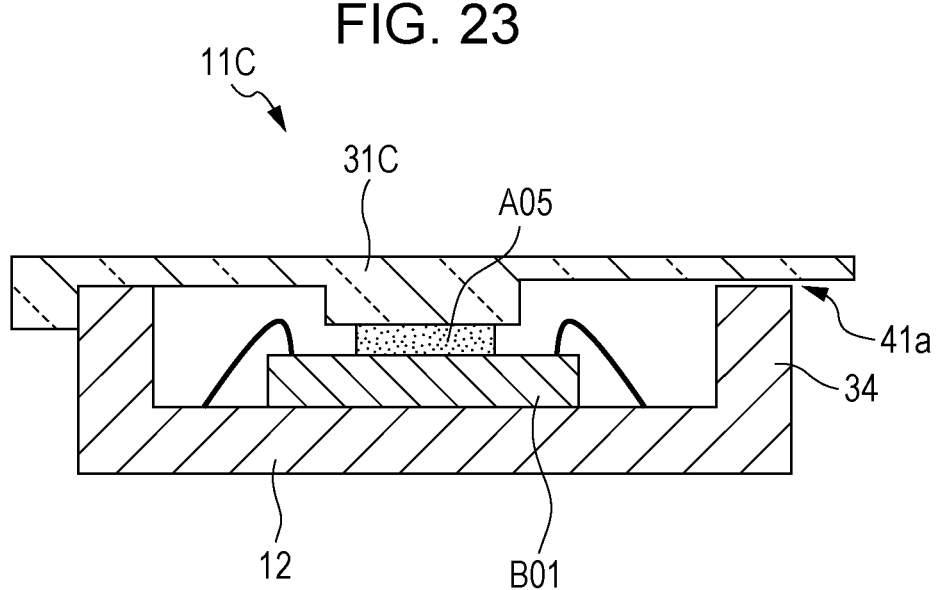
FIG. 23 is a schematic sectional view illustrating another transparent plate according to the fifth embodiment of the present disclosure.

Reference will now be given to FIG. 23. As illustrated in FIG. 23, a transparent plate 31C of a preparation 11C has a groove 41a used for communicating a space formed between the transparent plate 31C and the package 12 with the outside. The groove 41a serves as an air releasing hole.

Figure 24:
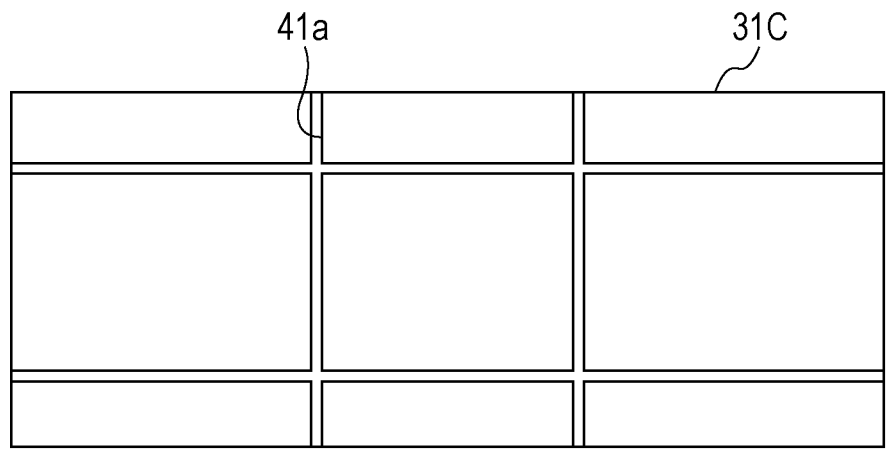
FIG. 24 is a top view illustrating the transparent plate according to the fifth embodiment of the present disclosure.

FIG. 24 is a top view of the transparent plate 31C on which the above-described groove 41a is formed. In this example, at least two grooves 41a extending from one end to the other end of the transparent plate 31C are provided. Each groove 41a extends from one end to the other end of the transparent plate 31C. In the example shown in FIG. 24, four linear grooves 41a are formed on the transparent plate 31C. A section A02 (not shown in FIG. 24) is placed in a substantially square region surrounded by the four grooves 41a. In the grooves 41a, the portions extending along this square region serve as the above-described recessed portions 32 for receiving the side walls 34 of the package 12 and the electrodes F01.

For example, if the electrodes F01 for connecting the image sensor B01 and the package 12 are disposed along two opposing sides among the four sides of the front surface of the image sensor B01, two parallel grooves may be provided on a transparent plate (for example, slide glass).

Sixth Embodiment

Figure 25:
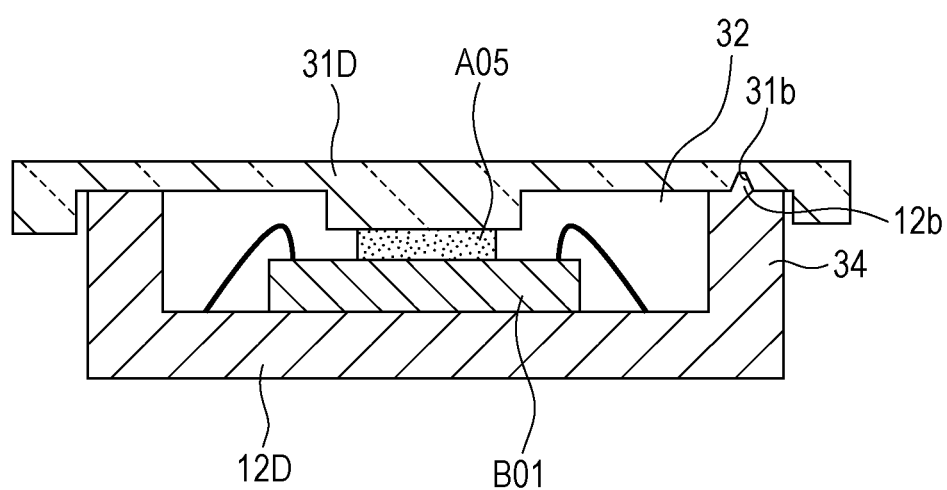
FIG. 25 is a schematic sectional view illustrating a transparent plate according to a sixth embodiment of the present disclosure.

If the position of the outer edge of the side wall of a package is not aligned with the position of the inner wall of the recessed portion of a transparent plate, a transparent plate 31D having a notch 31b for positioning a package may be used, as in a preparation 11D illustrated in FIG. 25. In this case, as shown in FIG. 25, a package 12D having a projecting portion 12b which is engaged with the notch 31b of the transparent plate 31D may be used. The projecting portion 12b is formed, for example, at the forward end of the side wall 34 of the package 12D. The shape of the projecting portion 12b is designed so as to match the shape of the notch 31b.

According to the embodiments of the present disclosure, it is possible to change the viewpoint and/or the resolution while performing examination without changing the lens or moving the transparent plate. With this configuration, it is possible to apply the embodiments of the above-described imaging apparatus to a specimen management apparatus.

An embodiment of a specimen management apparatus implemented by using the above-described imaging apparatus will be described below.

Seventh Embodiment

Figure 26:
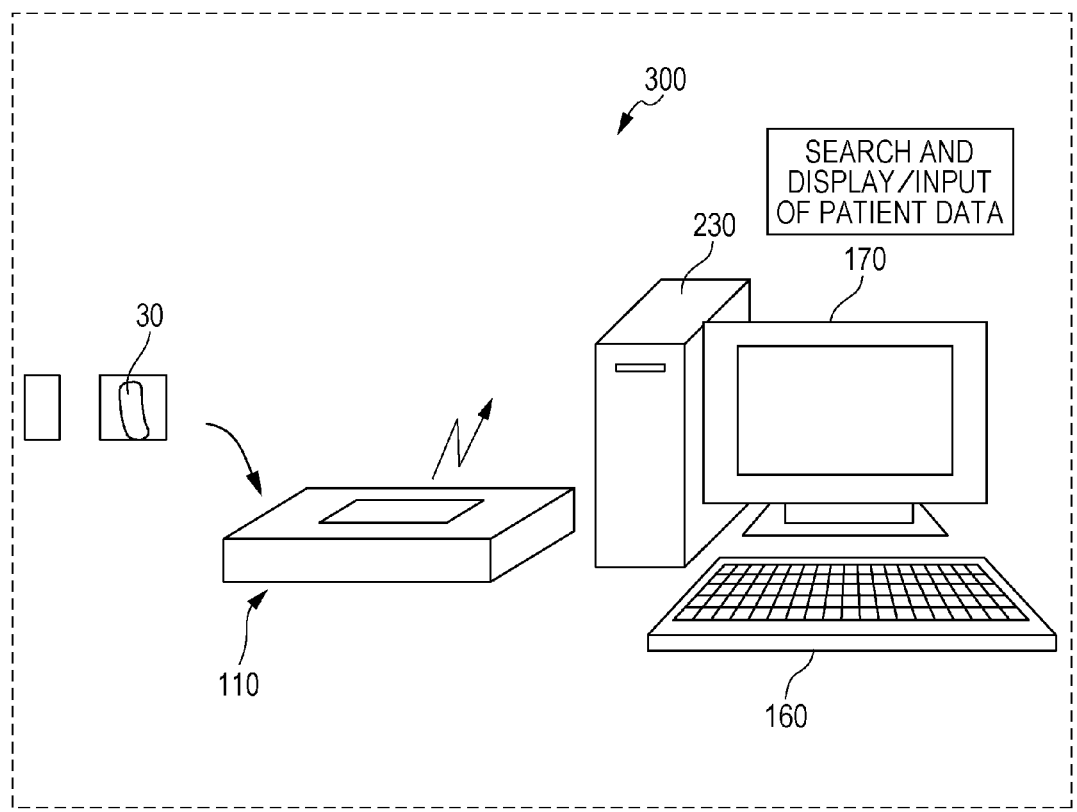
FIG. 26 is a view illustrating an example of the overall configuration of a specimen management apparatus according to a seventh embodiment of the present disclosure.

FIG. 26 illustrates an example of the overall configuration of a specimen management apparatus 300 according to a seventh embodiment.

As shown in FIG. 26, the specimen management apparatus 300 includes a specimen image acquiring device 110 and an information processing device 230. The specimen image acquiring device 110 may be the imaging apparatus 10 discussed with reference to FIG. 6 or the imaging apparatus 10A discussed with reference to FIG. 8. By using the preparation of one of the above-described embodiments (for example, the preparation 11), the specimen image acquiring device 110 is able to acquire an image of a pathology specimen 30 at a specified one of plural magnifications (resolution levels).

The information processing device 230 is connected to the specimen image acquiring device 110 via a wired or wireless medium. The information processing device 230 receives information acquired by the specimen image acquiring device 110. The information processing device 230 calculates the feature quantity of the image of the pathology specimen 30 acquired by the specimen image acquiring device 110, and, on the basis of the calculated feature quantity, the information processing device 230 outputs patient information corresponding to the pathology specimen 30 to an output device 170. More specifically, the information processing device 230 refers to a database in which feature quantities calculated from specimen images obtained from patients are associated with plural items of patient information, and then searches for an item of patient information that is associated with the feature quantity of the image of the pathology specimen 30.

The information processing device 230 shown in FIG. 26 is connected to an input device 160 and the output device 170. The information processing device 230 has functions similar to those of the control PC C06 discussed with reference to FIG. 6. The input device 160 is a device used by a user to input data or an instruction into the information processing device 230. Examples of the input device 160 are a keyboard, a mouse, and a touch screen. Examples of the output device 170 are a display which displays images and/or characters, a printer, and a speaker. The input device 160 and the output device 170 may be a device integrating a touch screen and a display. If the specimen management apparatus 300 includes the input device 160 and the output device 170, the imaging apparatus serving as the specimen image acquiring device 110 may not necessarily include the control PC C06 and the display C07.

If an item of patient information that is associated with the feature quantity of the image of the pathology specimen 30 is included in the database, the information processing device 230 outputs this item of patient information to the output device 170. If plural items of patient information that are associated with the feature quantity of the image of the pathology specimen 30 are included in the database, the information processing device 230 first acquires an image of higher resolution than the resolution of the previously acquired image, and then searches the database for patient information that is associated with the feature quantity of the higher resolution image. If patient information that is associated with the feature quantity of the image is not included in the database, the information processing device 230 receives input of patient information from the input device 160, and stores the patient information in the database in association with the feature quantity calculated from the image. In this case, the specimen image acquiring device 110 acquires an image of higher resolution than the resolution of the previously acquired image, and the information processing device 230 stores the feature quantity calculated from each of the acquired images in the database in association with the patient information.

Figure 27:
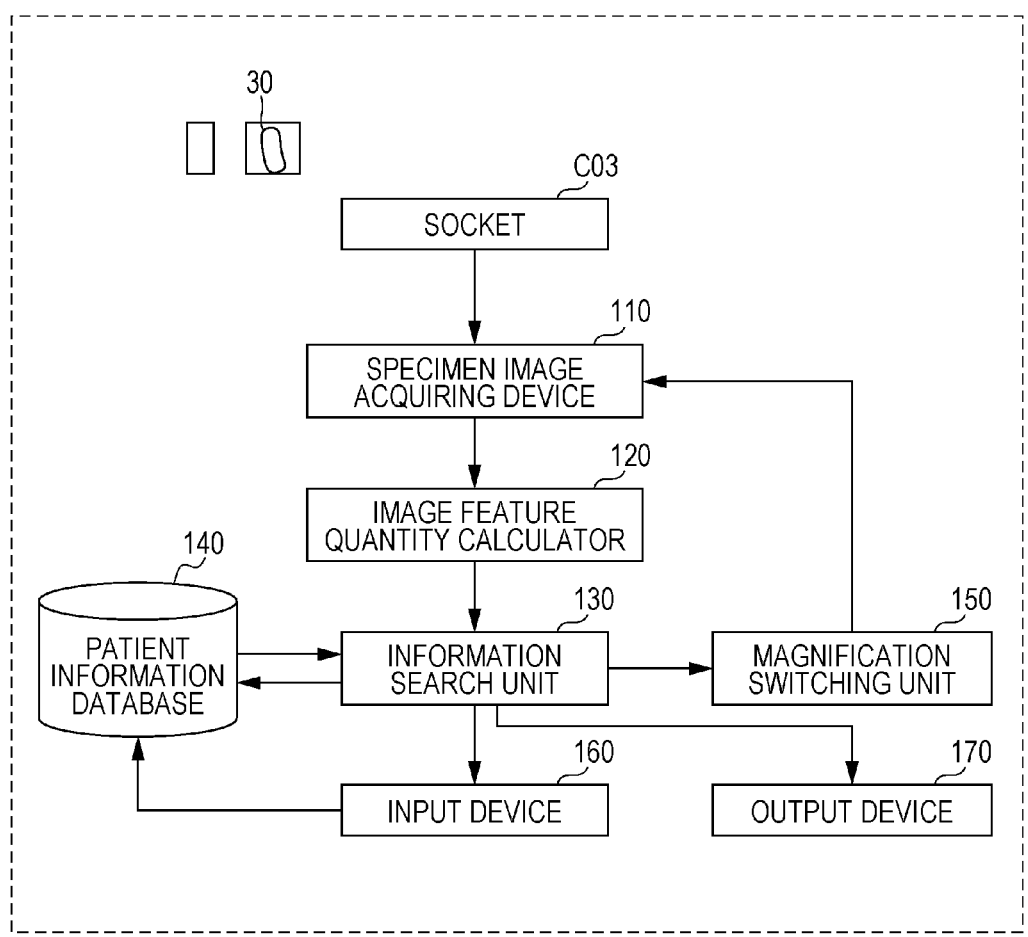
FIG. 27 is a block diagram illustrating an example of the configuration of the specimen management apparatus according to the seventh embodiment of the present disclosure.

FIG. 27 is a block diagram illustrating an example of the specimen management apparatus according to the seventh embodiment. In the example shown in FIG. 27, the specimen management apparatus includes the socket C03, the specimen image acquiring device 110, an image feature quantity calculator 120, an information search unit 130, a patient information database (hereinafter simply referred to as the "database") 140, a magnification switching unit 150, the input device 160, and the output device 170.

A pathology specimen 30 from which patient information will be obtained or updated is placed on the socket C03. As the pathology specimen 30, the preparation including an object fixed therein according to one of the above-described embodiments may be used. Here, the preparation 11 including an object fixed therein will be discussed as the pathology specimen 30 by way of example.

The specimen image acquiring device 110 captures an image of a specimen (in this case, the stained section A05) included in the preparation 11 by using one of predetermined different magnifications. The image feature quantity calculator 120 calculates the feature quantity from the image acquired by the specimen image acquiring device 110. The information search unit 130 refers to the database 140 in which plural items of patient information and image feature quantities are stored in association with each other, and then searches for patient information corresponding to an image feature quantity in the database 140 that matches the image feature quantity calculated by the image feature quantity calculator 120. If there are plural items of patient information are obtained as a result of a search conducted by the information search unit 130, the magnification switching unit 150 switches the magnification to a higher factor (higher resolution level), and then, the specimen image acquiring device 110 captures an image again. Then, the information search unit 130 conducts a search again based on information obtained with the higher magnification (higher resolution level).

If patient information associated with the calculated image feature quantity is not found in the database 140, the input device 160 receives input of patient information, assuming that the preparation 11 is a specimen obtained from a new patient. If patient information associated with the calculated image feature quantity is found in the database 140, the output device 170 outputs the obtained patient information.

The operations and configurations of the components in the seventh embodiment will be described below in detail.
[Operation of Specimen Management Apparatus]

Figure 28:
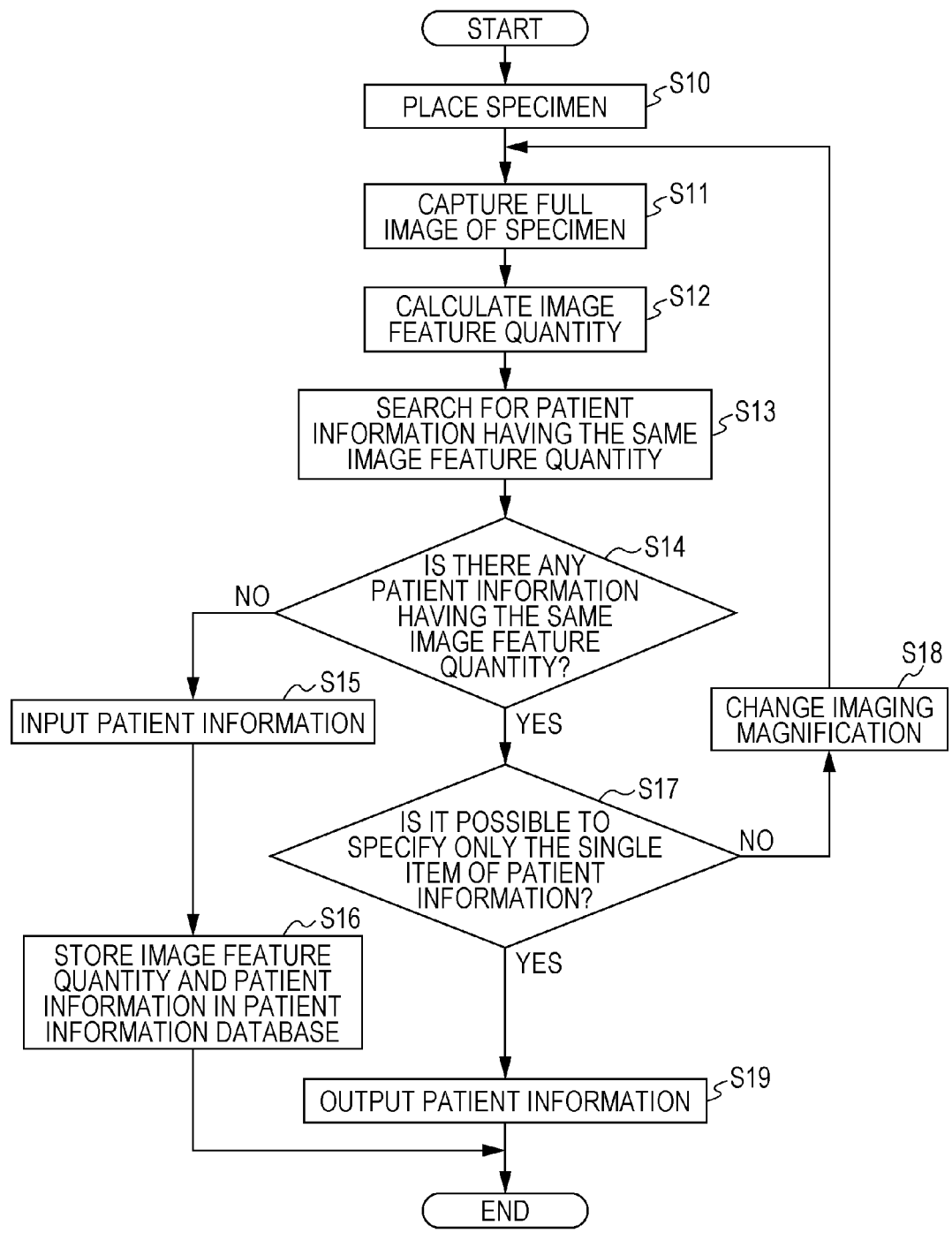
FIG. 28 is a flowchart illustrating an example of specimen management processing according to the seventh embodiment of the present disclosure.

Reference will first be given to FIG. 28. FIG. 28 is a flowchart illustrating an example of specimen management processing.

In step S10, the preparation 11, which is a specimen from which patient information will be obtained or updated, is placed on the socket C03. As described above, the socket C03 is configured to mount the preparation 11 thereon. The socket C03 has a recessed portion of a size of which the pathology specimen 30 can be stored. By using this socket C03, a positional displacement of the pathology specimen 30 when capturing an image of the pathology specimen 30 can be suppressed. In Japan, a pathology specimen of a size of 76 mm×26 mm defined by the standards is generally used. The socket C03 may be formed in a shape in which the pathology specimen 30 of this size can be set. By mounting the preparation 11 on the socket C03 (see FIG. 27) of the imaging apparatus, the image sensor B01 and the socket C03 are electrically connected to each other via terminals (plural first terminals 1205 or plural second terminals 1206 shown in FIG. 6) of the package 12 of the preparation 11.

Figure 29:
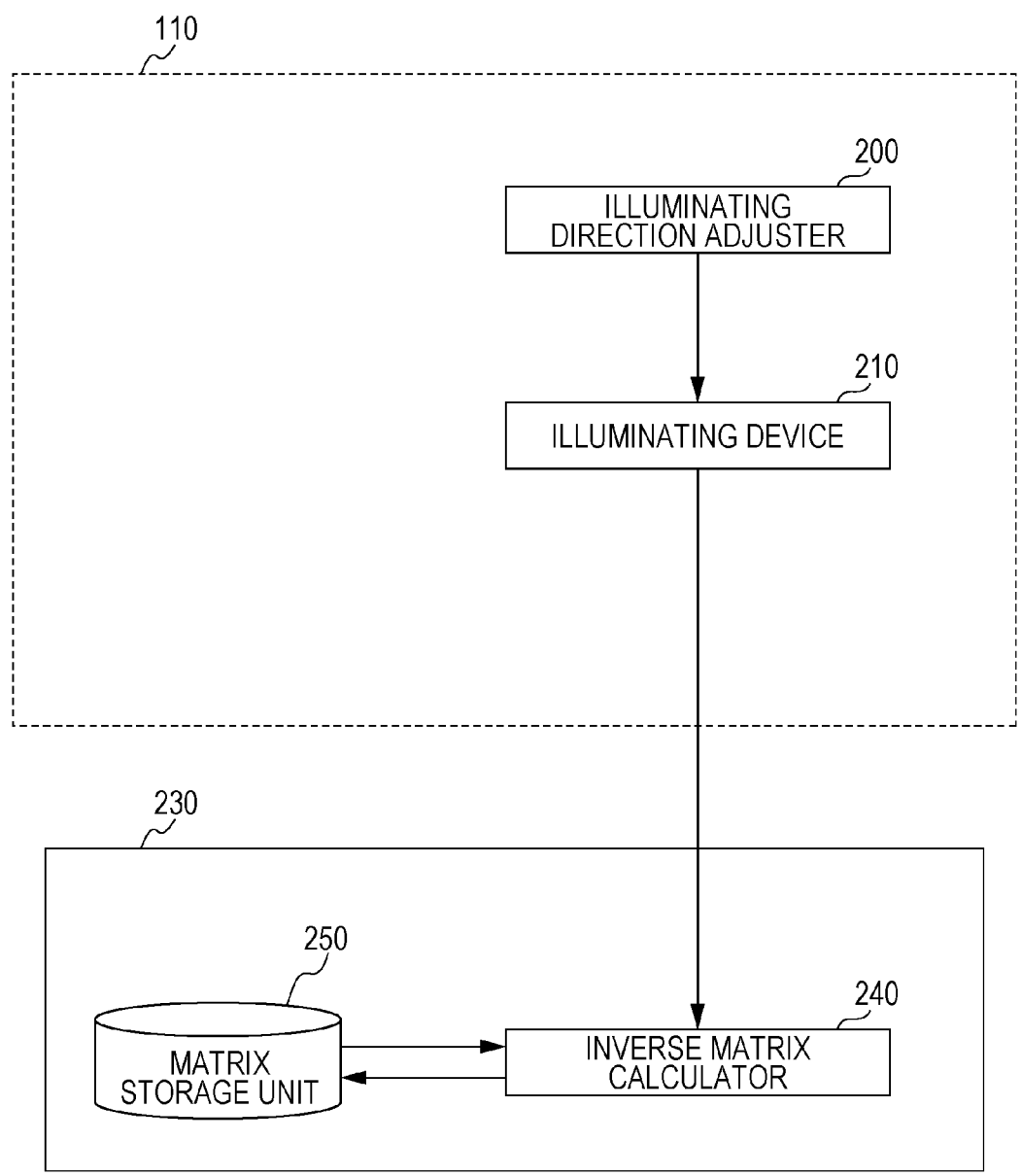
FIG. 29 is a block diagram illustrating an example of the configuration of a specimen image acquiring device according to the seventh embodiment of the present disclosure.

In step S11, the specimen image acquiring device 110 acquires an image of the pathology specimen 30 by using one of the predetermined different magnifications. FIG. 29 is a block diagram illustrating an example of the configuration of the specimen image acquiring device 110. In the example shown in FIG. 29, the specimen image acquiring device 110 includes an illuminating direction adjuster 200 and an illuminating device 210. The illuminating device 210 is an example of the above-described light source unit C09. The illuminating device 210 includes, for example, a light source G01 which emits light to be incident on the image sensor B01 of the preparation 11. The specimen image acquiring device 110 acquires an image of a specimen (for example, a full image of the specimen) by using a certain magnification specified by the information processing device 230.

When acquiring an image of a different magnification, the resolution can be increased by using an inverse matrix calculator 240 and a matrix storage unit 250. The inverse matrix calculator 240 and the matrix storage unit 250 may be provided within the information processing device 230, as illustrated in FIG. 29, or one or both of the inverse matrix calculator 240 and the matrix storage unit 250 may be provided within the specimen image acquiring device 110. Details of the operation of the inverse matrix calculator 240 and the matrix storage unit 250 will be discussed later.

Figure 30:
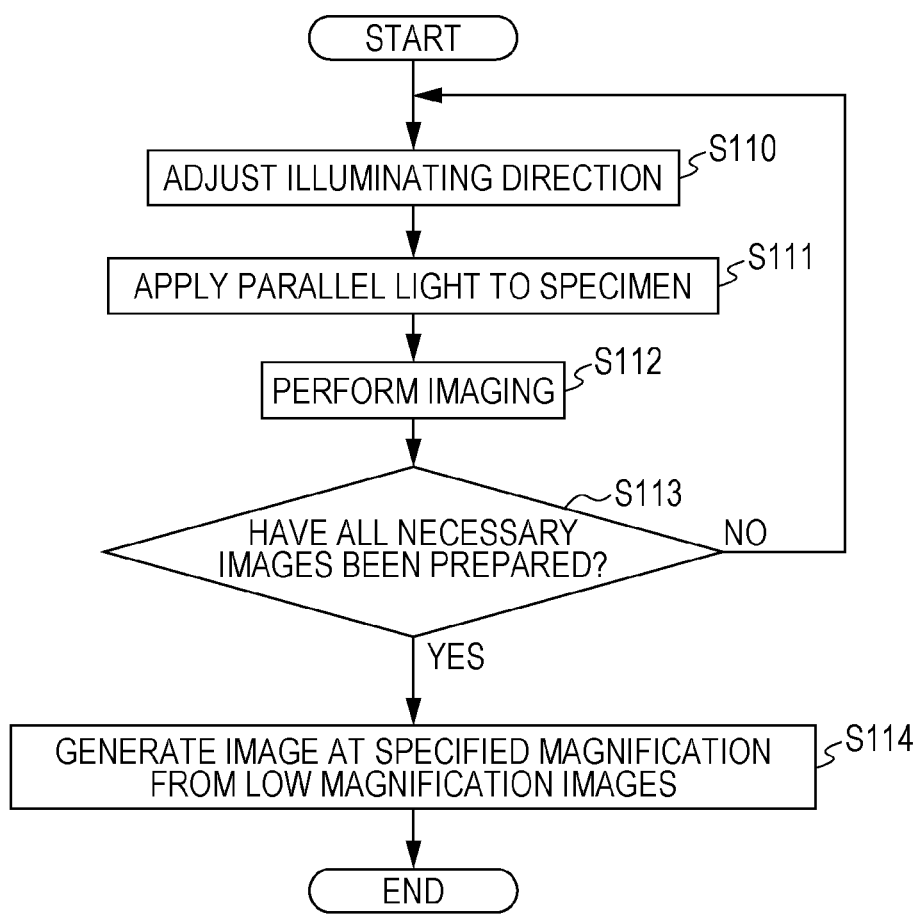
FIG. 30 is a flowchart illustrating an example of the operation of the specimen image acquiring device according to the seventh embodiment of the present disclosure.

An example of image acquiring processing in the seventh embodiment will be described below with reference to FIG. 30.

Figure 31A:
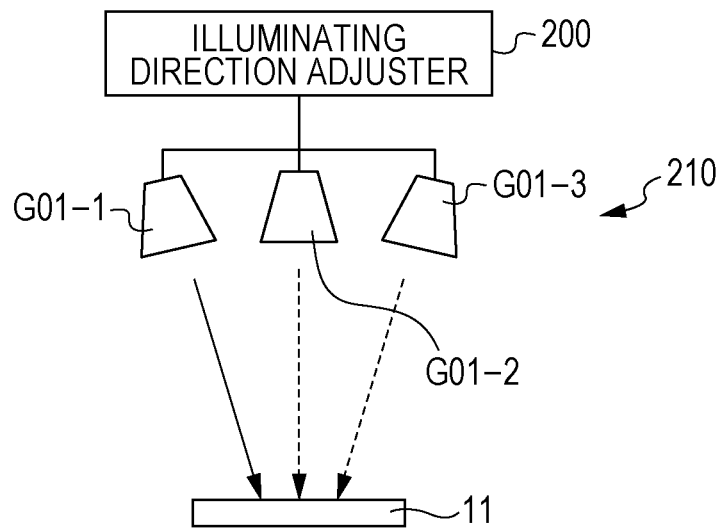
FIG. 31A is a schematic view illustrating an example of the configuration of an illuminating device according to the seventh embodiment of the present disclosure.
Figure 31B:
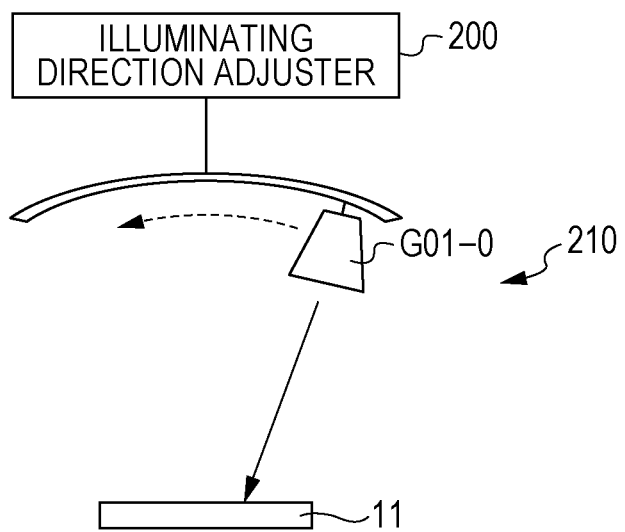
FIG. 31B is a schematic view illustrating another example of the configuration of the illuminating device according to the seventh embodiment of the present disclosure.

In step S110, the angle of incidence of illumination light (typically, parallel light) to be applied to the pathology specimen 30 is adjusted by the illuminating direction adjuster 200 (see FIGS. 31A and 31B). For adjusting the illuminating direction, as shown in FIG. 31A, plural light sources (light sources G01-1, G01-2, and G01-3 in the example shown in FIG. 31A) may be installed in the light source unit C09 (not shown in FIG. 31A) so that light can be applied at predetermined angles. Alternatively, a single light source (light source G01-0 in the example shown in FIG. 31B) installed in the light source unit C09 (not shown in FIG. 31B) may be shifted at a specified angle, as shown in FIG. 31B.

Figure 32A:
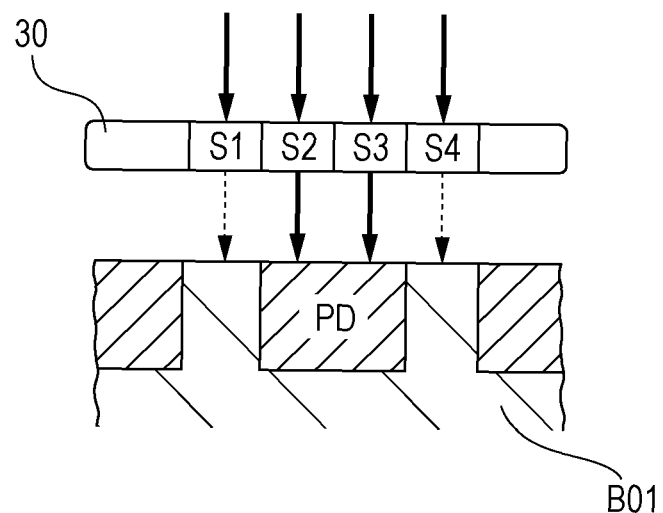
FIG. 32A is a schematic view illustrating an example of the operation (changing of the illuminating direction) of the specimen image acquiring device according to the seventh embodiment of the present disclosure.
Figure 32B:
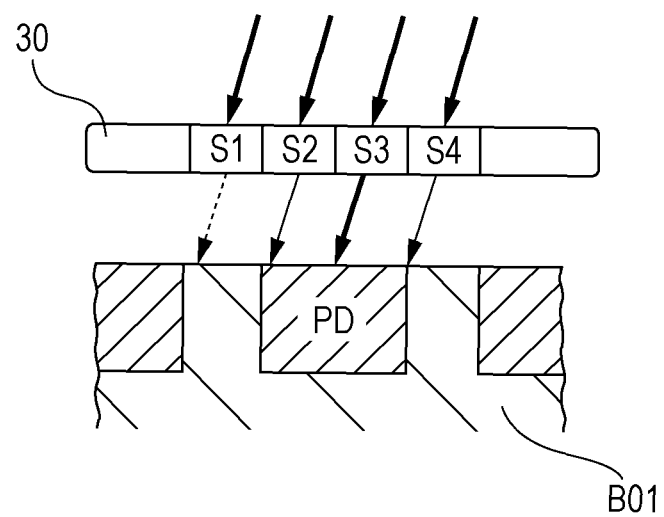
FIG. 32B is a schematic view illustrating another example of the operation (changing of the illuminating direction) of the specimen image acquiring device according to the seventh embodiment of the present disclosure.
Figure 33:
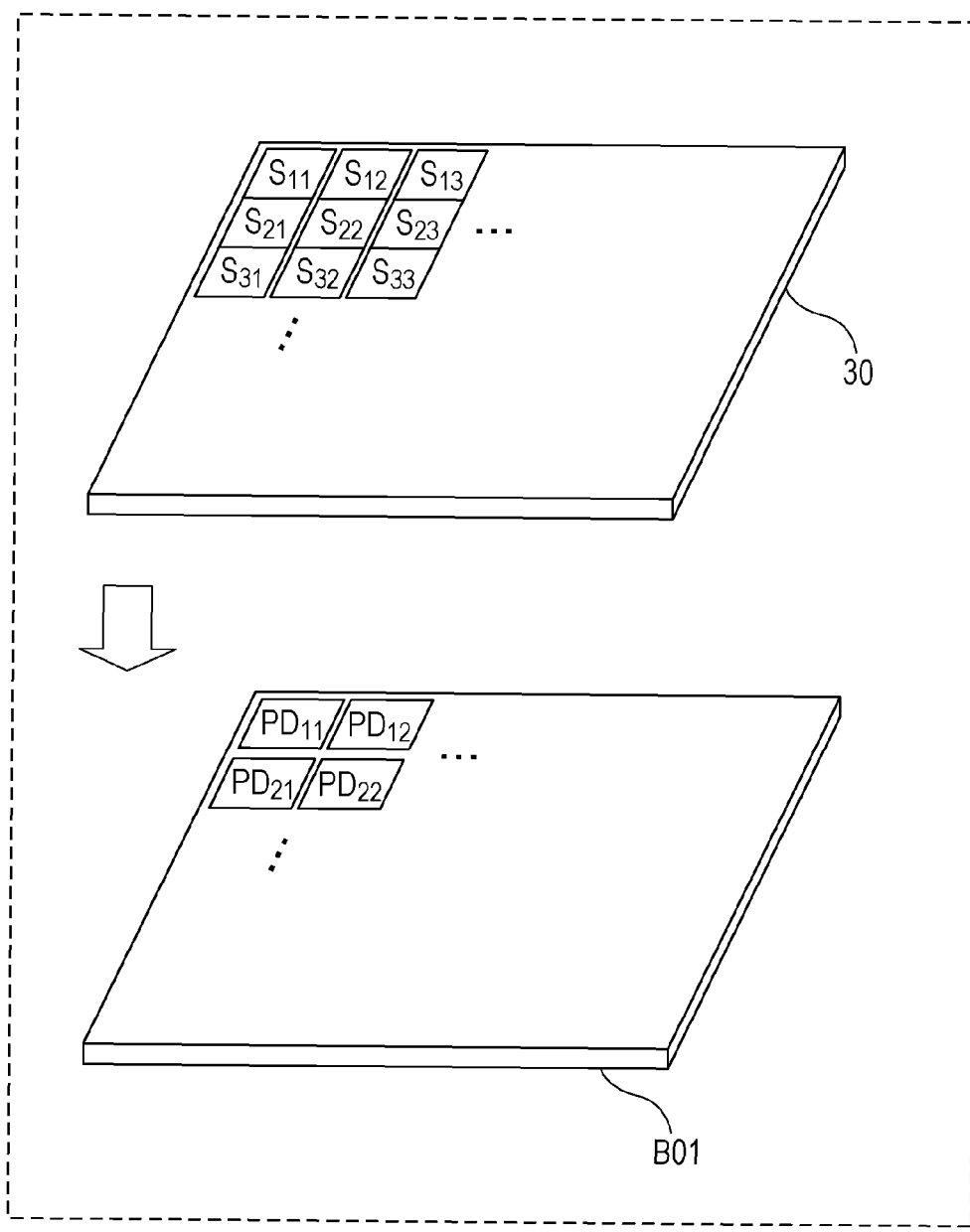
FIG. 33 is a perspective view schematically illustrating the positional relationship between a pathology specimen and an image sensor according to the seventh embodiment of the present disclosure.

In step S111 (FIG. 30), by using the illuminating device 210 (FIG. 29), parallel light is applied to a specimen to be imaged at the angle adjusted in step S110. Light emitted from the light source unit C09 is incident on the image sensor B01 via the transparent plate 31 of the preparation 11. An example of changing of the illuminating direction is shown in FIGS. 32A and 32B. The arrangement of the pathology specimen 30 and that of the pixels of the image sensor B01 are two-dimensionally related to each other, as shown in FIG. 33. In the configurations illustrated in FIGS. 32A and 32B, the image sensor B01 has an array of photoelectric converters (in this case, photodiodes PDs). For a simple representation, in FIGS. 32A and 32B, a cross section of only one pixel including one photodiode PD is schematically shown. Light incident on the photodiode PD is converted into an electric signal by means of photoelectric conversion. In FIGS. 32A and 32B, the thickness of the arrow schematically represents the amount of light incident on the photodiode PD. As the arrow is thicker, it means that a greater amount of light is incident on the photodiode PD.

In the example shown in FIG. 32A, parallel light is incident from a direction right above the pathology specimen 30. In this case, light passing through regions S2 and S3 of the pathology specimen 30 is incident on the photodiode PD. On the other hand, when parallel light is incident on the pathology specimen 30 at the angle shown in FIG. 32B, light passing through regions S2, S3, and S4 of the pathology specimen 30 is incident on the photodiode PD. For example, half of light passing through each of the regions S2 and S4 of the pathology specimen 30 is incident on the photodiode PD, while light passing through the region S3 is substantially entirely incident on the photodiode PD. In this case, the pixel value which is output from the photodiode PD under the condition of the illuminating direction shown in FIG. 32B is different from that under the condition of the illuminating direction shown in FIG. 32A.

As is seen from the examples shown in FIGS. 32A and 32B, from a single image acquired by applying light in only one illuminating direction, it is not possible to find the pixel value for each of the regions of one pixel, in this case, the pixel value indicating the amount of light passing through each of the regions S1, S2, S3, and S4. In the specimen image acquiring device 110 in the seventh embodiment, however, as shown in FIGS. 32A and 32B, the pixel value indicating the amount of light passing through each of the regions S1, S2, S3, and S4 can be found from multiple images acquired as a result of applying light by changing the illuminating direction. Each of the regions S1, S2, S3, and S4 is smaller than the size of one pixel, and this corresponds to a sub-pixel region. This will be described in a greater detail below.

An example in which light is applied to the pathology specimen 30 from four different directions (directions Drr1, Drr2, Drr3, and Drr4) will be considered. In this case, as a result of applying light from the different directions Drr1, Drr2, Drr3, and Drr4, four images are obtained. Among the pixels forming each of the four images, one pixel located at the same position (coordinates) of the four images will now be focused. Outputs from the photodiode PD of this pixel are set to be A1, A2, A3, and A4 in association with the directions Drr1, Drr2, Drr3, and Drr4, respectively. The light transmittance ratios of light passing through the regions S1, S2, S3, and S4 of the pathology specimen 30 are set to be S1, S2, S3, and S4, respectively. In this case, in the example (direction Drr1) shown in FIG. 32A, the equation expressed by $A1 = 0 \times S1 + 1 \times S2 + 1 \times S3 + 0 \times S4$ ($\times$ means multiplication) holds true. In the example (direction Drr2) shown in FIG. 32B, the equation expressed by $A2 = 0 \times S1 + (½) \times S2 + 1 \times S3 + (½) \times S4$ holds true. It is now assumed that concerning the direction Drr3, which is not shown, $A3 = 0 \times S1 + 0 \times S2 + (½) \times S3 + 1 \times S4$ holds true and that concerning the direction Drr4, which is not shown, $A4 = (½) \times S1 + 1 \times S2 + (½) \times S3 + 0 \times S4$ holds true.

In the above-described example, the light transmittance ratios S1, S2, S3, and S4 are unknown values that are dependent on the tissue structure of the pathology specimen 30. On the other hand, the outputs A1, A2, A3, and A4 from the photodiode PD can be determined by acquiring the four images. That is, simultaneous equations concerning the four unknown values S1, S2, S3, and S4 are determined, and it is possible to find the four unknown values S1, S2, S3, and S4 by calculation.

FIG. 34A shows a matrix of the coefficients of simultaneous equations in the above-described example. The inverse matrix of this matrix is applied to vectors having the outputs A1, A2, A3, and A4 as components, thereby making it possible to determine the light transmittance ratios S1, S2, S3, and S4 of smaller regions (sub-pixel regions) than one pixel. As a result, it is possible to acquire an image having a resolution level four times as high as that of each of the four images acquired as a result of applying light from the different directions Drr1, Drr2, Drr3, and Drr4. In other words, it is possible to acquire a high resolution image having a pixel density four times as high as that of the image sensor B01. The matrix shown in FIG. 34A is an example of the matrix used for making calculations for acquiring an image having a pixel density four times as high as that of the original image.

The numeric values (values of matrix elements) shown in FIG. 34A are not dependent on the tissue structure of the pathology specimen 30, but are dependent on the structure of the image sensor B01 and the illuminating direction. Even with the use of the same image sensor B01, if the illuminating direction is changed, the values of matrix elements are also changed. FIG. 34B shows an example of matrix elements when light is applied from different directions Drr1 through Drr8. The matrix shown in FIG. 34B is an example of the matrix used for making calculations for acquiring an image having a pixel density eight times as high as that of the original image. In this example, since the number of sub-pixel regions is eight, light is applied to the pathology specimen 30 at least from the eight different directions Drr1 through Drr8 so as to acquire eight outputs for each pixel. Then, the light transmittance ratios of the eight sub-pixel regions, which are unknown values, can be determined. As a result, it is possible to acquire an image having a resolution level eight times as high as that of the original image. In other words, it is possible to acquire a high resolution image having a pixel density eight times as high as that of the image sensor B01.

In the seventh embodiment, the resolution of an image can be increased in this manner. In other words, by performing imaging by changing the illuminating direction, an image of a different resolution level (magnification) can be acquired as a specimen image. In this manner, in the seventh embodiment, unlike imaging using an optical microscope, the focusing operation is not necessary, which is normally required every time the objective lens is changed.

Referring back to FIG. 30, in step S112, the pathology specimen 30 is imaged by using the image sensor B01. Processing operations in steps S110 through S112 may be executed under the control of the information processing device 230 for the individual components. That is, under the control of the information processing device 230, light is applied to an object multiple times at different angles so that imaging can be performed at each of the different angles. More specifically, the information processing device 230 controls the light source unit and the image sensor B01 of the preparation 11 mounted on the socket C03 so as to cause the image sensor B01 to image the object in the preparation 11. In a general image sensor, such as a scanner, a line sensor is usually used. If an area sensor, such as a CCD image sensor, is used as the image sensor B01, a wide range image required for identifying a specimen can be captured at a high speed. In the specimen image acquiring device 110 of the seventh embodiment, lenses for changing the magnifying power are not used. Instead, in the seventh embodiment, the specimen image acquiring device 110 generates an image of a desired magnification from multiple images acquired as a result of performing imaging by changing the illuminating direction.

In step S113, it is determined whether or not all images necessary to generate a specimen image of a specified magnification have been prepared. If all images have been prepared, the process proceeds to step S114. If not all images have been prepared, the process returns to step S110. Then, after changing the illuminating direction, imaging is performed in this illuminating direction.

In step S114, an image of a specified magnification is generated from multiple images acquired by the information processing device 230 in steps S110 through S113 in accordance with the different illuminating directions. In order to generate an image of a specified magnification, a matrix representing the relationship between the illuminating directions and the amounts of light to be incident on the photodiode PD is stored in the matrix storage unit 250 in advance. FIGS. 34A and 34B show examples of matrixes representing the relationship between the illuminating directions and the amounts of light to be incident on the image sensor. Such a matrix may be determined by calculation from the illumination angle, the size of the photodiode PD, and the size of a pixel to be determined. Alternatively, by using a test specimen for which pixel values are known, the values of the matrix elements may be determined by experiment. In this case, measurements may be made to determine which region of the pathology specimen 30 light passes and how much light is incident on the photodiode PD in accordance with the illumination angle.

It is assumed that a matrix representing the relationship between the illuminating directions and the amounts of light to be incident on an imaging element is represented by M, a vector having a pixel value obtained in accordance with each of the illuminating directions as a component is represented by A, and a vector S to be found is S. In this case, the relationship MS=A holds true for each pixel. In this relationship, since the matrix M and the value A are known, each component of S (the light transmittance ratio of each sub-pixel region) can be found by inverse matrix calculations. In step S114 of the example shown in FIG. 30, the matrix representing the relationship between the illuminating directions and the amounts of light to be incident on the photodiode PD is obtained from the matrix storage unit 250, and the pixel value of each sub-pixel region is calculated by the inverse matrix calculator 240. By using the specimen management apparatus configured as described above, a full image of the specimen at a desired magnification can be acquired. The above-described processing may be executed by the specimen image acquiring device 110.

In step S12 (FIG. 28), the image feature quantity for identifying the specimen is calculated by the image feature quantity calculator 120 from the specimen image obtained in step S11. As the image feature quantity, color information concerning, for example, the average brightness, configuration characteristics such as the degree of circularity, and features obtained by SIFT (Scale-Invariant Feature Transform), HOG (Histogram of Oriented Gradient), and HLAC (High-order Local Autocorrelation) may be used. As the feature quantity unique to pathology images, features, such as a cell-nucleus distance and the ratio between the color of a nucleus and the color of a cell, may be used.

Figure 35:
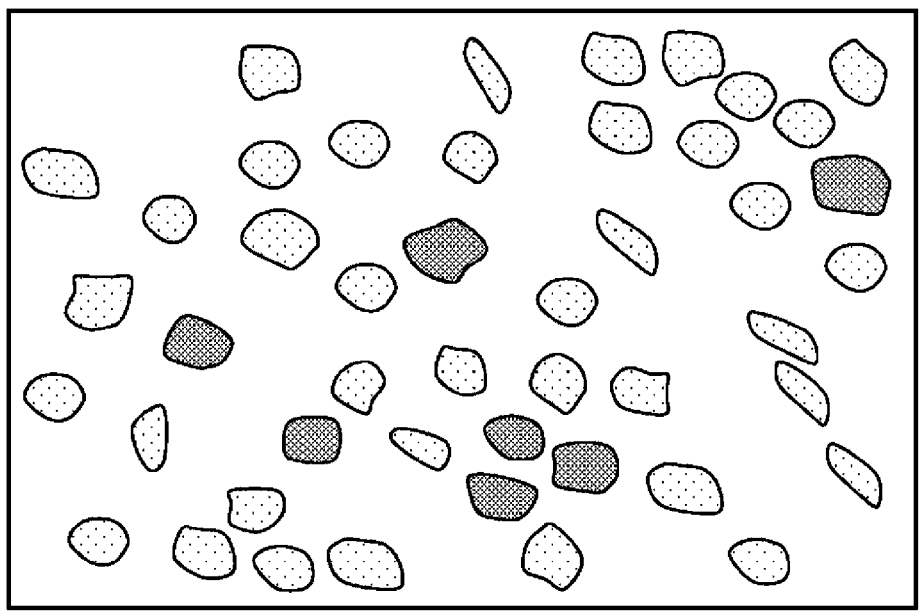
FIG. 35 is a view illustrating an example of an image obtained when a pathology specimen is examined at a high magnification (high resolution)
Figure 36:
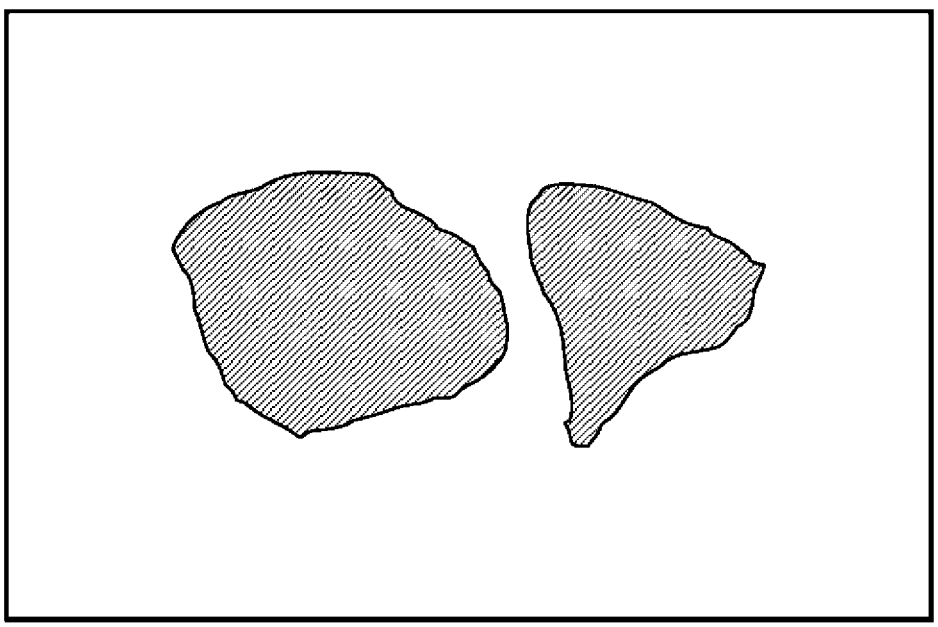
FIG. 36 is a view illustrating an example of an image obtained when a pathology specimen is examined at a low magnification (low resolution)

Examples of pathology images are shown in FIGS. 35 and 36. FIG. 35 shows an example of a pathology specimen examined at a high magnification (for example, ×200 or higher). FIG. 36 shows an example of a pathology specimen examined at a low magnification (for example, lower than ×10). If the magnification is N (N is an integer of 1 or greater), it means that the resolution (the number of pixels forming one image or the pixel density) of an image is increased to N×N. The magnification of a screen of a display included in the output device 170 is defined by the ratio of the pixel pitch of the display to the pixel pitch of the imaging elements.

If a pathology specimen is examined at a high magnification, cells and nucleuses can be identified, as shown in FIG. 35. Since the cell-nucleus arrangement and distance varies depending on the specimen, the average cell-nucleus distance may be used as a feature for identifying a specimen. Tissue to be examined in a pathology specimen is transparent, and thus, it is usually stained for easy examination. As the types of staining, hematoxylin-eosin (HE) staining, which is a basic staining protocol, and various types of immunostaining adapted to the specific purposes of examinations are available. The ratio concerning nucleuses and that concerning cells obtained by staining the tissue by using such a staining protocol may be used as a feature. For example, in Ki-67, which is one type of immunostaining, proliferative cells are stained in reddish brown, while the other cells are stained in blue. The ratio concerning the cells may be used as a reference for diagnosis and may be useful as identification information concerning a pathology specimen. In step S12, the image feature quantity to be mainly used may be changed according to the magnification of an image indicating a pathology specimen. In pathology specimens, the features of a specimen image are very different depending on the magnification at which the specimen is examined. If a specimen is examined at a high magnification, cells and nucleuses can be identified from the resulting image, as shown in FIG. 35. If a specimen is examined at a low magnification, the overall configuration of a pathology section can be identified from the resulting image, as shown in FIG. 36. By considering this point, concerning images with a low magnification, features suitable for typical configuration recognition, such as the degree of circularity, SIFT, HOG, and HLAC, may be mainly used. On the other hand, concerning images with a high magnification, features unique to pathology specimens, such as the cell-nucleus distance and the ratio of colors obtained by staining, may be mainly used. For example, if the resolution of an image is lower than a reference value, at least one of features such as the degree of circularity, SIFT, HOG, and HLAC may be calculated. If the resolution of an image is equal to or higher than the reference value, the average distance between cells or nucleuses and/or the ratio of colors obtained by staining may be calculated in addition to the above-described features.

Figure 39A:
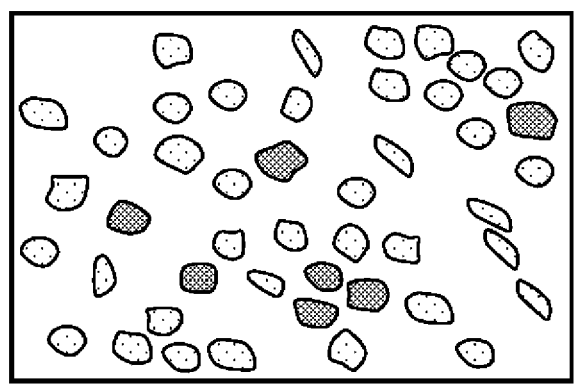
FIG. 39A is a schematic view illustrating an example of an image of a specimen stained with "stain A"
Figure 39B:
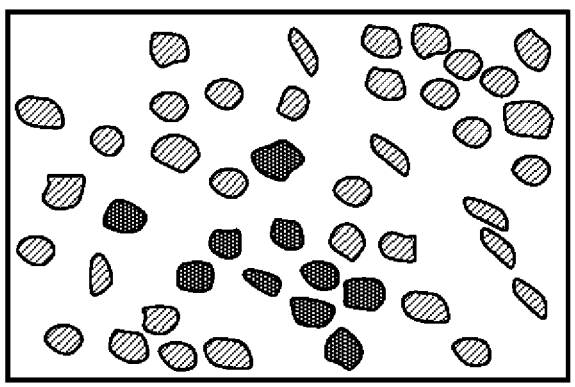
FIG. 39B is a schematic view illustrating an example of an image of a specimen stained with "stain B"

In step S13, the information search unit 130 searches the database 140 for patient data corresponding to an image having a feature quantity that matches the image feature quantity calculated in step S12. An example of the database 140 is shown in FIG. 37. The database 140 stores, as patient data, image feature quantities calculated from pathology specimen images, magnifications of the specimen images used for calculating the image feature quantities, and patient information in association with each other. By storing patient information in a format like this, patient data associated with an image feature quantity that matches the image feature quantity calculated in step S12 can be searched for from the database 140. In a search, exact matching between image feature quantities may be used as a condition for determining that there is patient information associated with the feature quantity calculated in step S12. Alternatively, image feature quantities may be expressed by, for example, vectors, and when the Euclidean distance between vectors is equal to or smaller than a predetermined threshold, it may be determined that two image feature quantities match each other. The database 140 may be in a format shown in FIG. 38. In the format illustrated in FIG. 38, by adding a patient ID, plural items of information concerning specimens of different stains of the same patient are associated with each other. In today's pathology examination (tissue diagnosis), in addition to HE staining, which is a basic staining protocol, immunostaining adapted to the specific purposes of examinations is frequently performed. FIGS. 39A and 39B show examples of an image of a specimen stained with a certain "stain A" and an image of a specimen stained with another "stain B" of the tissue removed from the same patient. Regarding specimens of different stains of the same patient, such as those shown in FIGS. 39A and 39B, although the colors are totally different, the configurations of the specimens are almost the same in many cases. This is because, when specimens of plural stains are prepared from the same patient, they are usually prepared by using continuous slices (thin sections). In the embodiments of the present disclosure, information concerning specimens is obtained in the form of images. Accordingly, if the above-described characteristics of pathology specimens are utilized, by comparing the feature quantities of the obtained images with each other in terms of the configuration, specimens of different stains of the same patient can be automatically associated with the same patient ID.

In step S14, it is determined whether or not, as a result of a search in step S13, patient data having the same image feature quantity as that calculated in step S12 has been found in the database 140. If patient data having the same image feature quantity has not been found in the database 140, the process proceeds to step S15. If patient data having the same image feature quantity has been found in the database 140, the process proceeds to step S17.

In step S15, an instruction to input patient information corresponding to the pathology specimen placed in step S10 is given by using the input device 160. In step S16, the patient information input in step S15 is stored in the database 140 in association with the magnification of the specimen image obtained in step S11 and the image feature quantity calculated in step S12.

In step S17, it is determined whether or not, as a result of a search in step S13, plural items of patient data associated with the same image feature quantity as that calculated in step S12 have been found in the database 140. If it is not possible to specify the single item of patient information since plural items of patient information associated with the same image feature quantity as that calculated in step S12 have been found in the database 140, the process proceeds to step S18. If there is only one item of patient information associated with the same image feature quantity as that calculated in step S12, the process proceeds to step S19.

In step S18, the magnification of an image to be obtained is changed, and the process returns to step S11. In pathology specimens, even in a case in which the configurations of specimens are similar in low magnification images, the specimens can be distinguished from each other if cells or nucleuses are examined in high magnification images. On the other hand, however, there is a tradeoff relationship between the magnification and the time taken to capture a specimen image in step S11. Accordingly, it is efficient if the operator first makes an effort to identify a specimen by using a low magnification image, and if the operator is unable to identify the specimen, the magnification is increased. For example, in steps S11 through S17, the magnification is repeatedly increased until only the single item of patient information is specified. When adding patient information associated with a new specimen to the database 140, among the image features, a configuration feature, which is not dependent on the colors, is first utilized to search the database 140 for a case having the same configuration feature, and if there is such a case, this new specimen may be associated with this case as a specimen of a different stain of the same patient.

In step S19, the patient information obtained in step S13 is output by using the output device 170. It is not always necessary that the output device 170 by itself have a display or a printer. The output device 170 may be a device which is connected to an external display or printer and outputs a signal to such a display or printer.

With the configuration of the seventh embodiment, precise pathology specimen management with a less burden on operators is implemented. Additionally, in the specimen management of the seventh embodiment, it is not necessary to provide barcodes or IC tags to pathology slides.

Eighth Embodiment

A specimen management apparatus 300A according to an eighth embodiment will be described below with reference to FIGS. 40A, 40B, and 41.

Figure 40A:
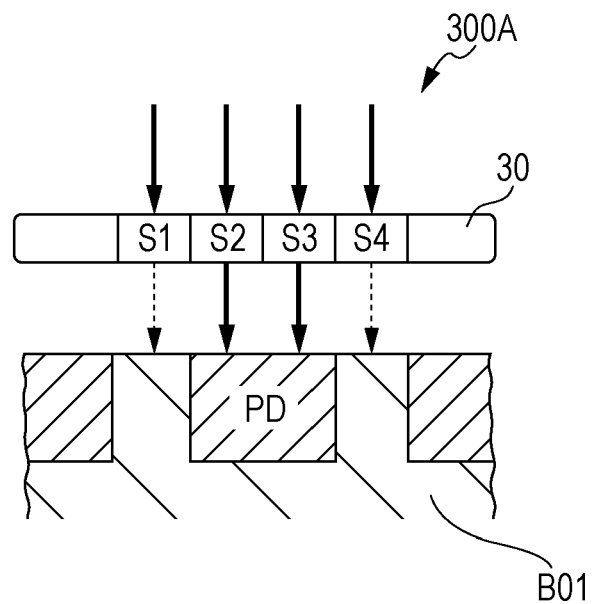
FIG. 40A is a schematic view illustrating an example of the operation of a specimen image acquiring device according to an eighth embodiment of the present disclosure.
Figure 40B:
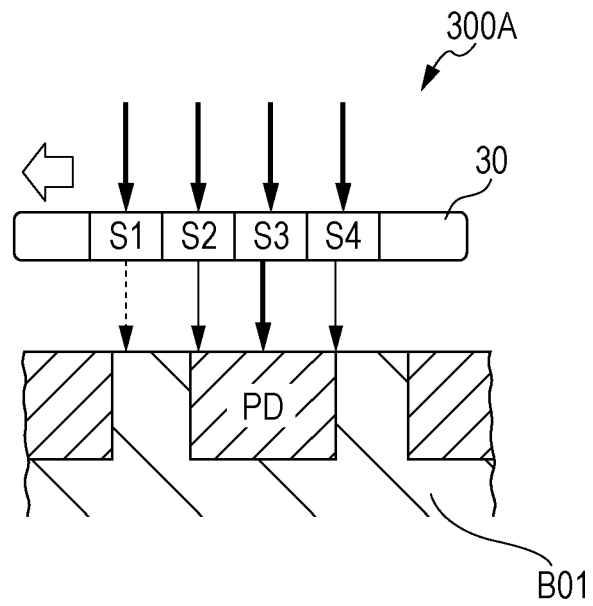
FIG. 40B is a schematic view illustrating an example of the operation (shifting of a specimen) of the specimen image acquiring device according to the eighth embodiment of the present disclosure.

The specimen management apparatus 300A of the eighth embodiment images the pathology specimen 30 placed on the socket C03 while shifting the pathology specimen 30, as shown in FIGS. 40A and 40B, thereby obtaining multiple images used for generating a high magnification specimen image. The configuration of the specimen management apparatus 300A is similar to the specimen management apparatus 300 of the seventh embodiment, except for the configuration of a specimen image acquiring device 110A.

Figure 41:
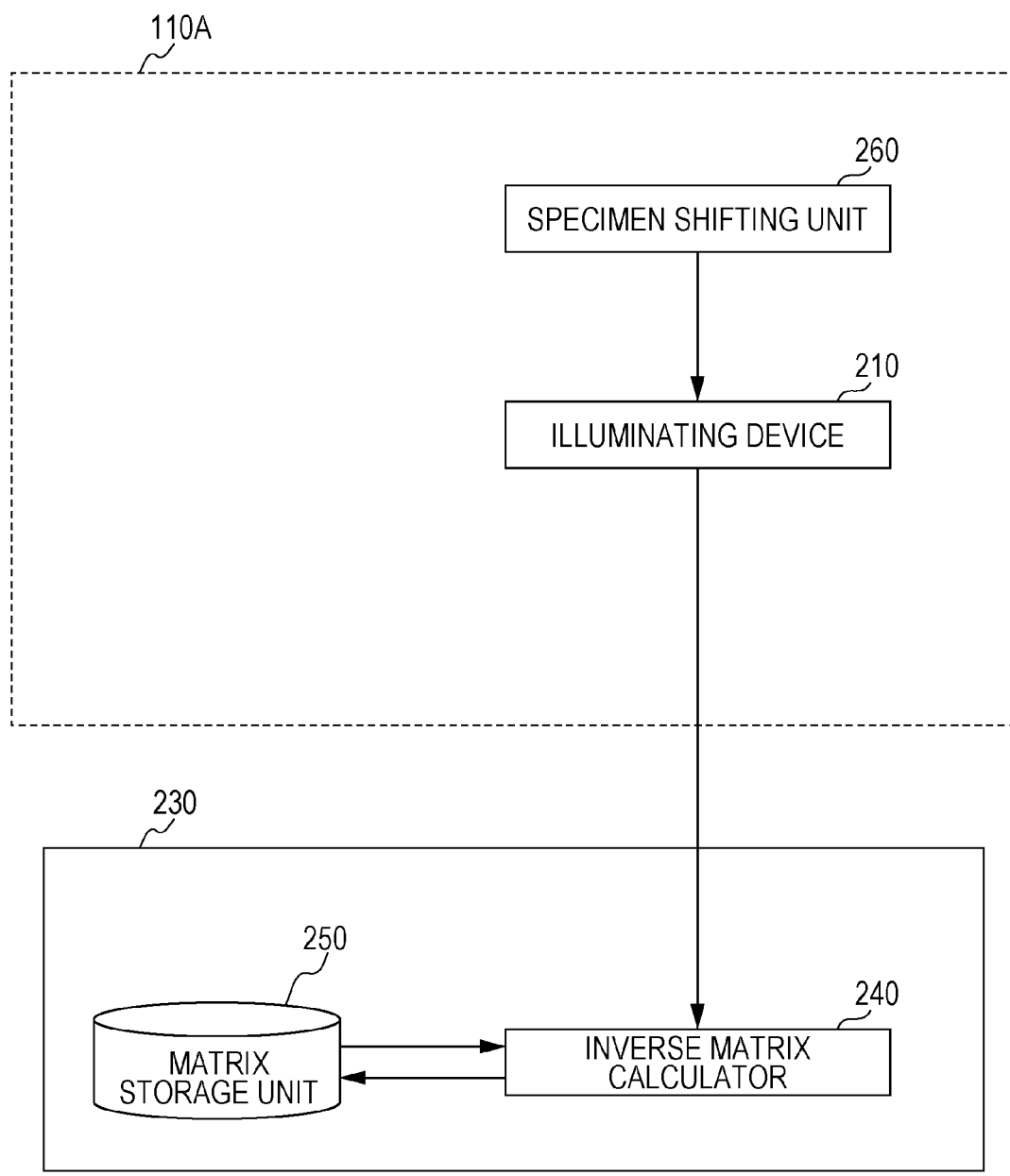
FIG. 41 is a block diagram illustrating an example of the configuration of the specimen image acquiring device according to the eighth embodiment of the present disclosure.

FIG. 41 is a block diagram illustrating an example of the configuration of the specimen image acquiring device 110A of the eighth embodiment. As illustrated in FIG. 41, the specimen image acquiring device 110A is different from the specimen image acquiring device 110 shown in FIG. 29 in that the specimen image acquiring device 110A includes a specimen shifting unit 260 instead of the illuminating direction adjuster 200. In the eighth embodiment, instead of acquiring multiple images by changing the position of a light source to be turned ON, by imaging a specimen while shifting the specimen itself, multiple images are acquired for generating a high magnification image. With this configuration, too, the illuminating direction of parallel light can be changed. Instead of storing a matrix representing the relationship between the positions of light sources and the amounts of light to be incident on imaging elements, a matrix representing the relationship between the shifting directions and distances of a specimen and the amounts of light to be incident on imaging elements is stored in the matrix storage unit 250. The specimen image acquiring device 110A configured as described above realizes the function of acquiring an image of a desired magnification by performing processing similar to steps S110 through S114 discussed with reference to FIG. 30. However, in step S110, instead of adjusting the positions of light sources, the specimen placed on the socket C03 is shifted. In the configuration of the eighth embodiment, the direction of parallel light to be emitted from the light sources may be uniform. By applying processing similar to that of the seventh embodiment to steps S111 through S114, a high magnification image can be generated from multiple low magnification images.

Ninth Embodiment

Figure 42:
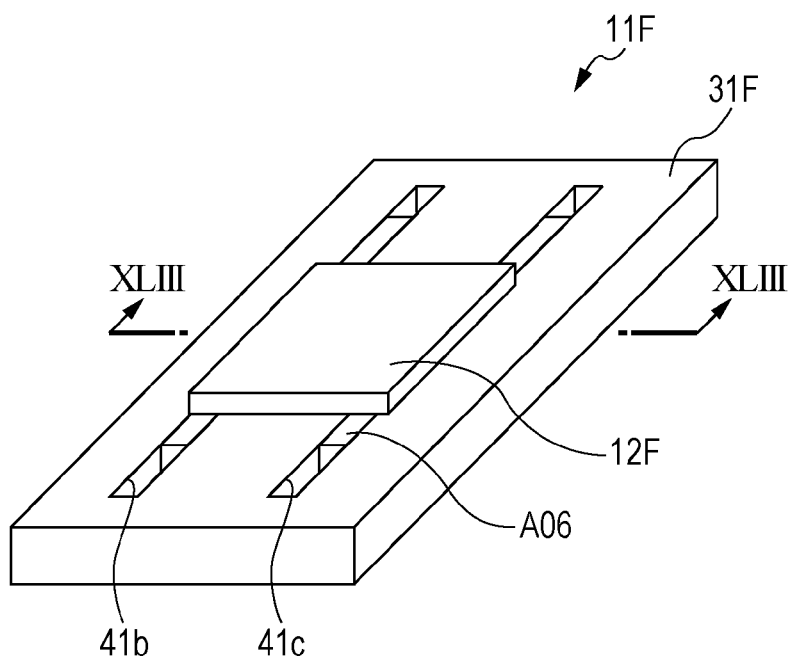
FIG. 42 is a perspective view illustrating an example of the configuration of a preparation according to a ninth embodiment of the present disclosure.
Figure 43:
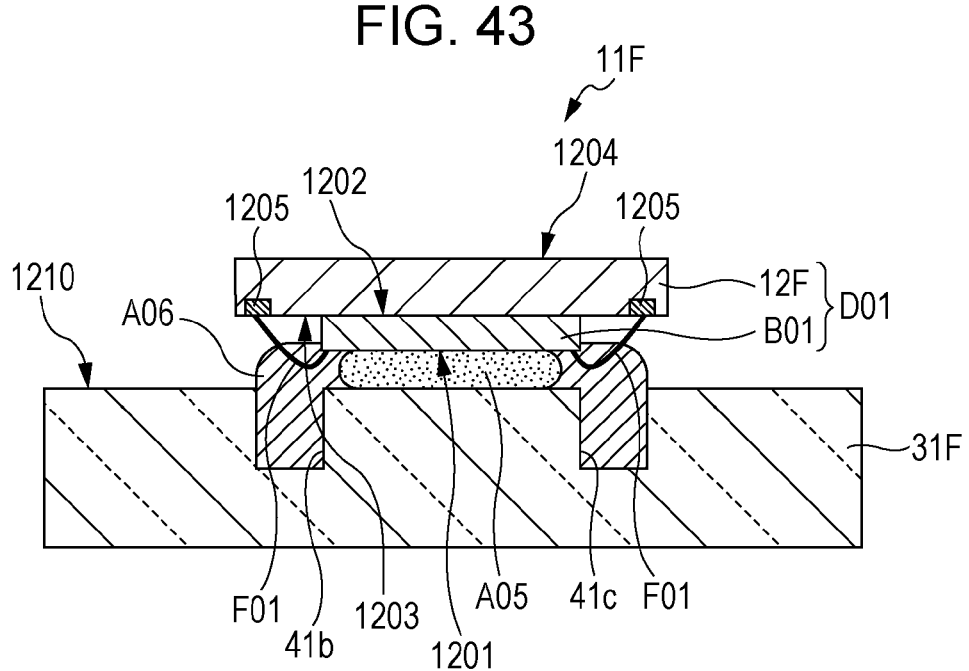
FIG. 43 is a schematic sectional view illustrating the preparation taken along line XLIII-XLIII of FIG. 42.

FIG. 42 illustrates an example of the configuration of a preparation 11F according to a ninth embodiment of the present disclosure. FIG. 43 schematically illustrates a cross section of the preparation 11F taken along line XLIII-XLIII of FIG. 42. The preparation 11F shown in FIG. 42 includes a transparent plate 31F having grooves on the surface. In the example shown in FIGS. 42 and 43, the transparent plate 31F has first and second grooves 41b and 41c on the surface. In this manner, the transparent plate 31F of the ninth embodiment has two or more grooves on the surface. However, the shape of the transparent plate 31F is rectangular and the first and second grooves 41b and 41c are formed in substantially parallel with the longitudinally direction of the transparent plate 31F. The shape of the transparent plate 31F is not restricted to a rectangle. The first and second grooves 41b and 41c may be separate, different grooves, or may be interconnected to each other by another groove. As the number of grooves, the number of linearly extending portions is counted. The transparent plate 31F may be slide glass having two or more grooves formed on the surface.

As shown in FIG. 43, the preparation 11F includes the transparent plate 31F and an image sensor unit D01. The image sensor unit D01 includes an image sensor B01 and a package 12F. The image sensor B01 is electrically connected to the package 12F via plural electrodes F01 in the state in which the back surface 1202 of the image sensor B01 is supported by the front surface 1203 of the package 12F. In this example, the package 12F does not have side walls protruding from the front surface 1203 (for example, see FIG. 10) and is substantially flat.

As shown in FIG. 43, the transparent plate 31F is disposed so that it may oppose the front surface 1201 of the image sensor B01. In this case, a front surface 1210 of the transparent plate 31F on which the first and second grooves 41b and 41c are formed opposes the front surface 1201 of the image sensor B01. A stained section A05, at least part of which is covered with a mounting medium A06, is disposed between the image sensor B01 and the transparent plate 31F.

In the configuration illustrated in FIGS. 42 and 43, the image sensor unit D01 and the transparent plate 31F are integrated with each other as a result of being fixed by the mounting medium A06. As shown in FIG. 43, part of the mounting medium A06 is positioned within the first and second grooves 41b and 41c. The mounting medium A06 is a liquid before drying, and serves to prevent an object (for example, the stained section A05) from drying. As described above, in the ninth embodiment, the transparent plate 31F has the first and second grooves 41b and 41c on the front surface 1210 which opposes the front surface 1201 of the image sensor B01. With this configuration, when producing the preparation 11F, even if the mounting medium A06 is applied to the object more than necessary, a surplus of the mounting medium A06 may flow into the first and second grooves 41b and 41c in the process of integrating the transparent plate 31F and the image sensor unit D01 with each other. Accordingly, it is possible to make the front surface 1201 of the image sensor B01 and the front surface 1210 of the transparent plate 31F oppose in substantially parallel with each other. As a result, the distance between the imaging area of the image sensor B01 and the front surface 1210 of the transparent plate 31F can be made uniform, thereby making it possible to obtain even sharper images.

In the configuration illustrated in FIG. 43, the apexes of the plural electrodes F01 (portions closest to the front surface 1210 of the transparent plate 31F) and the vicinities thereof are positioned within the mounting medium A06. As described above, since the mounting medium A06 is a liquid before drying, there is no problem even if the plural electrodes F01 contact the mounting medium A06 while producing the preparation 11F. Before the assembling of the preparation 11F, the plural electrodes F01 connected to the image sensor unit D01 may have been sealed with a resin.

As the mounting medium A06, a mounting medium containing xylene, for example, is used. The refractive index of such a mounting medium is substantially the same as that of glass. Accordingly, by filling the first and second grooves 41b and 41c with the mounting medium A06, it is possible to suppress the refraction of light through the first and second grooves 41b and 41c. In this manner, since the first and second grooves 41b and 41c serve to store the mounting medium A06 therein, the refraction of light through the first and second grooves 41b and 41c can be suppressed, thereby suppressing the deterioration of images caused by the refraction of light. Additionally, since the refraction of light through the first and second grooves 41b and 41c can be suppressed, it is relatively easy to increase the resolution by utilizing multiple images obtained by changing the illuminating direction discussed in the seventh and eighth embodiments. However, regarding the setting of the illuminating direction for obtaining multiple images, the illuminating direction in which the first and second grooves 41b and 41c are not interposed between the light sources and the photoelectric converters of the image sensor B01 is preferentially set. The setting of the illuminating direction in this manner is more effective for suppressing the deterioration of the image quality.

Figure 44A:
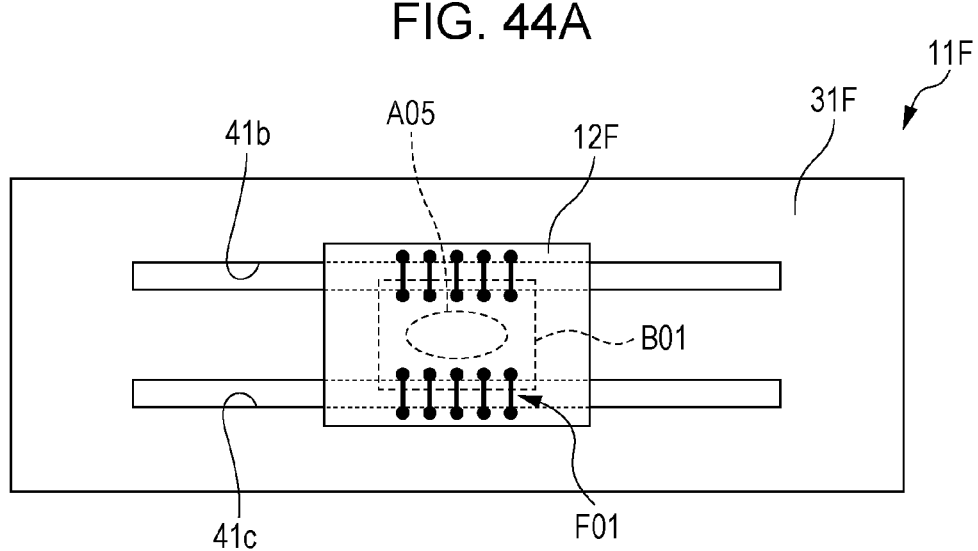
FIG. 44A is a top view illustrating an example of the relationship between the direction in which grooves are formed in the transparent plate and the direction in which the plural electrodes connected to the image sensor are arranged.

FIG. 44A illustrates an example of the relationship between the direction in which grooves are formed in the transparent plate 31F and the direction in which the plural electrodes F01 connected to the image sensor B01 are arranged. In this example, the shape of the image sensor B01 and the package 12F as viewed from a direction normal to the surface of the transparent plate 31F is a rectangle. However, the shape of the image sensor B01 and the package 12F is not restricted to a rectangle.

As shown in FIG. 44A, the image sensor B01 is disposed between the first and second grooves 41b and 41c. In the example shown in FIG. 44A, part of the image sensor B01 overlaps the first and second grooves 41b and 41c. In this manner, it is not necessary that the entirety of the image sensor B01 be disposed in a region between the first and second grooves 41b and 41c. In an embodiment of the present disclosure, overlapping of the image sensor B01 with the first groove 41b or the second groove 41c is allowed. The state in which part of the image sensor B01 overlaps the first groove 41b or the second groove 41c is included in the state in which the image sensor B01 is disposed between the first and second grooves 41b and 41c. Part of an object may overlap the first groove 41b or the second groove 41c as long as it does not contact any of the plural electrodes F01.

In the configuration illustrated in FIG. 44A, the plural electrodes F01 are arranged along the longitudinal direction of the image sensor B01. In this example, in the state in which the front surface 1210 of the transparent plate 31F on which the first and second grooves 41b and 41c are formed and the front surface 1201 of the image sensor B01 oppose each other, the extending direction of the first and second grooves 41b and 41c and the arranging direction of the plural electrodes F01 are parallel with each other.

The stained section A05 is as about a few or several micrometers (μm). Accordingly, the apexes of the plural electrodes F01 generally protrude toward the transparent plate 31F rather than toward the front surface 1201 of the image sensor B01. In the configuration illustrated in FIG. 44A, since the extending direction of the first and second grooves 41b and 41c and the arranging direction of the plural electrodes F01 are parallel with each other, the apexes of the plural electrodes F01 are generally positioned within the first groove 41b or the second groove 41c. That is, the first and second grooves 41b and 41c may also serve to prevent the plural electrodes F01 from contacting or interfering with the front surface 1210 of the transparent plate 31F. In this manner, by providing the first and second grooves 41b and 41c on the front surface 1210 of the transparent plate 31F which opposes the front surface 1201 of the image sensor B01, it is possible to prevent the plural electrodes F01 from contacting or interfering with the front surface 1210 of the transparent plate 31F.

Figure 44B:
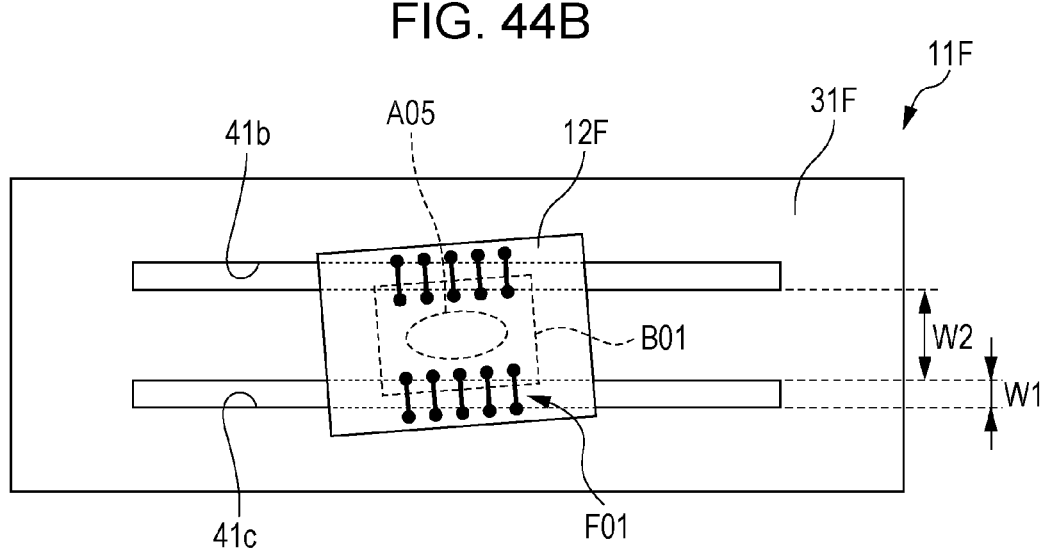
FIG. 44B is a top view illustrating another example of the relationship between the direction in which grooves are formed in the transparent plate and the direction in which the plural electrodes connected to the image sensor are arranged.

FIG. 44B illustrates another example of the relationship between the direction in which grooves are formed in the transparent plate 31F and the direction in which the plural electrodes F01 connected to the image sensor B01 are arranged. In the configuration illustrated in FIG. 44B, the extending direction of the first and second grooves 41b and 41c and the arranging direction of the plural electrodes F01 are not parallel with each other. However, the arrangement shown in FIG. 44B is also allowed as long as the plural electrodes F01 do not contact or interfere with the front surface 1210 of the transparent plate 31F. A width W1 of the first and second grooves 41b and 41c and a distance W2 between the first and second grooves 41b and 41c may be set by considering the production margin of the preparation 11F so that the apexes of the plural electrodes F01 can be stored in the first and second grooves 41b and 41c. In this manner, it is not necessary that the extending direction of the first and second grooves 41b and 41c and the arranging direction of the plural electrodes F01 be exactly parallel with each other.

Figure 45:
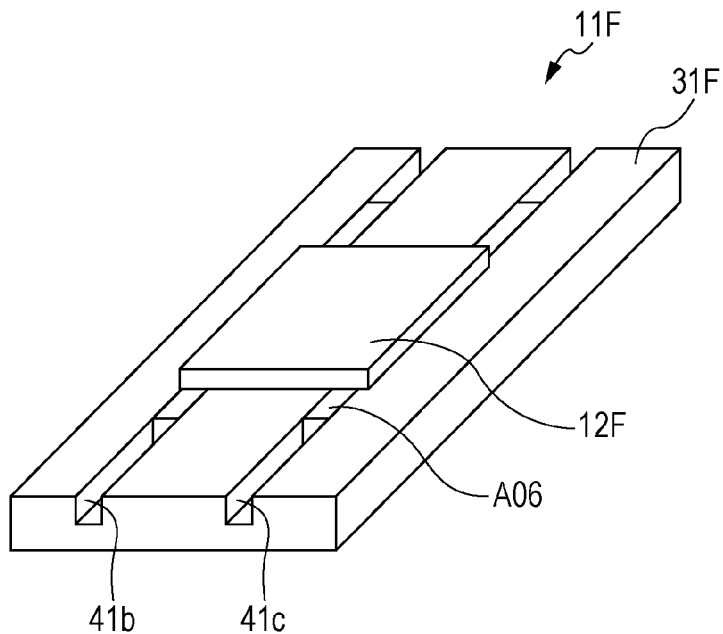
FIG. 45 is a perspective view illustrating a modified example of a transparent plate which may be used in the preparation according to the ninth embodiment of the present disclosure.

In the configuration illustrated in FIGS. 44A and 44B, the image sensor B01 is fixed to the transparent plate 31F so that the long sides of the image sensor B01 may be parallel or substantially parallel with the extending direction of the first and second grooves 41b and 41c. In this arrangement, it is more useful if the lengths of the first and second grooves 41b and 41c are longer than the length of the image sensor B01 because a larger space can be secured in which a surplus of the mounting medium A06 is allowed to flow when producing the preparation 11F. FIG. 45 shows a modified example of the transparent plate 31F. As illustrated in FIG. 45, the first and second grooves 41b and 41c may extend from one end to the other end of the transparent plate 31F. Depending on the arrangement of the plural electrodes F01, the image sensor B01 may be fixed to the transparent plate 31F so that the short sides of the image sensor B01 may be parallel or substantially parallel with the extending direction of the first and second grooves 41b and 41c. The depth of the first and second grooves 41b and 41c is not restricted to a specific size. However, it may be useful if the depth of the first and second grooves 41b and 41c is half the thickness of the transparent plate 31F or smaller in terms of securing of the required strength.

Figure 46:
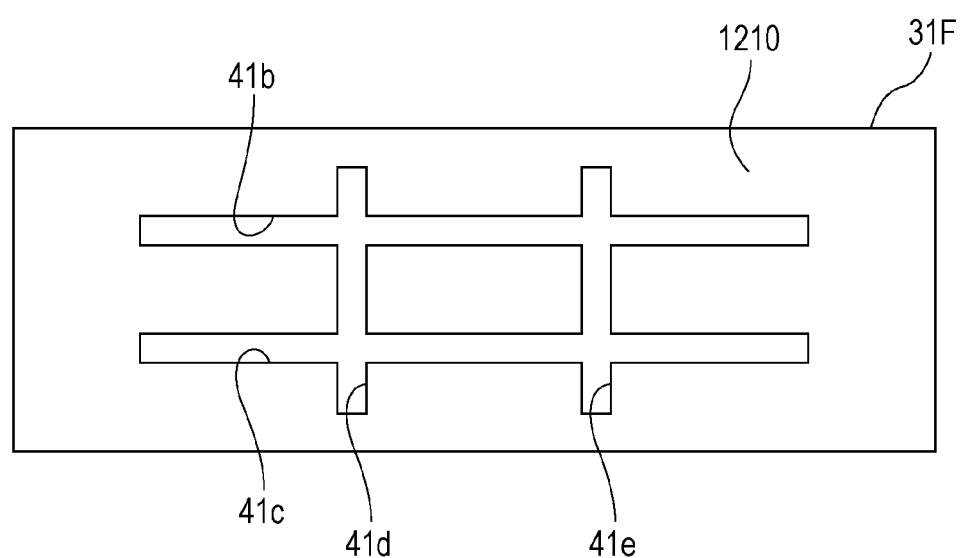
FIG. 46 is a top view illustrating another modified example of a transparent plate which may be used in the preparation according to the ninth embodiment of the present disclosure.

FIG. 46 shows another modified example of the transparent plate 31F. As shown in FIG. 46, the transparent plate 31F may also have third and fourth grooves 41d and 41e on the front surface 1210. In the example shown in FIG. 46, the third and fourth grooves 41d and 41e are formed in parallel with each other, and are provided perpendicularly to the first and second grooves 41b and 41c. The transparent plate 31F having four grooves may be useful in the case of the use of an image sensor unit having the plural electrodes F01 along the four sides of the image sensor B01. At least one of the first through fourth grooves 41b through 41e may extend toward an end of the transparent plate 31F.

When the transparent plate 31F having four grooves, such as that illustrated in FIG. 46, is used, the stained section A05 may be placed in a substantially rectangular region surrounded by the four grooves (first through fourth grooves 41b through 41e), and the image sensor B01 and the package 12F may be placed on the stained section A05 in this order. In this case, the grooves extending along the sides of the rectangular region may be used as alignment marks. When placing the image sensor B01 on the front surface 1210 of the transparent plate 31F, the image sensor B01 is fixed to the transparent plate 31F so that the sides of the image sensor B01 will be parallel with the grooves. In this manner, the image sensor B01 can be placed at a suitable position.

The package 12F in the ninth embodiment does not have side walls protruding from the front surface 1203. Accordingly, it is not necessary to form a structure in the transparent plate 31F for receiving the forward ends of side walls of the package 12F. In this manner, in the ninth embodiment, it is not necessary to provide a special structure in the transparent plate 31F which matches the configuration of the package 12F. Accordingly, the preparation 11F can be produced more easily while reducing the processing cost of the transparent plate 31F. For example, slide glass having grooves on the surface may be used as the transparent plate 31F of the preparation 11F, and slide glass having a length of 76 mm and a width of 26 mm may be used as the transparent plate 31F as long as the distance between grooves is a size of which the image sensor B01 can be placed in the region between the grooves.

Figure 47:
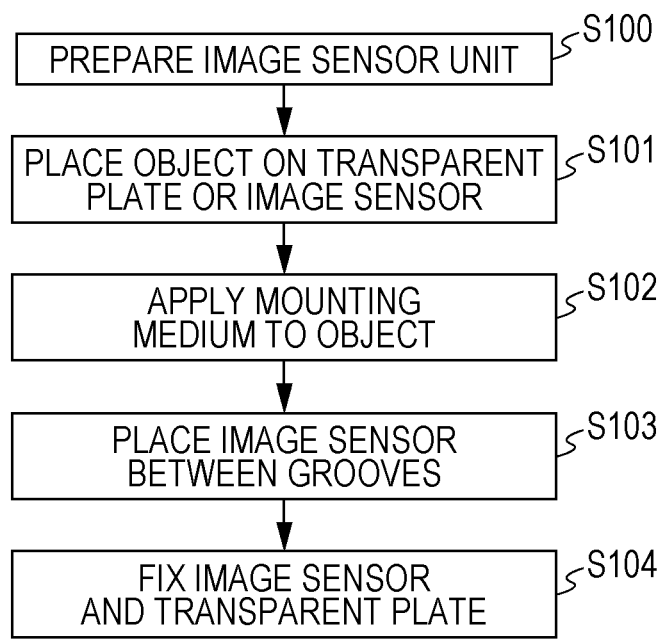
FIG. 47 is a flowchart illustrating an example of a producing method for the preparation according to the ninth embodiment of the present disclosure.

FIG. 47 is a flowchart illustrating an example of a producing method for the preparation 11F. First, in step S100, the image sensor unit D01 including the image sensor B01 and the package 12F is prepared. The front surface 1203 of the package 12F is placed so as to contact or oppose the back surface 1202 of the image sensor B01, and the package 12F and the image sensor B01 are electrically connected to each other via the plural electrodes F01. In this manner, the image sensor unit D01 can be formed.

Figure 48:
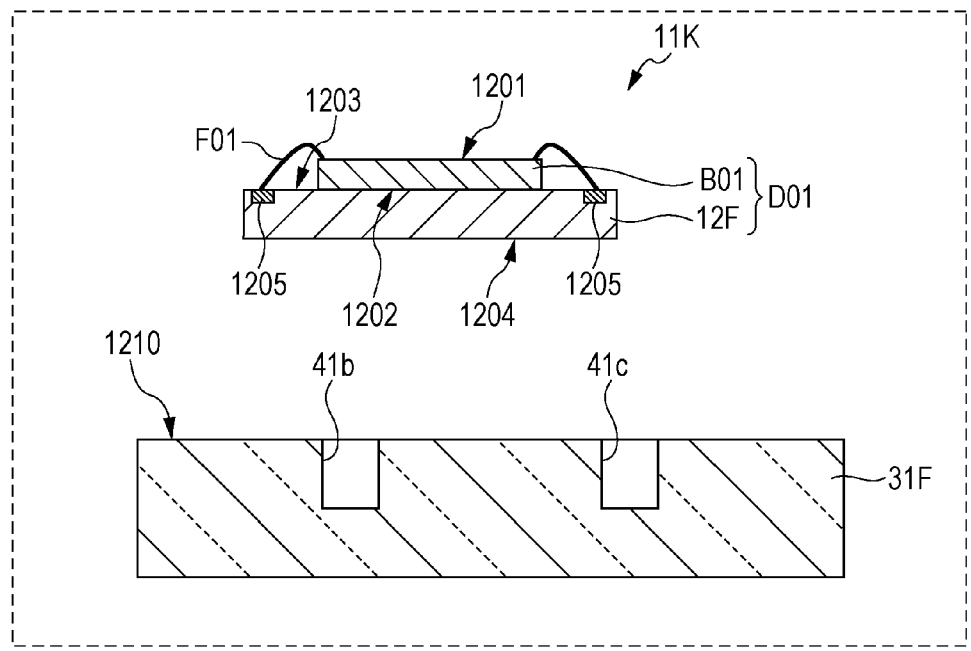
FIG. 48 is a view illustrating an example of a preparation component set.

The transparent plate 31F is prepared. The transparent plate 31F and the image sensor unit D01 may be provided as separate components which are not yet integrated, as illustrated in FIG. 48. In this specification, a set of a transparent plate and an image sensor unit which are not yet integrated with each other may be referred to as a "preparation component set". A preparation component set 11K shown in FIG. 48 is an example of the preparation component set. The preparations discussed in the other embodiments of the present disclosure may also be provided in the state of a preparation component set.

Then, in step S101, an object is placed on the front surface 1210 of the transparent plate 31F or on the front surface 1201 of the image sensor B01. After the object is set, it may be stained. After the object is stained, it is generally dried. Then, in step S102, the mounting medium A06 is applied to the object (for example, the stained section A05). If the object is placed on the front surface 1210 of the transparent plate 31F, the mounting medium A06 enters a portion between the object and the transparent plate 31F so as to cover the object. In this manner, the mounting medium A06 covers at least part of the object. Then, in step S103, before the mounting medium A06 dries, the image sensor B01 is placed between the first and second grooves 41b and 41c formed on the front surface 1210 of the transparent plate 31F. In a step of placing the image sensor B01 (and the package 12F) on the transparent plate 31F, the image sensor B01 is placed on the transparent plate 31F in the state in which the front surface 1210 of the transparent plate 31F and the imaging area of the image sensor B01 oppose each other with the mounting medium A06 (in this case, with the object) interposed therebetween. In this case, since the front surface 1210 of the transparent plate 31F opposes the imaging area of the image sensor B01, a surplus of the mounting medium A06 is allowed to flow into the first and second grooves 41b and 41c. With this configuration, it is possible to suppress the adhesion of the mounting medium A06 to the back surface (the surface opposite the front surface 1210) of the transparent plate 31F, thereby improving the work efficiency. Then, in step S104, by drying the mounting medium A06, the image sensor B01 and the transparent plate 31F are fixed. That is, by drying the mounting medium A06, the image sensor unit D01 and the transparent plate 31F can be integrated with each other. As a result, the preparation 11F shown in FIG. 42 is obtained. The drying of the mounting medium A06 is typically performed by means of air drying if the object is the stained section A05.

Tenth Embodiment

Figure 49:
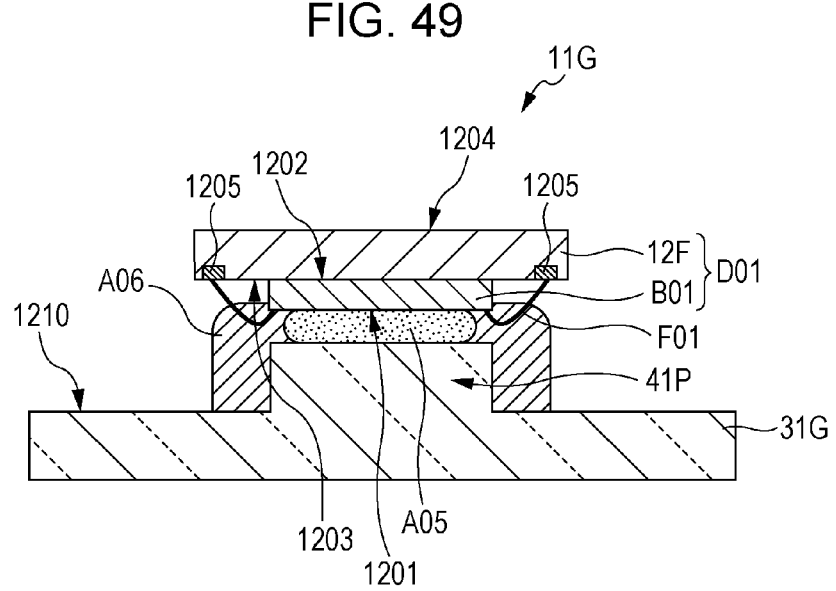
FIG. 49 is a schematic sectional view illustrating an example of a preparation according to a tenth embodiment of the present disclosure.

FIG. 49 illustrates an example of a preparation 11G according to a tenth embodiment of the present disclosure. Instead of using the transparent plate 31F having grooves on the surface, the preparation 11G shown in FIG. 49 includes a transparent plate 31G having a flat portion 41P on the front surface 1210 which opposes the front surface 1201 of the image sensor B01. The flat portion 41P protrudes from the front surface 1210. As shown in FIG. 49, in the preparation 11G, the front surface 1210 on which the flat portion 41P is formed opposes the front surface 1201 of the image sensor B01 with the mounting medium A06, which covers at least part of the object (in this case, the stained section A05), interposed therebetween. In the configuration illustrated in FIG. 49, the object is placed on the flat portion 41P, and the image sensor B01 is positioned on the flat portion 41P.

In this configuration, although the advantage of suppressing the influence of the refraction of light caused by the provision of grooves by storing a surplus of the mounting medium A06 in the grooves is not obtained, it is still possible to prevent the plural electrodes F01 from contacting or interfering with the front surface 1210 of the transparent plate 31G. It is easier to form plural grooves on the front surface 1210 of the transparent plate 31F than to form a step portion like the flat portion 41P on the front surface 1210. Accordingly, the transparent plate 31F is more advantageous than the transparent plate 31G in terms of the production cost.

As a transparent plate of a preparation according to an embodiment of the present disclosure, general flat slide glass may be used. As described above, however, if slide glass having recessed portions, grooves, or a protruding flat portion on the surface is used and combined with an image sensor unit, it is possible to reduce the influence of the refraction of light by storing a mounting medium within grooves (if grooves are formed in the slide glass) and to prevent the contact of electrodes with the transparent plate.

The above-described embodiments may be combined with each other unless there are inconsistencies between the combined embodiments.

An embodiment of the present disclosure may be applicable to, for example, a specimen management apparatus for conducting specimen management.

What is claimed is:

1. A preparation comprising:
   an image sensor having a front surface and a back surface opposite the front surface, the front surface including an imaging area;
   a package having a front surface and a rear surface and including a plurality of terminals which are electrically connected to the image sensor via a plurality of electrodes, the front surface of the package contacting or opposing the back surface of the image sensor; and
   a transparent plate disposed so as to oppose the front surface of the image sensor with a mounting medium interposed therebetween, the mounting medium being used for covering at least part of an object, the transparent plate having first and second grooves on a surface which opposes the front surface of the image sensor, wherein
   at least part of the image sensor is disposed between the first and second grooves, and
   at least part of each of the plurality of electrodes is positioned within the first groove or the second groove.

2. The preparation according to claim 1, wherein:
   the first and second grooves are parallel with each other; and
   in a state in which the surface of the transparent plate on which the first and second grooves are formed opposes the front surface of the image sensor, a direction in which the first and second grooves extend and a direction in which the plurality of electrodes are arranged are parallel with each other.

3. The preparation according to claim 1, wherein the first and second grooves extend from one end to the other end of the transparent plate.

4. The preparation according to claim 1, wherein:
   the transparent plate also has third and fourth grooves on the surface on which the first and second grooves are formed; and
   the third and fourth grooves are provided in parallel with each other while being perpendicular to the first and second grooves.

5. A transparent plate on which an image sensor and a package are mountable in order of the image sensor and the package,
   the image sensor having a front surface and a back surface opposite the front surface, the front surface including an imaging area,
   the package having a front surface and a rear surface and including a plurality of terminals which are electrically connected to the image sensor via a plurality of electrodes, the front surface of the package contacting or opposing the back surface of the image sensor, wherein:
   the transparent plate has first and second grooves on a surface of the transparent plate; and
   in a state in which the front surface of the image sensor opposes the surface of the transparent plate on which the first and second grooves are formed, at least part of the image sensor is disposed between the first and second grooves with a mounting medium interposed therebetween, the mounting medium being used for covering at least part of an object, and at least part of each of the plurality of electrodes is positioned within the first groove or the second groove.

6. The transparent plate according to claim 5, wherein the first and second grooves are parallel with each other, and in a state in which the image sensor is disposed between the first and second grooves, the first and second grooves extend in parallel with a direction in which the plurality of electrodes are arranged.

7. The transparent plate according to claim 5, wherein the first and second grooves extend from one end to the other end of the transparent plate.

8. The transparent plate according to claim 5, wherein:
the transparent plate also has third and fourth grooves on the surface on which the first and second grooves are formed; and
the third and fourth grooves are provided in parallel with each other while being perpendicular to the first and second grooves.

9. A method for producing a preparation, comprising:
preparing an image sensor unit including an image sensor and a package, the package including a plurality of terminals which are electrically connected to the image sensor via a plurality of electrodes;
disposing an object on a surface of a transparent plate on which first and second grooves are formed or on an imaging area of the image sensor;
applying a mounting medium to the object;
disposing, before the mounting medium dries, at least part of the image sensor unit between the first and second grooves in a state in which the surface of the transparent plate opposes the imaging area of the image sensor with the mounting medium interposed therebetween, so as to position at least part of each of the plurality of electrodes within the first groove or the second groove; and
fixing the image sensor unit and the transparent plate by drying the mounting medium.

10. An imaging apparatus comprising:
a socket on which the preparation according to claim 1 is mountable, the socket being electrically connected to the image sensor via the plurality of terminals of the package of the preparation;
a light source unit that emits light to be incident on the image sensor via the transparent plate of the preparation mounted on the socket; and
a control device that controls the light source unit and the image sensor of the preparation mounted on the socket so as to cause the image sensor to image the object in the preparation.

11. The imaging apparatus according to claim 10, wherein:
the light source unit includes a plurality of light sources or a light source which is movable; and
the control device performs control so that light will be applied to the object a plurality of times at different angles so as to image the object at each of the different angles.

12. An imaging method comprising:
mounting the preparation according to claim 1 on a socket of an imaging apparatus so as to electrically connect the socket to the image sensor via the plurality of terminals of the package of the preparation;
emitting light from a light source unit to be incident on the image sensor via the transparent plate of the preparation; and
causing the image sensor to image the object in the preparation mounted on the socket by controlling the light source unit and the image sensor of the preparation.

13. The imaging method according to claim 12, wherein:
the light source unit includes a plurality of light sources or a light source which is movable; and
in the causing of the image sensor to image the object, light is applied to the object a plurality of times at different angles so as to image the object at each of the different angles.

14. A preparation producing apparatus comprising:
a table that supports slide glass on which a specimen section is placed; and
a movable unit that fixes an image sensor unit to the slide glass by bringing the image sensor unit close to the slide glass, the image sensor unit including an image sensor and a package, the image sensor having a front surface and a back surface, the package having a front surface and a rear surface, the package supporting the image sensor so that the front surface of the package contacts or opposes the back surface of the image sensor, the package including a plurality of terminals which are electrically connected to the image sensor via a plurality of electrodes, wherein
the slide glass is disposed so as to oppose the front surface of the image sensor,
the slide glass has first and second grooves on a surface which opposes the front surface of the image sensor,
at least part of the image sensor is disposed between the first and second grooves, and
at least part of each of the plurality of electrodes is positioned within the first groove or the second groove.

15. A preparation component set comprising:
an image sensor unit including an image sensor and a package, the image sensor having a front surface and a back surface, the package having a front surface and a rear surface and including a plurality of terminals which are electrically connected to the image sensor via a plurality of electrodes, the front surface of the package contacting or opposing the back surface of the image sensor; and
a transparent plate disposed so as to oppose the front surface of the image sensor with an object interposed therebetween, at least part of the object being covered with a mounting medium, wherein
the transparent plate has first and second grooves on a surface which opposes the front surface of the image sensor, and
at least part of the image sensor is positionable between the first and second grooves, and at least part of each of the plurality of electrodes is positionable within the first groove or the second groove.

* * * * *